US010765664B2

(12) United States Patent
Goldfeld et al.

(10) Patent No.: US 10,765,664 B2
(45) Date of Patent: Sep. 8, 2020

(54) TREATMENT OF INFECTIOUS DISEASES

(71) Applicant: CHILDREN'S MEDICAL CENTER CORPORATION, Boston, MA (US)

(72) Inventors: Anne Goldfeld, Cambridge, MA (US); Luke Jasenosky, Boston, MA (US); Viraga Haridas, Woburn, MA (US); Shahin Ranjbar, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 16/392,492

(22) Filed: Apr. 23, 2019

(65) Prior Publication Data

US 2019/0247367 A1 Aug. 15, 2019

Related U.S. Application Data

(62) Division of application No. 15/546,390, filed as application No. PCT/US2016/014865 on Jan. 26, 2016, now abandoned.

(60) Provisional application No. 62/107,872, filed on Jan. 26, 2015.

(51) Int. Cl.
*A61K 31/426* (2006.01)
*A61K 45/06* (2006.01)

(52) U.S. Cl.
CPC ............ *A61K 31/426* (2013.01); *A61K 45/06* (2013.01); *A61K 2300/00* (2013.01); *Y02A 50/385* (2018.01)

(58) Field of Classification Search
CPC .. A61K 31/426; A61K 45/06; A61K 2300/00; Y02A 50/385
USPC ....................................................... 514/371
See application file for complete search history.

(56) References Cited

U.S. PATENT DOCUMENTS

| | | |
|---|---|---|
| 2012/0294831 A1 | 11/2012 | Rossignol |
| 2013/0171103 A1 | 7/2013 | Davis et al. |
| 2013/0253008 A1 | 9/2013 | Ivachtchenko et al. |
| 2014/0112888 A1 | 4/2014 | Rossignol |
| 2014/0134265 A1 | 5/2014 | Buggy et al. |

FOREIGN PATENT DOCUMENTS

WO 2012/139028 A2 10/2012

OTHER PUBLICATIONS

Elazar et al., The Anti-Hepatitis C Agent Nitazoxanide Induces Phosphorylation of Eukaryotic Initiation Factor 2alpha Via Protein Kinase Activated by Double-Stranded RNA Activation, 2009, Gastroenterology, vol. 137, Issue 5, 1827-1835 (Year: 2009).*
Brass et al., "The IFITM proteins mediate cellular resistance to influenza A H1N1 virus, West Nile virus, and dengue virus." Cell 139(7):1243-1254 (2009).
Gekonge et al., "Short communication: Nitazoxanide inhibits HIV viral replication in monocyte-derived macrophages", AIDS Research and Human Retrovirus 31(12):237-241 (2015).
Haffizulla et al., "Effect of nitazoxanide in adults and adolescents with acute uncomplicated influenza: a double-blind, randomised, placebo-controlled, phase 2b/3 trial." The Lancet Infectious Diseases 14(7):609-618 (2014).
Huang et al., "Distinct patterns of IFITM-mediated restriction of filoviruses, SARS coronavirus, and influenza A virus." PLoS Pathogens 7(1):e1001258 (2011).
Korba et al., "Nitazoxanide, tizoxanide and other thiazolides are potent inhibitors of hepatitis B virus and hepatitis C virus replication." Antiviral Research 77(1):56-63 (2008).
Lu et al., "The IFITM proteins inhibit HIV-1 infection." Journal of Virology 85(5):2126-2137 (2011).
Rossignol et al., "A double-'blind'placebo-controlled study of nitazoxanide in the treatment of cryptosporidial diarrhoea in AIDS patients in Mexico." Transactions of the Royal Society of Tropical Medicine and Hygiene 92 (6):663-666 (1998).
Rossignol et al., "Clinical trial: randomized, double-blind, placebo-controlled study of nitazoxanide monotherapy for the treatment of patients with chronic hepatitis C genotype 4." Alimentary Pharmacology & Therapeutics 28 (5):574-580 (2008).
Rossignol et al., "Improved virologic response in chronic hepatitis C genotype 4 treated with nitazoxanide, peginterferon, and ribavirin." Gastroenterology 136(3):856-862 (2009).
Stachulski et al., "Thiazolides as novel antiviral agents. 1. Inhibition of hepatitis B virus replication." Journal of Medicinal Chemistry 54(12):4119-4132 (2011).
Zhu et al., "IFITM3-containing exosome as a novel mediator for anti-viral response in dengue virus infection." Cellular Microbiology 17(1):105-118 (2015).

* cited by examiner

*Primary Examiner* — Kristin A Vajda
(74) *Attorney, Agent, or Firm* — Nixon Peabody LLP; David S. Resnick; Mark J. FitzGerald

(57) ABSTRACT

Disclosed herein are methods for treating or preventing a disease comprising administering a pharmaceutical composition comprising a therapeutically-effective amount of nitazoxanide to a subject having the disease, wherein the disease is causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*.

14 Claims, 34 Drawing Sheets
Specification includes a Sequence Listing.

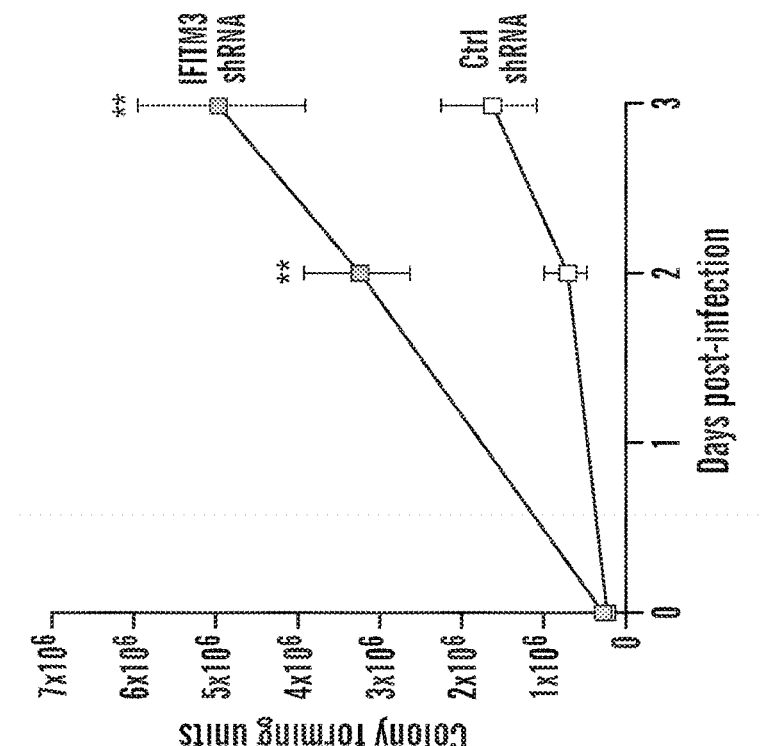
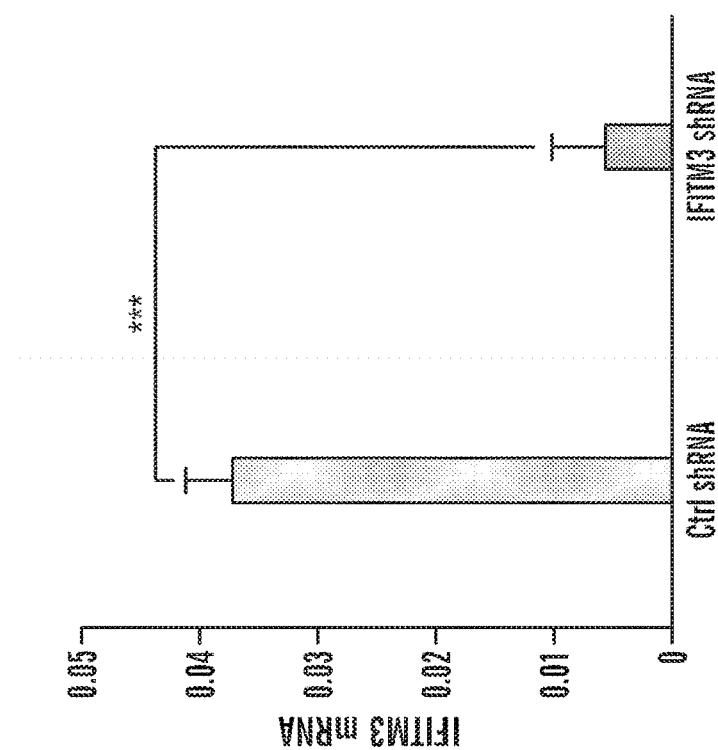
FIG. 1A
FIG. 1B

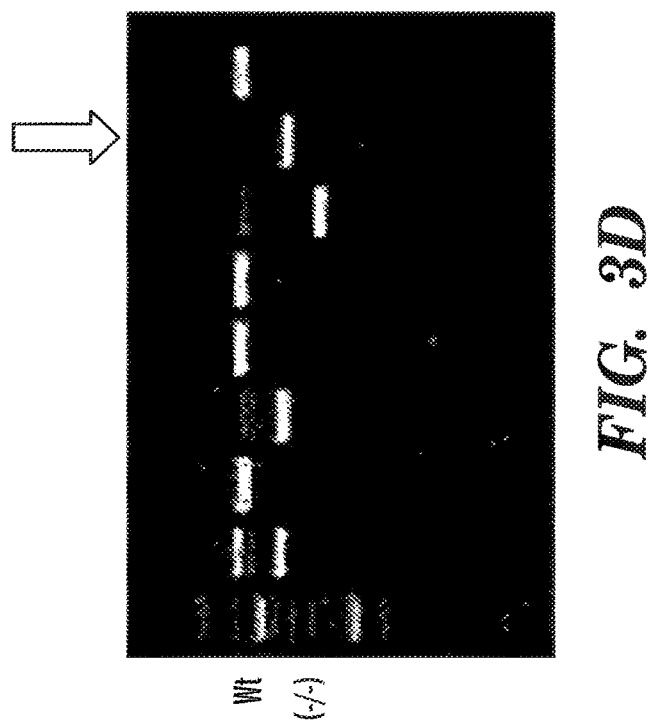
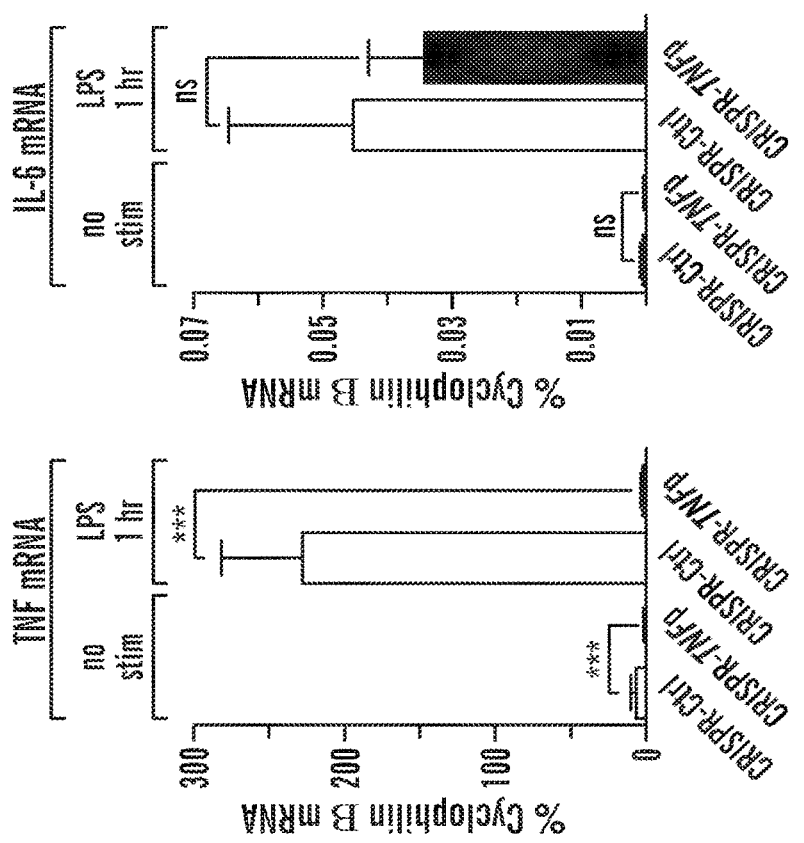
FIG. 3C
FIG. 3D

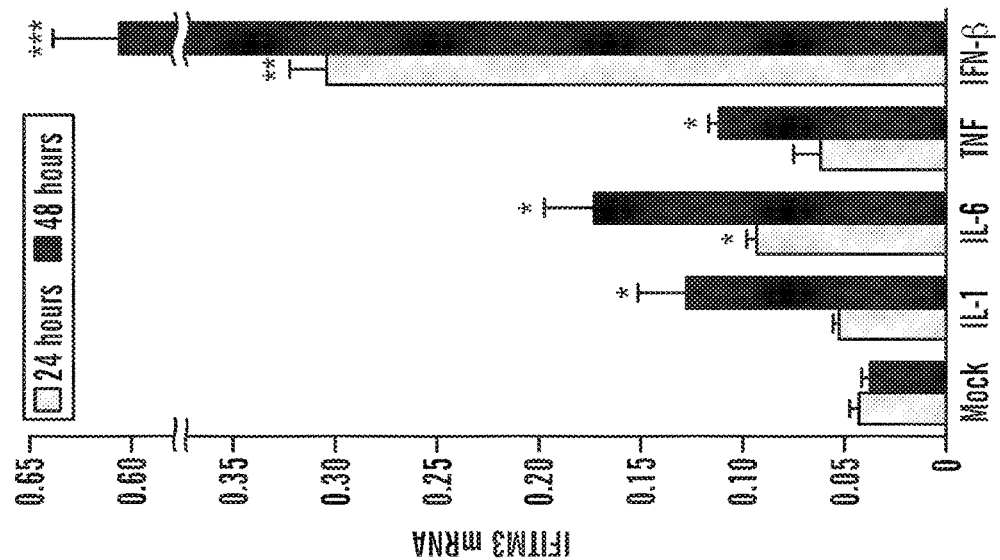
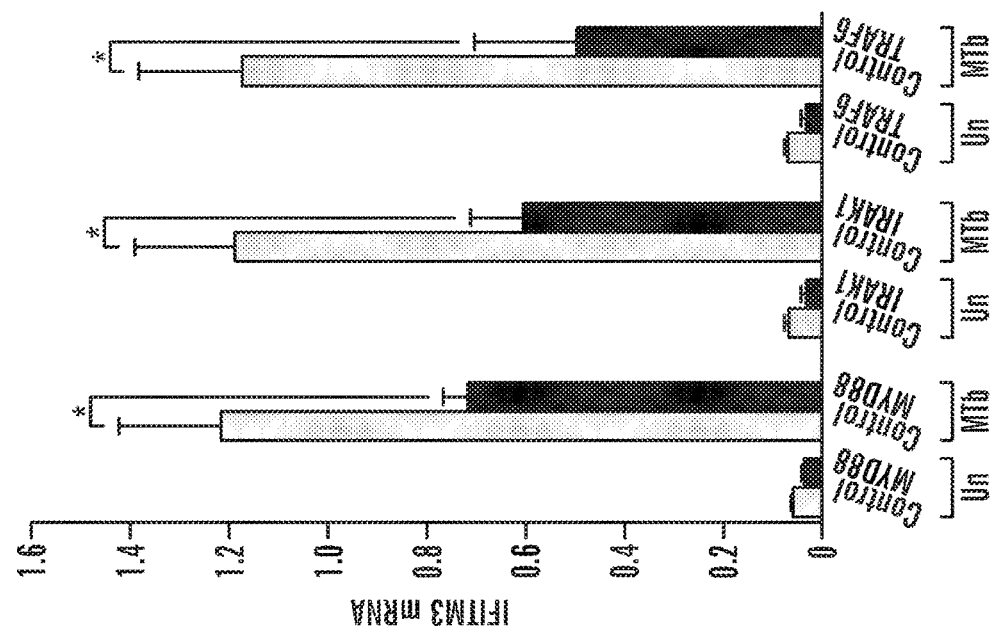

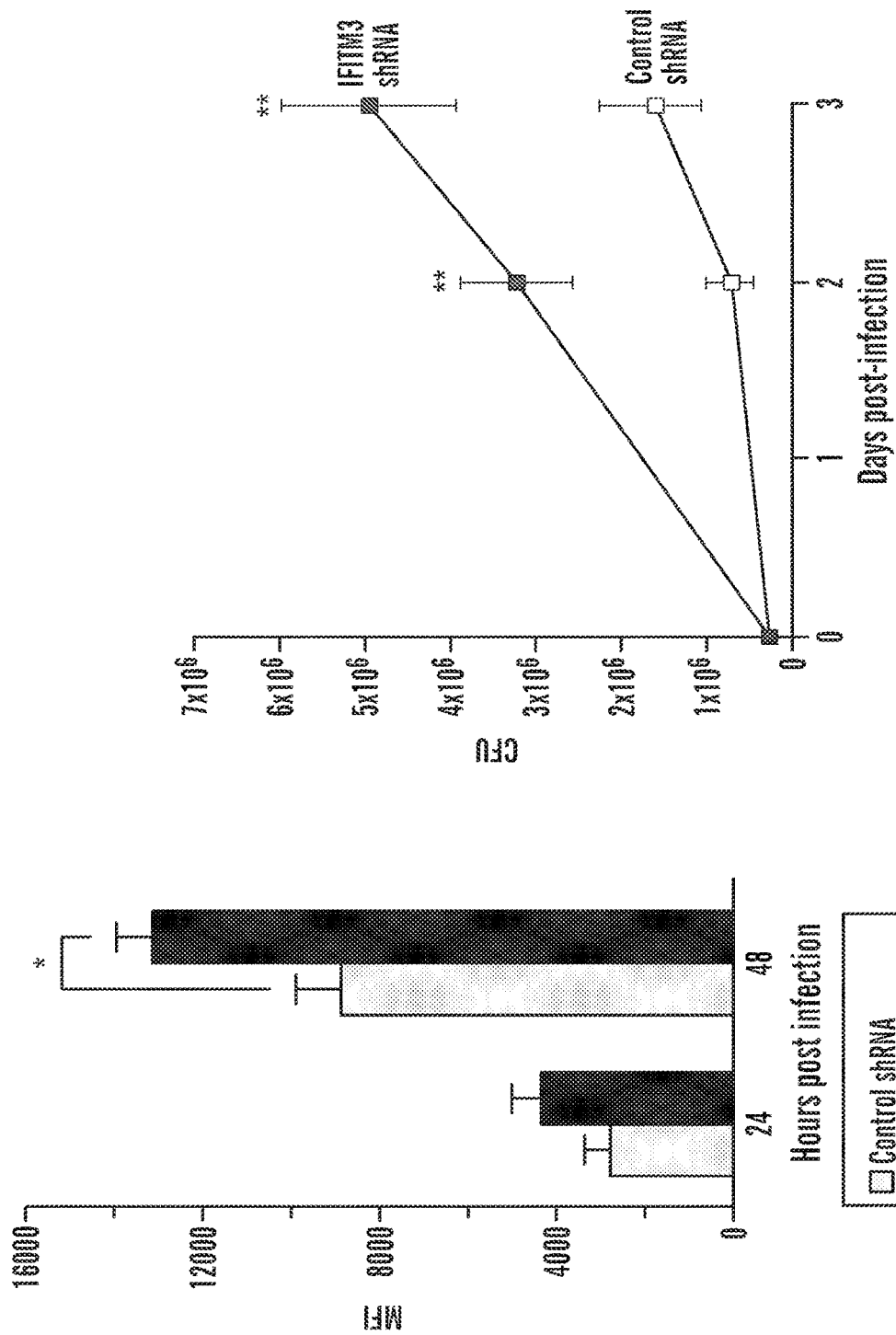

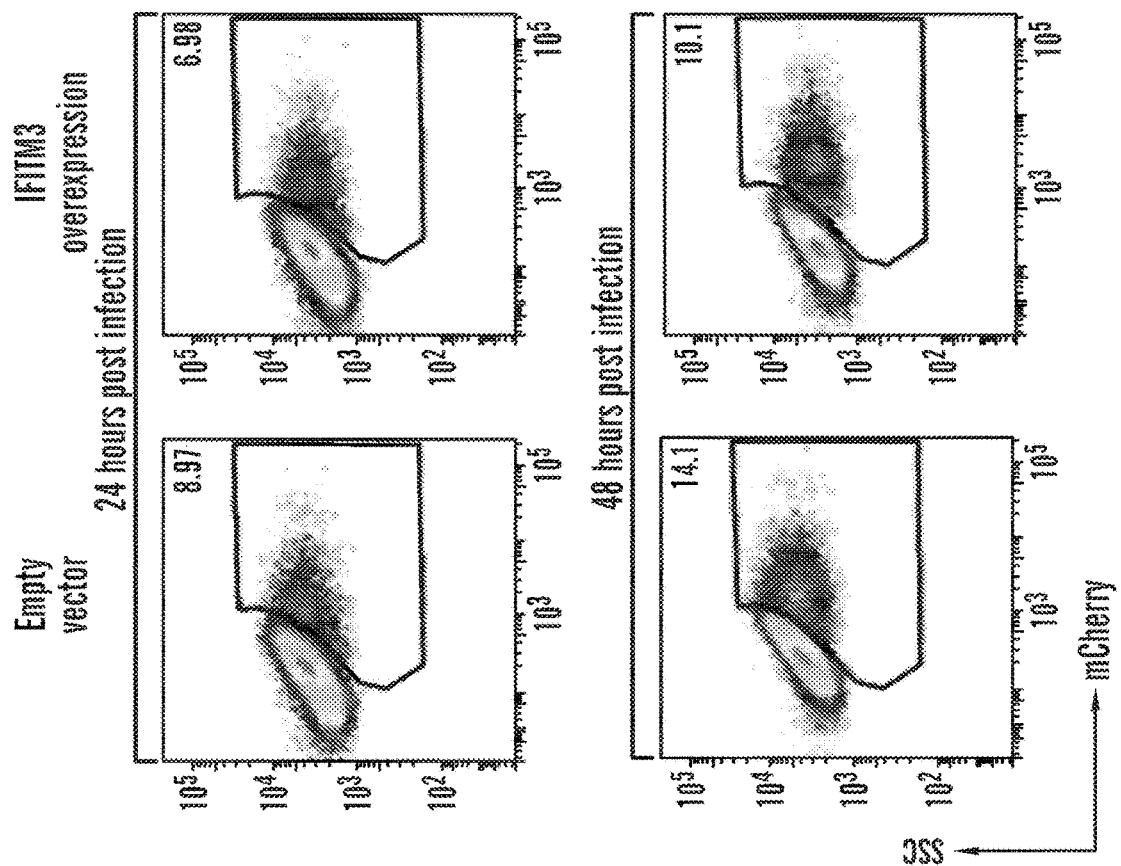
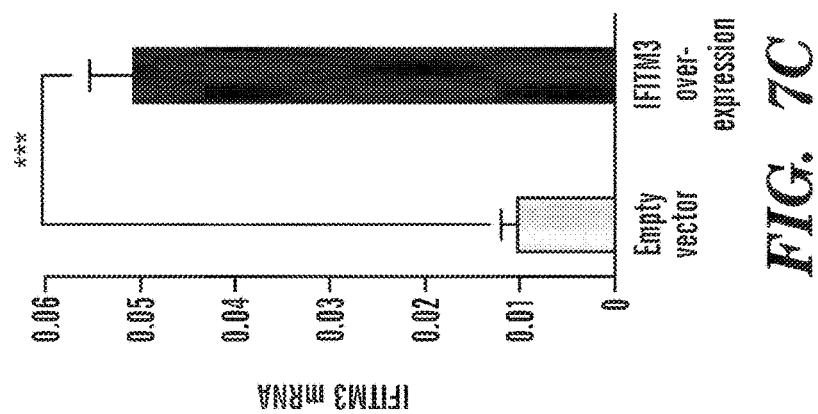
FIG. 7D
FIG. 7C

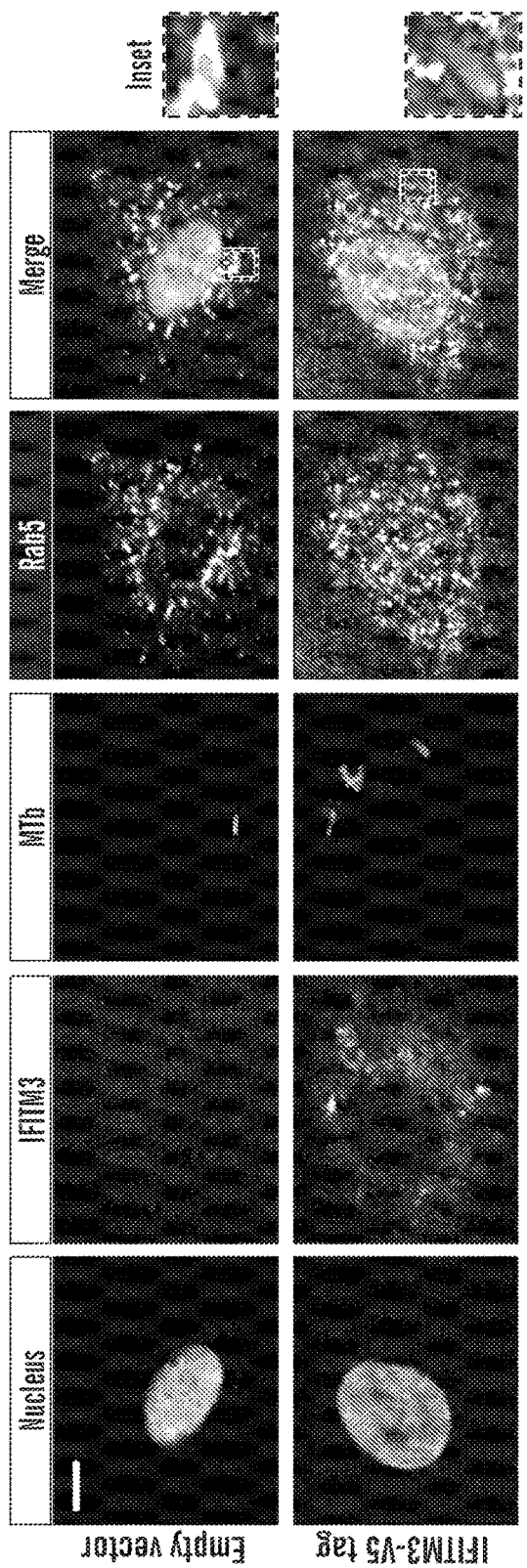
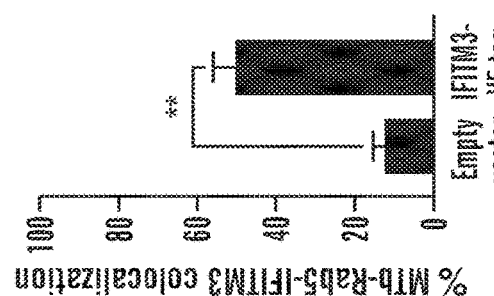
FIG. 8A
FIG. 8B

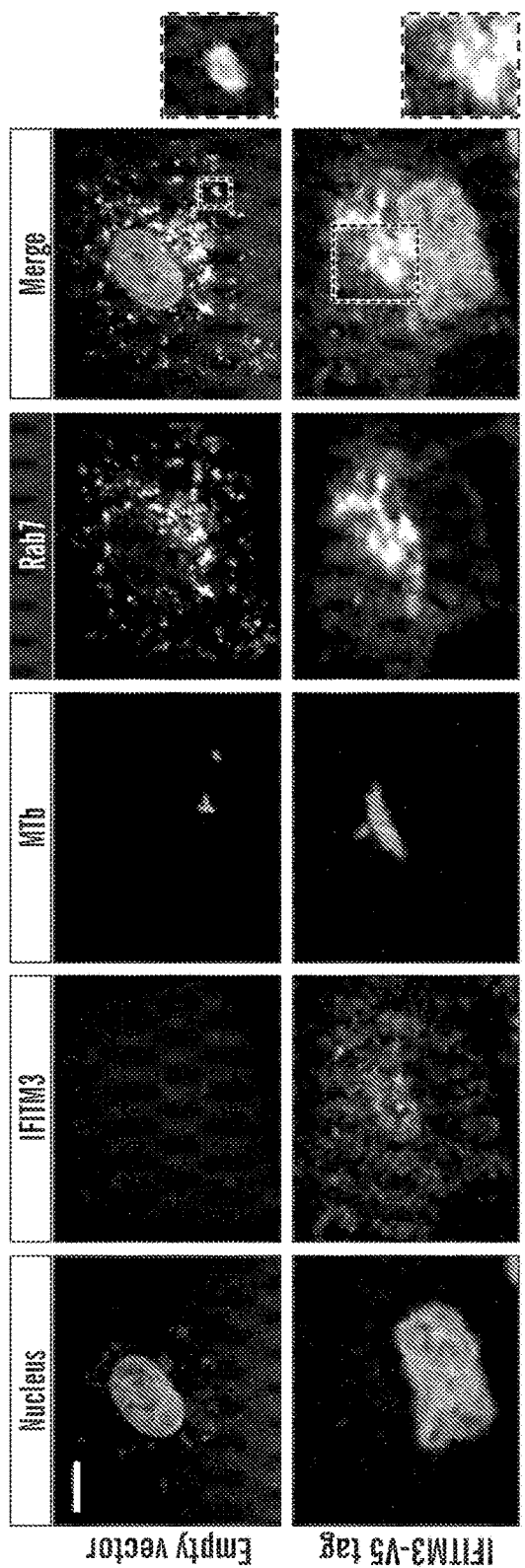
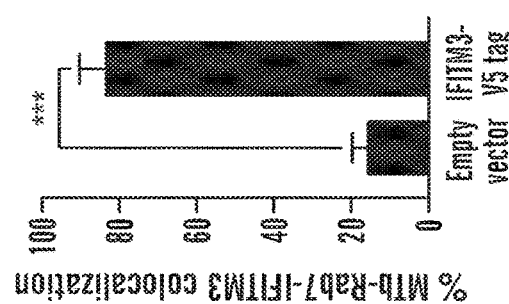
FIG. 8C
FIG. 8D

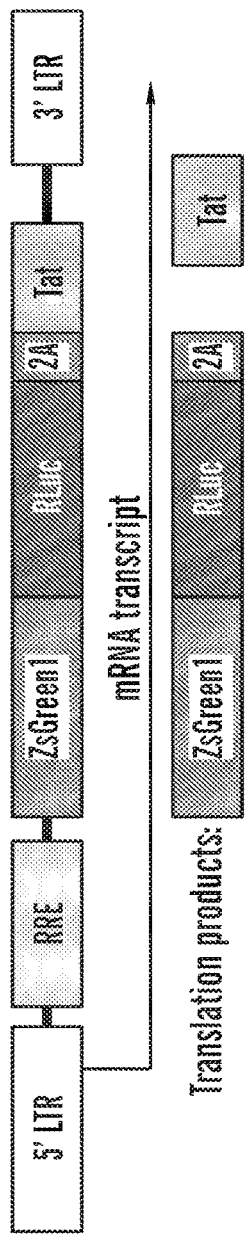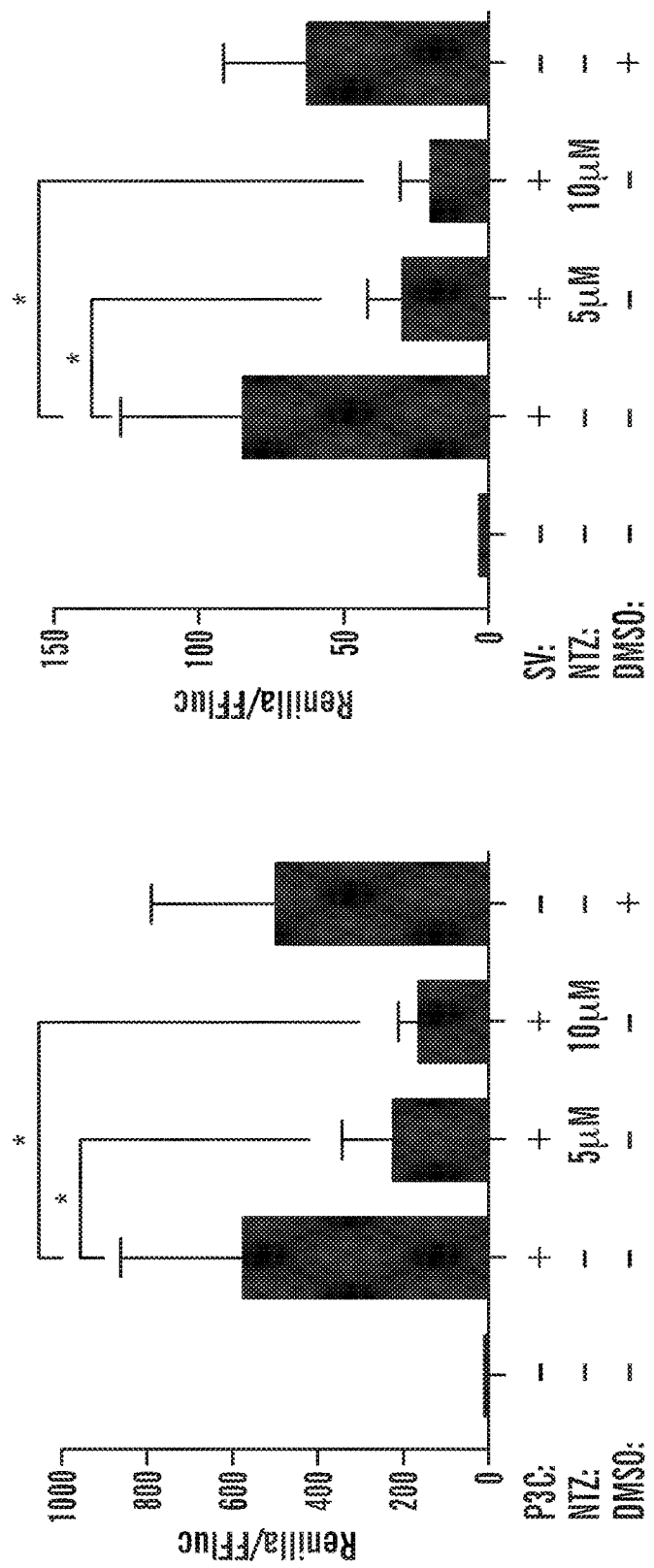
FIG. 16A
FIG. 16B
FIG. 16C

TREATMENT OF INFECTIOUS DISEASES

CROSS-REFERENCE TO RELATED APPLICATIONS

This application is a divisional of co-pending U.S. application Ser. No. 15/546,390 filed Jul. 26, 2017, which is a 35 U.S.C. § 371 National Phase Entry Application of International Application No. PCT/US2016/014865 filed Jan. 26, 2016, which designates the U.S. and claims benefit under 35 U.S.C. § 119(e) of U.S. Provisional Application No. 62/107,872, filed Jan. 26, 2015, the contents of which are incorporated herein by reference in their entireties.

TECHNICAL FIELD

The present invention relates to methods of treatment for infectious diseases.

SEQUENCE LISTING

The instant application contains a Sequence Listing which has been submitted electronically in ASCII format and is hereby incorporated by reference in its entirety. Said ASCII copy, created on Nov. 16, 2017, is named 701039-083232-USSL.txt and is 3,471 bytes in size.

BACKGROUND

Ebola virus (EboV) is a highly pathogenic enveloped virus that causes outbreaks of zoonotic infection in Africa. EboV is transmitted by close contact and virus levels increase by 75-fold/day for several days after initial infection. The clinical symptoms are manifestations of the massive production of pro-inflammatory cytokines in response to infection and in many outbreaks, mortality exceeds 75%. The endothelial cell dysfunction associated with "cytokine storm" results in capillary leak, hypovolemic shock, disseminated intravascular coagulation and inadequate perfusion of major organs. The unpredictable onset, ease of transmission, rapid progression of disease, high mortality and lack of effective vaccine or therapy have created a high level of public concern abo-ut EboV. The 2014 Ebola outbreak in West Africa has resulted in total deaths of about 8200, out of about 21000 cases. The high mortality is partly attributed to the lack of effective anti-EboV vaccine or therapy. Therefore, development of anti-EboV drugs is of great importance.

SUMMARY

It was discovered that nitazoxanide (NTZ) can induce the transcription of interferon-induced transmembrane (IFITM) genes. IFITM proteins have been shown to have beneficial effects in restricting certain viral infections. It was further discovered that NTZ inhibits *Zaire ebolavirus* infection. In addition, NTZ was found to induce transcription of the interferon inducible PKR and virus inducible RIG-I genes in HeLa cells. PKR and RIG-I are critical sensors of viral infection and their activation induces antiviral responses that restrict virus replication and release, including type I IFN production and, in the case of PKR, global translation shutdown. In the case of Ebola virus infection, activation of these molecules would putatively bypass inhibition that Ebola itself activates of the antiviral response due to viral factors, including the Ebola virus VP35 protein, which impedes PKR sensing of the Ebola virus genome.

In one aspect, the technology described herein relates to a method of treating a disease comprising administering a pharmaceutical composition comprising a therapeutically-effective amount of nitazoxanide or a related thiazolide to a subject having the disease, wherein the disease is causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*.

In one aspect, the technology described herein relates to a method of preventing a disease comprising administering a pharmaceutical composition comprising a therapeutically-effective amount of nitazoxanide or a related thiazolide to a subject having the disease, wherein the disease is causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*.

In one embodiment of any one of the foregoing aspects, the disease is causally linked to infection by one or more pathogens selected from the group consisting of members of the genus *Ebolavirus*, members of the genus *Marburgvirus*, members of the species dengue virus, and human immunodeficiency viruses 1 and 2.

In one embodiment of any one of the foregoing aspects, the pharmaceutical composition comprises nitazoxanide as the sole therapeutically-effective ingredient.

In one embodiment of any one of the foregoing aspects, the pharmaceutical composition comprises nitazoxanide in combination with another therapeutically-effective ingredient.

In one embodiment of any one of the foregoing aspects, the therapeutically-effective amount of nitazoxanide is in the range of 200-3000 milligrams per day.

In one embodiment of any one of the foregoing aspects, the administering is oral.

In one embodiment of any one of the foregoing aspects, the subject is a mammal.

In one embodiment of any one of the foregoing aspects, the subject is a human.

In one embodiment of any one of the foregoing aspects, the subject has tuberculosis and HIV infection.

In one aspect, the technology described herein relates to a method of reducing the likelihood of an active recrudescent HIV infection in a subject, wherein the infection has become latent, the method comprising administering to the subject a therapeutically-effective amount of nitazoxanide.

In another aspect, the technology described herein relates to a method of increasing the expression level of a protein in a cell selected from the group consisting of an interferon-induced transmembrane (IFITM) protein, protein kinase R (PKR), retinoic acid-inducible gene 1 (RIG-I), and growth arrest and DNA damage-inducible protein (GADD34), the method comprising contacting the cell with nitazoxanide.

In one embodiment, the IFITM protein is selected from the group consisting of IFITM1, IFITM2, IFITM3, and IFITM5.

In one aspect, the technology described herein relates to a method of inducing anti-viral stress response in a cell, the method comprising contacting the cell with nitazoxanide.

In one embodiment, the stress response is formation of stress granules and increase in cellular acidity.

In another aspect, the technology described herein relates to a method of increasing phosphorylation of eIF2α in a cell, the method comprising contacting the cell with nitazoxanide.

In one embodiment, the contacting is in vitro.

In one embodiment, the contacting is in vivo.

In one embodiment, the in vivo contacting is done in a mammal.

In one embodiment, the mammal is a human.

In one aspect, the technology described herein relates to use of nitazoxanide for the treatment of a disease causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis.*

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A-1D are graphs showing that IFITM3 is required for host restriction of TB, and that NTZ induces IFITM3 and inhibits TB growth and replication. (FIG. 1A) Successful knockdown of IFITM3 expression in THP-1 cells. (FIG. 1B) IFITM3-KD cells are significantly more susceptible to MTb infection. (FIG. 1C) NTZ inhibits MTb (labeled with mCherry) infection of THP-1 cells. (FIG. 1D) NTZ induces IFITM3 mRNA expression in human macrophages.

FIGS. 2A-2B are graphs showing that NTZ inhibits Ebola-pseudotyped lentiviral infection of THP1 cells by 40%. This is also demonstrated in A549 cells. (FIG. 2A) THP-1 cells were treated with NTZ at 0 or 8 μM for 5 days, at which time cell death was measured using a live/dead cell stain. No toxicity of sustained NTZ treatment was detected. (FIG. 2B) THP-1 cells were pre-treated with NTZ at 0 or 8 μM for 4 hours, and were then infected with *Zaire ebolavirus* GP-pseudotyped lentivirus by spinoculation for 30 min. After 5 days, cells were analyzed by flow cytometry to detect EGFP+ cells as a surrogate of infection rate. FACS plots from a representative experiment are shown. Left: untreated, uninfected THP-1 cells.

FIG. 3A is a schematic representation of the lentiviral vector. Expression of two unique gRNA sequences is driven by U6 and H1 promoters, respectively.

FIG. 3B shows sequences in the TNF promoter targeted with dCas9-KRAB (SEQ ID NO: 11); red box indicates TSS of TNF; "PAM" indicates protospacer adjacent motif sequence.

FIG. 3C is a set of graphs showing that THP-1 cells were transduced with a dCas9-KRAB-2A-E2Crimson lentivirus encoding two i) non-specific gRNAs (CRISPR-Ctrl) or ii) TNF minimal promoter-specific gRNAs (CRISPR-TNFp). E2-Crimson+ cells were sorted, expanded, and stimulated with 100 ng/ml LPS for 1 hr or left unstimulated. Levels of TNF (left) and IL-6 (right) mRNA were measured by qPCR and normalized to cyclophilin B mRNA levels.

FIG. 3D is an imaging showing deletion of 325 bp from the TNF/LT locus in THP-1 cells. THP-1 cells were transduced with the lentiviral vector shown in (A) except that dCas9-KRAB was replaced by wild-type Cas9 and the guide RNAs were specific to two sites, ~325 bp apart, 12 kb upstream of the TNF promoter. After enrichment for E2-Crimson+ cells by FACS, cells were single-cell sorted, expanded and individual clones were analyzed by PCR to detect the presence or absence of the deletion. A clone containing a homozygous deletion of 325 bp (confirmed by sequencing) is indicated by the red arrow.

FIG. 4 is a set of graphs showing that human PBMC were treated with NTZ at the indicated concentrations for 72 hrs and cellular supernatants were analyzed by Luminex assay to quantitate cytokine levels. Of the cytokines analyzed (TNF, IL-1β, IL-2, IL-4, IL-6, IL-8, IL-10, and IFN-γ) only IL-1β and IL-6 showed changes over baseline. Means of two donors and SEM are shown.

FIGS. 5A-5E shows that IFITM3 gene expression is induced in human macrophages and monocytic cells in response to MTb infection via TLR2/4- and MyD88-dependent signaling pathways. (FIG. 5A) MDMs were left uninfected (mock) or infected with MTb strains CDC1551, HN878, or H37Rv as indicated for 3, 24, and 48 hours at a 1:10 ratio of cells:bacilli. (FIG. 5B) THP-1 cells were left uninfected (mock) or infected with MTb strain H37Rv (1:10 cells:bacilli) for 3, 6, 24, and 48 hours. (FIG. 5C) THP-1 cells were left untreated (mock) or treated with the TLR2 agonist Pam3Cys (100 ng/ml) or the TLR4 agonist LPS (100 ng/ml) for 24 and 48 hours. (FIG. 5D) THP-1 cells that constitutively express lentivirally delivered shRNAs targeting MyD88, IRAK1, and TRAF6, or control shRNA, were infected with MTb strain H37Rv (1:10 cells:bacilli) or left uninfected (mock) for 24 and 48 hours. (FIG. 5E) THP-1 cells were left untreated (mock) or treated with recombinant IL-1β (100 ng/ml), IL-6 (50 ng/ml), TNF (10 ng/ml), MCP-1 (50 ng/ml), or IFN-β (100 ng/ml) for 24 and 48 hours. IFITM3 and cyclophilin B mRNA levels were assayed using quantitative real time PCR. Results are the mean±SEM from three independent experiments (*, $p<0.05$; **, $p<0.01$).

FIGS. 6A-6D show that inhibition of endogenous IFITM3 increases MTb replication. (FIG. 6A) IFITM3 mRNA levels and IFITM3 protein levels were measured in THP-1 transduced with a lentiviral vector encoding shRNA against IFITM3 or control shRNA. (FIG. 6B) IFITM3-KD and control THP-1 cells were infected with MTb strain H37Rv-mCherry (1:10 cells:bacilli) for 24 or 48 hours and analyzed by flow cytometry. Dot plots are representative of three independent experiments, and show percentage of cells infected with MTb. (FIG. 6C) Mean fluorescence intensity (MFI) of MTb-mCherry-infected IFITM3-KD and control THP-1 cells 24 and 48 hours after infection. Results are the mean±SEM from three independent experiments. (FIG. 6D) CFU assay of IFITM3-KD and control THP-1 cells at days 2 and 3 post-infection with H37Rv-MTb. Results are the mean±SEM from four independent experiments (*, $p<0.05$; **, $p<0.01$).

FIGS. 7A-7D show that IFITM3 regulates MTb replication in alveolar epithelial cells. (FIG. 7A) IFITM3 mRNA levels in A549 cells transduced with IFITM3 shRNA compared with cells transduced with control shRNA (*, $p<0.005$). (FIG. 7B) Flow cytometry analysis of MTb-mCherry infection of IFITM3-KD and control A549 cells at 24 and 48 hours post-infection (1:1 cells:bacilli). (FIG. 7C) IFITM3 mRNA levels in A549 cells transduced with IFITM3 overexpression plasmid compared with empty plasmid (control) (*, $p<0.005$). (FIG. 7D) Flow cytometry analysis of MTb-mCherry levels in A549 cells transduced with IFITM3 overexpressing plasmid or empty plasmid 24 and 48 hours post-infection (1:1 cells:bacilli). Results are representative of three independent experiments.

FIGS. 8A-8D show that IFITM3 co-localizes with MTb in early and late phagosomes. A549 cells transduced with IFITM3-V5 tagged (IFITM3) or empty vector (vector). Cells were infected with MTb H37Rv-mCherry as described in Materials and Methods. (FIG. 8A) MTb-(red) infected cells were immunostained with anti-V5 (IFITM3, green), anti-Rab5 (white), and DAPI (nuclei, blue). (FIG. 8B) Quantification of (A), showing percent of MTb co-localization with IFITM3 and Rab5. (FIG. 8C) MTb-(red) infected cells were immunostained with anti-V5 (IFITM3, green), anti-Rab7 (white) and DAPI (nuclei, blue). (FIG. 8D) Quantification of (FIG. 8C), showing percent of MTb co-localization with IFITM3 and Rab7. Scale bar: 10 uM. Enlarged images in the right hand side of merge images show the MTb-containing phagosomes. Data are representative of four independent experiments. Results are the mean+SEM (, $p<0.01$; *, $p<0.005$).

FIGS. 9A-9D show that engagement of TLR2 and TLR4 induces the expression of inflammatory cytokines that have an inhibitory effect on MTb replication. THP-1 cells were left untreated (mock) or treated with the TLR2 agonist Pam3Cys (100 ng/ml) or the TLR4 agonist LPS (100 ng/ml) for 24 and 48 hours. mRNA levels were then assayed for (FIG. 9A) IL-1β (FIG. 9B) IL-6, (FIG. 9C) IFN-β, and (FIG. 9D) TNF. Results are the mean+SEM from three independent experiments. (*, $p<0.05$; , $p<0.01$; *, $p<0.005$).

Figure 10A:
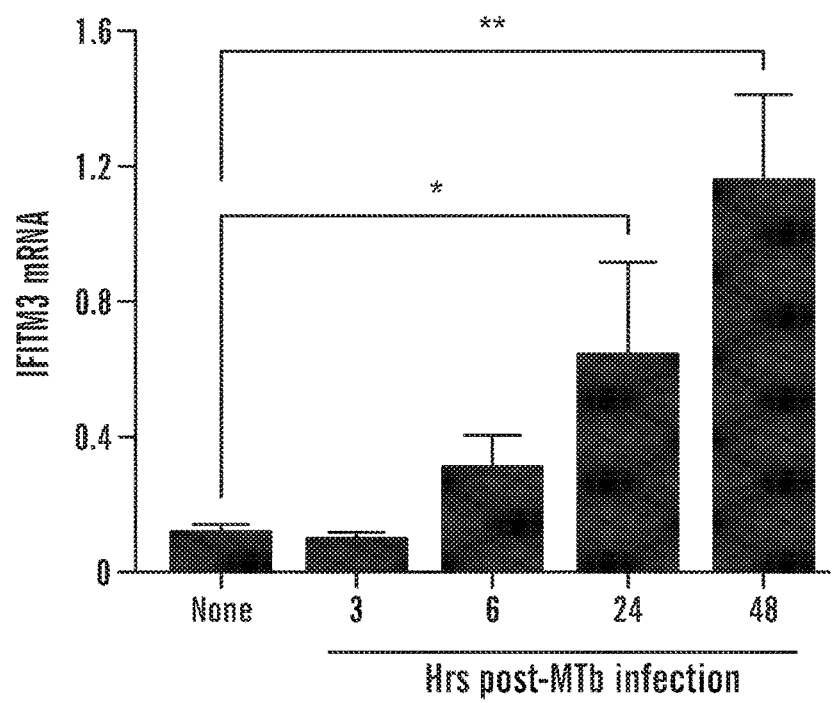
FIG. 10A shows that MTb infection induces IFITM3 transcription. THP-1 cells were infected with H37RvmCherry MTb, RNA was harvested at 3, 6, 24, and 48 hours after infection, and qRT-PCR was performed with IFITM3-specific primers. mRNA levels were normalized to those of cyclophilin B.
Figure 10B:
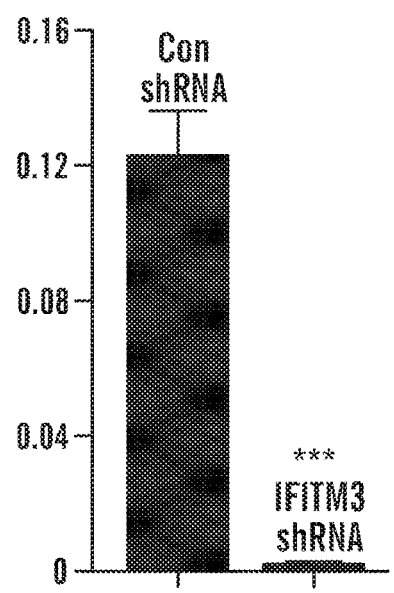
FIG. 10B shows that IFITM3 shRNA in THP-1 cells inhibits IFITM3 mRNA synthesis.
Figure 10C:
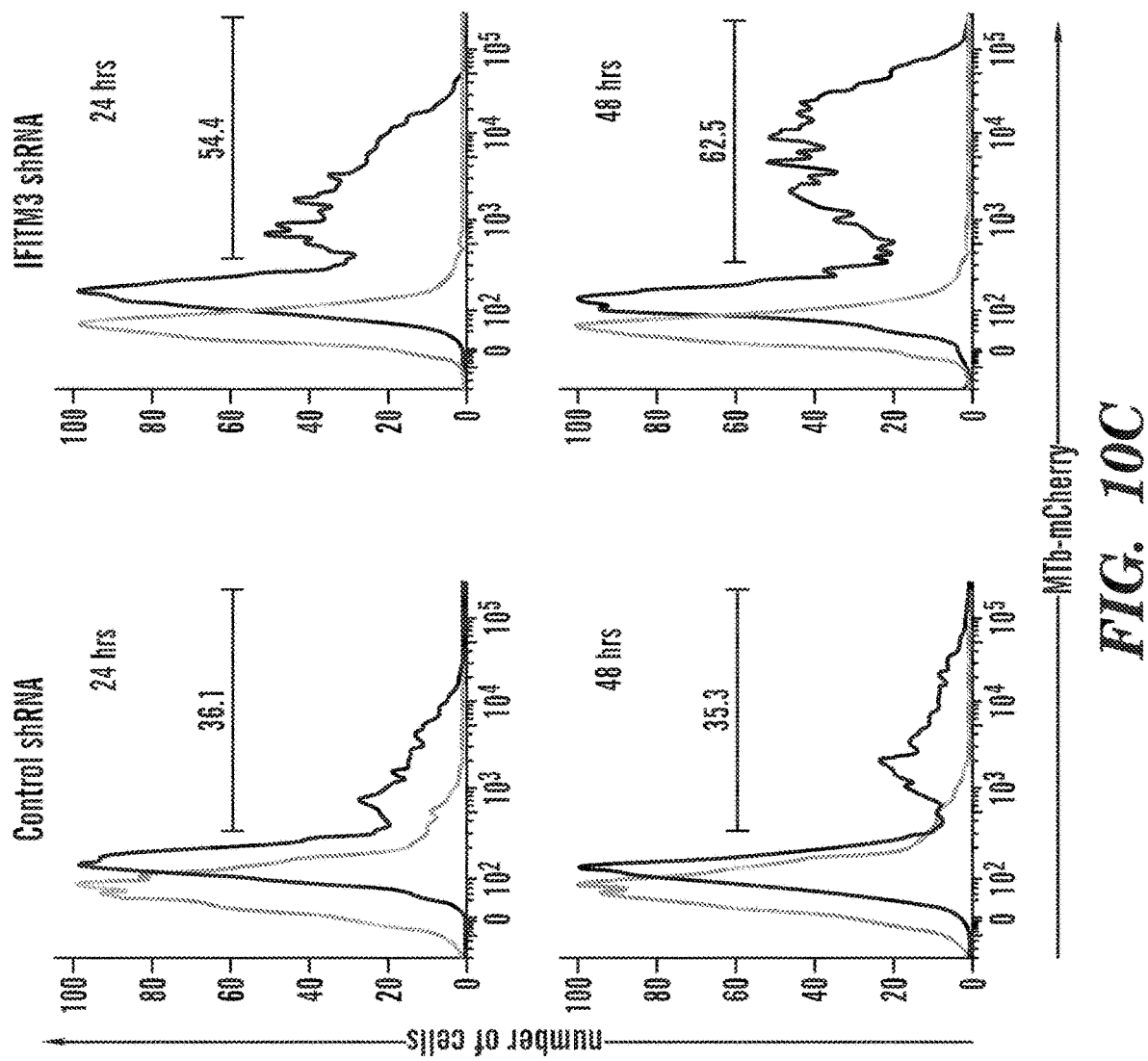

FIG. 10C shows that inhibition of IFITM3 expression enhances MTb growth. FACS analysis of uninfected (red) and mCherry-MTb infected (blue) THP-1 cells expressing control (left) or IFITM3 (right) shRNA, 24 h (top) or 48 h (bottom) post-infection. Bars indicate % of MTb-infected cells.

Figure 10D:
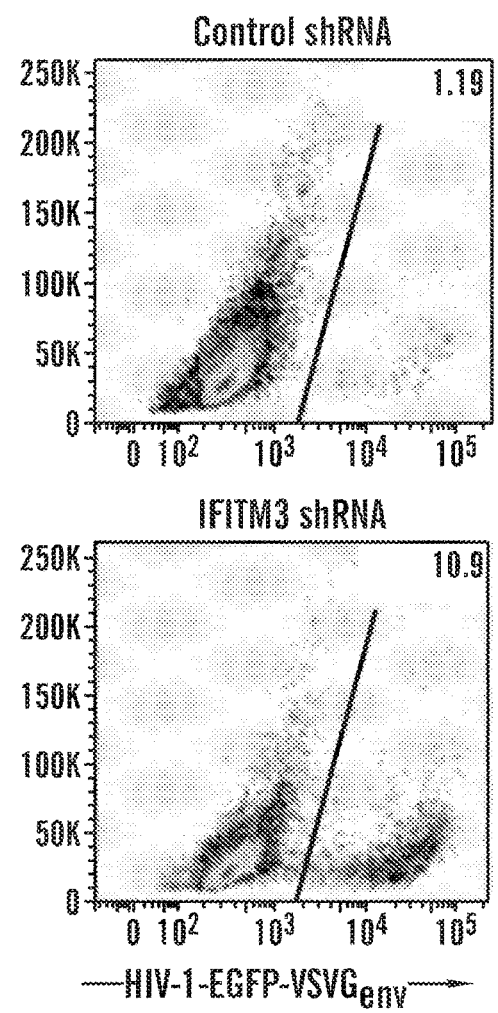

FIG. 10D shows that inhibition of IFITM3 expression enhances VSV-pseudotyped HIV infection. FACS analysis showing percentages of HIV-1-EGFP-VSVG$_{env}$-infected THP-1 cells expressing control or IFITM3 shRNA 48 h postinfection.

Figure 10E:
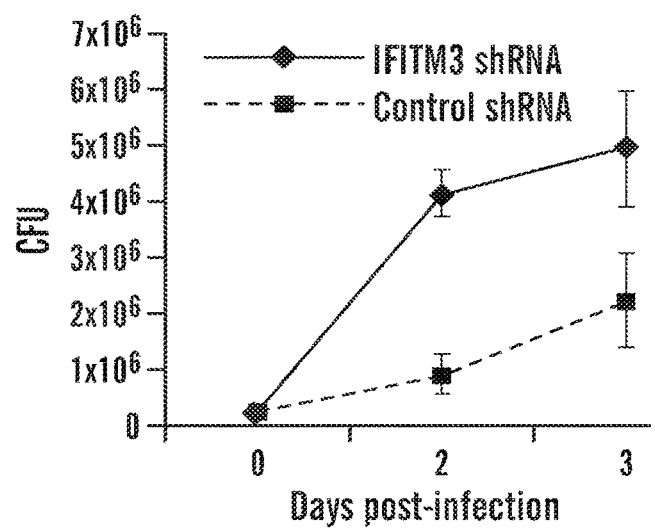

FIG. 10E shows that CFU from IFITM3 knockdown and control shRNA THP-1 cells after infection with MTb strain H37Rv.

Figure 10F:
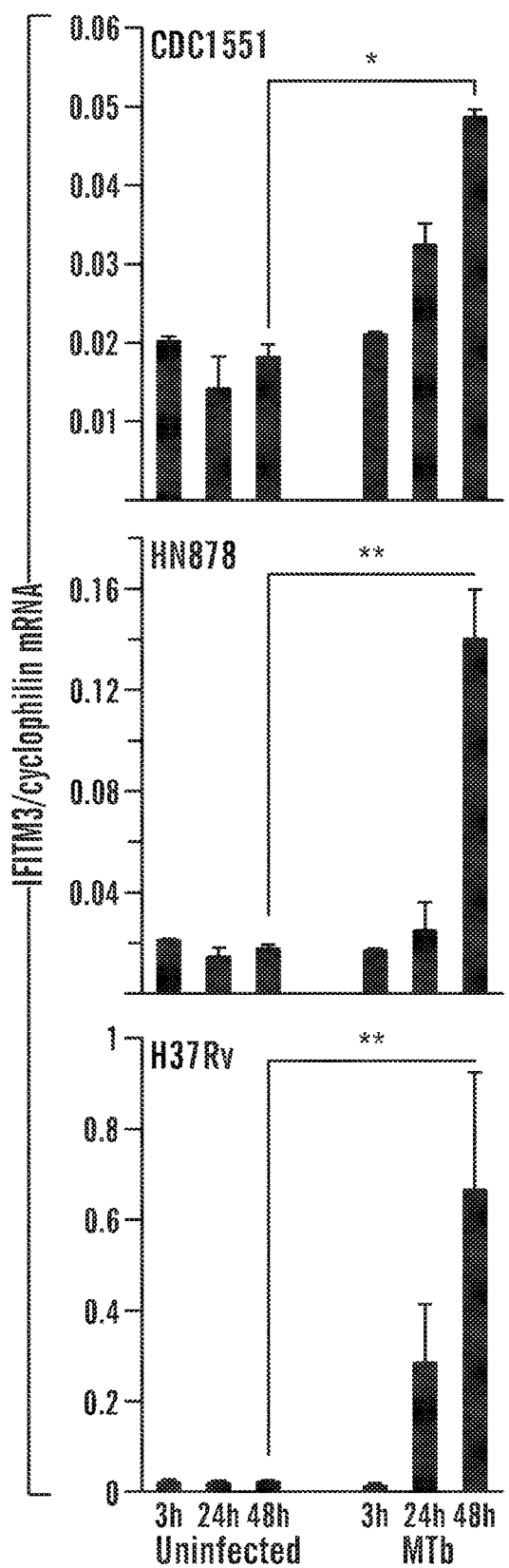

FIG. 10F shows that different strains of MTb induce distinct levels of IFITM3 mRNA. MDM were infected with three strains and RNA was harvested at 3, 24, and 48 h. IFITM3 and cyclophilin B mRNA were measured by qPCR. *=$p<0.05$; =$p<0.01$; *=$p<0.001$.

Figure 11A:
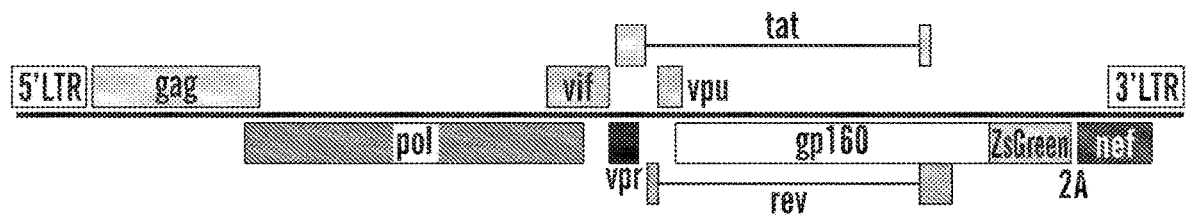

FIG. 11A is a schematic showing the genomic structure of ZsGreen1 reporter viruses.

Figure 11B:
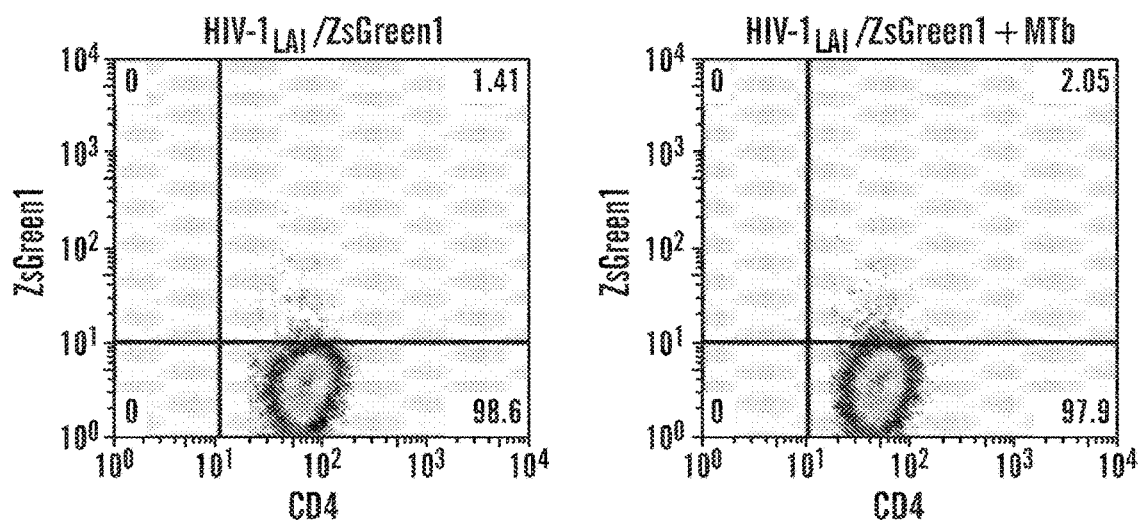

FIG. 11B shows that PBMC were infected with HIV-1LAI/ZsGreen1 (X4-tropic) or HIV-1BAL/ZsGreen1 (R5-tropic) at 100 TCID50 and, after 48 hours, analyzed by FACS.

Figure 12A:
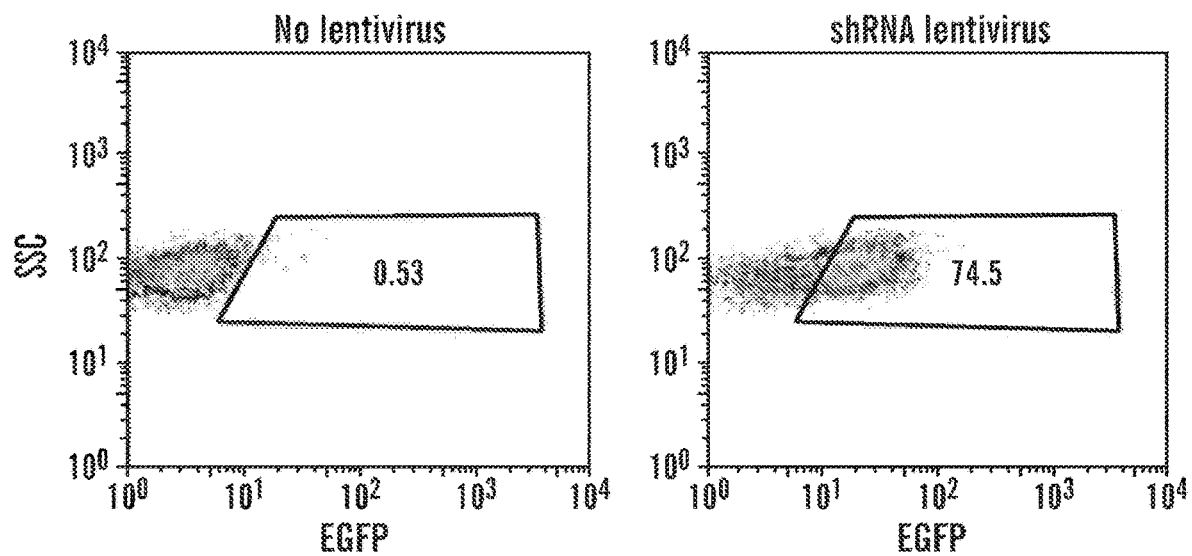

FIG. 12A shows that primary human monocytes were transduced with an shRNA lentivirus encoding EGFP by spinoculation for 90 minutes. EGFP signal was measured by FACS after 48 hrs.

Figure 12B:
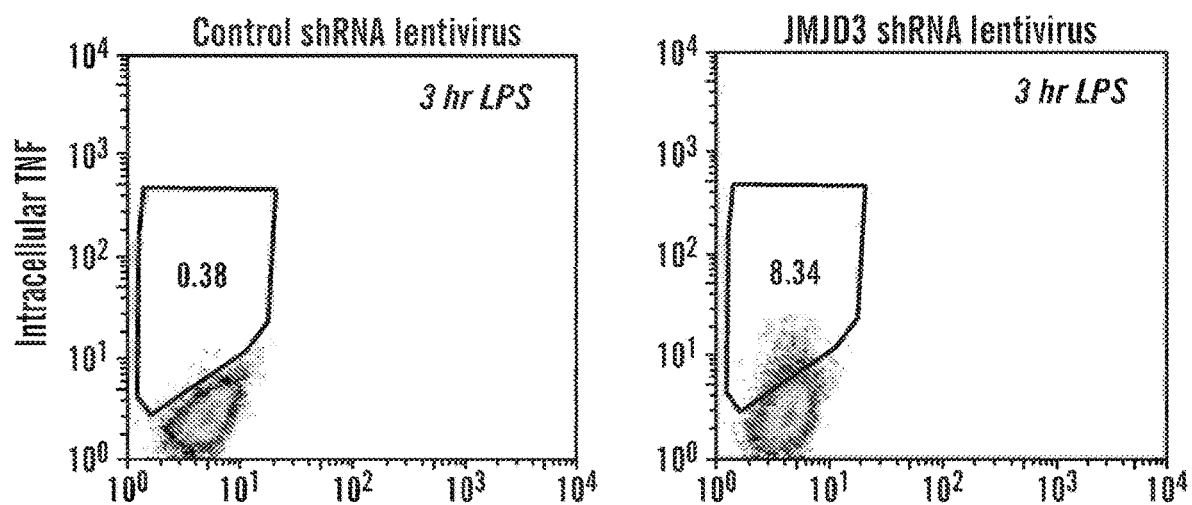

FIG. 12B shows that primary human monocytes were transduced with control or JMJD3-specific shRNA lentiviruses and, after 48 hrs, stimulated with LPS (1 µg/ml) for 3 hrs in the presence of brefeldin A. Intracellular TNF was assessed by FACS.

Figure 13A:
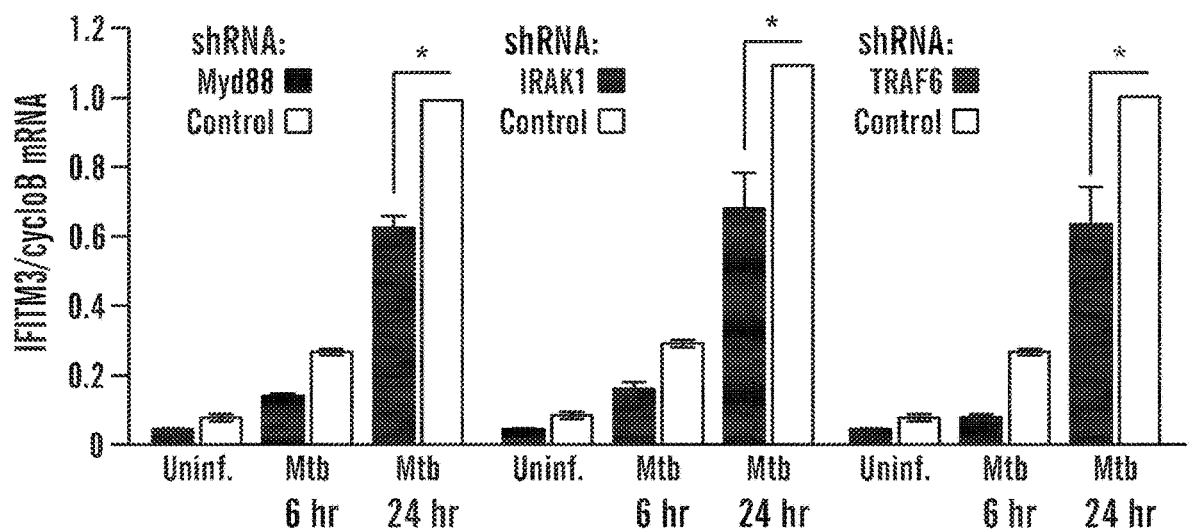
Figure 13B:
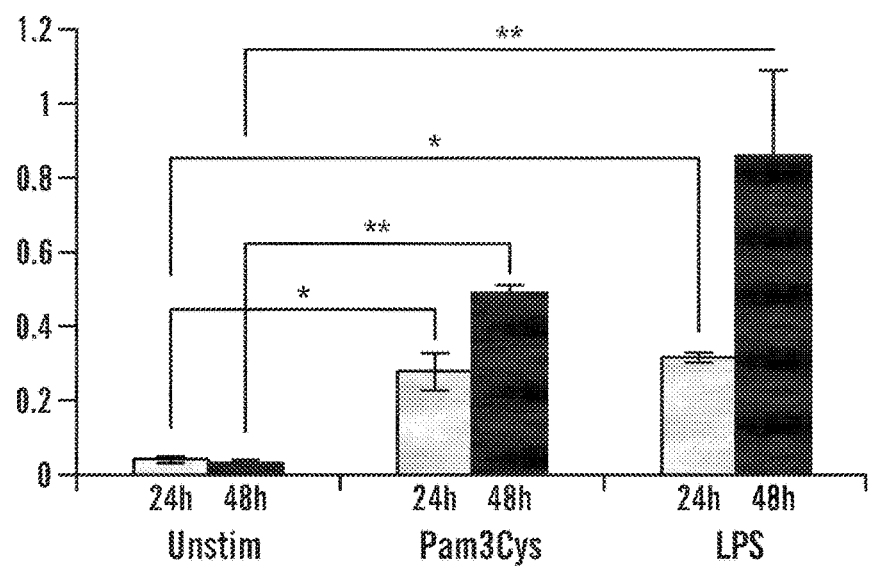

FIGS. 13A-13B show that IFITM3 mRNA expression is partially dependent upon MyD88, IRAK1, and TRAF6, but is not induced independently by the TLR2, MCP-1, or TNF signaling pathways. (FIG. 13A) THP-1 cells transduced with vectors expressing shRNA targeting MyD88, IRAK1, or TRAF6 and THP-1 cells transduced with a control shRNA were left uninfected or infected with MTb for 6 or 24 hours as indicated. (FIG. 13B) THP-1 cells were stimulated with Pam3Cys (4 µg/mL) or LPS (1 µg/mL) or left unstimulated for 24 or 48 hrs and IFITM3 mRNA was measured. Levels of IFITM3 mRNA normalized to levels of cyclophilin B mRNA in all cases. *=$p<0.05$; ***=$p<0.001$.

Figure 14A:
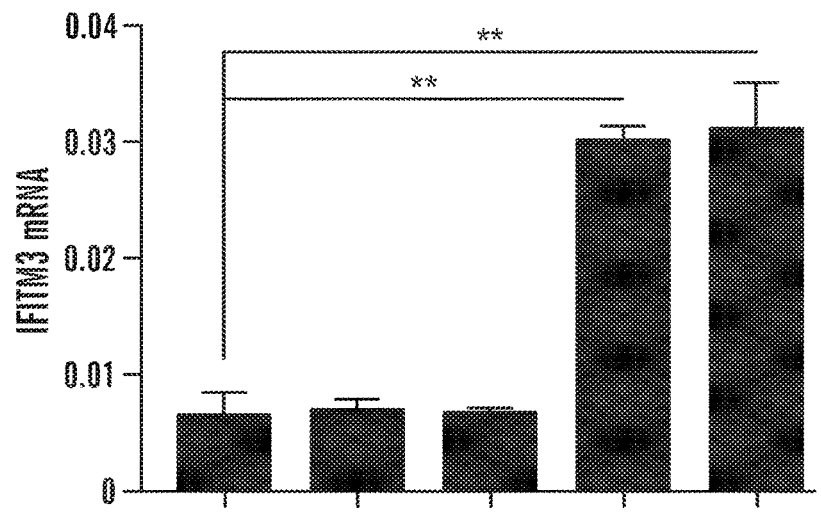
Figure 14B:
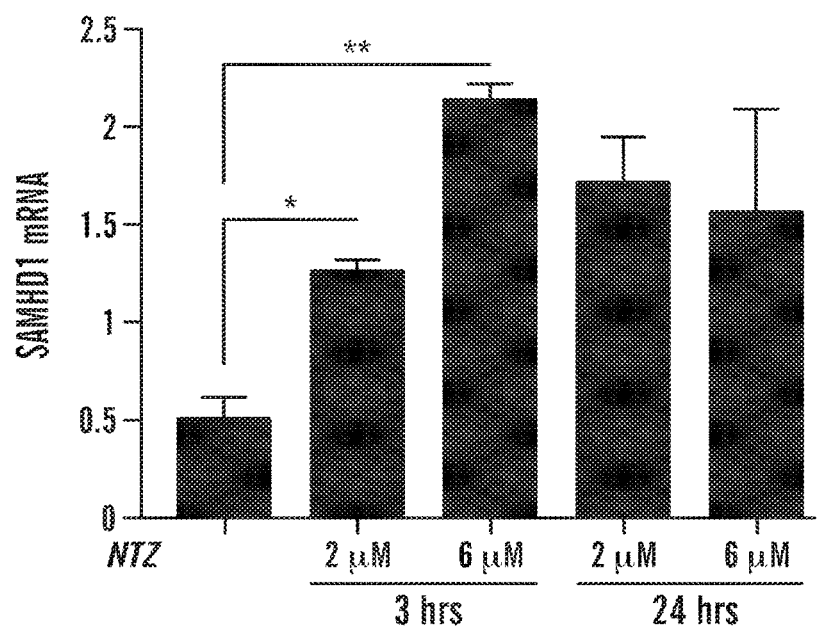

FIGS. 14A-14B show NTZ induction of IFITM3 and SAMDH1. MDM treated with the indicated amounts of NTZ were harvested after 3 or 24 hours and analyzed for IFITM3 (FIG. 14A) or SAMDH1 (FIG. 14B) mRNA expression. *=$p<0.05$; **=$p<0.01$.

Figure 15A:
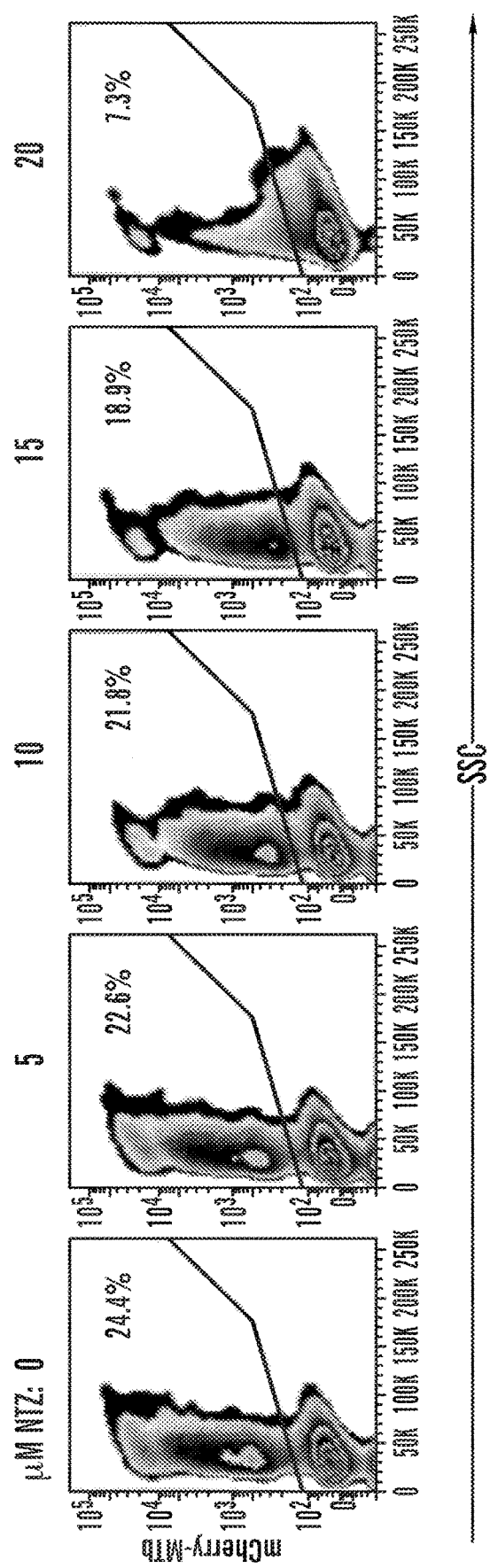
Figure 15B:
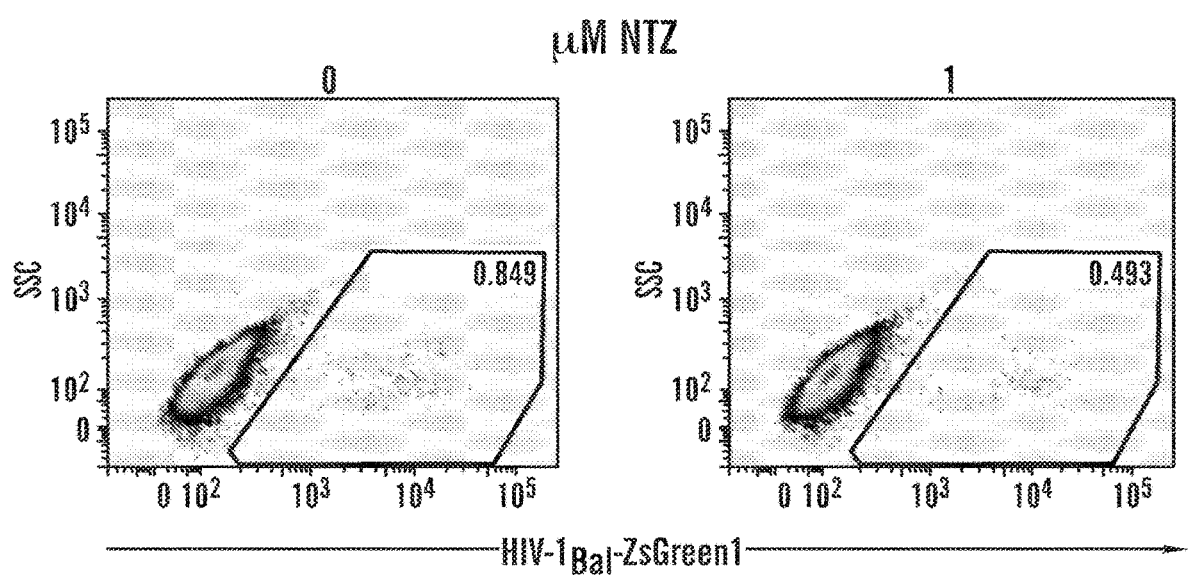

FIGS. 15A-15B NTZ inhibits MTb growth and HIV replication. (FIG. 15A) FACS analysis of THP-1 cells infected with H37Rv-mCherry MTb pretreated with 0, 5, 10, 15, or 20 µM NTZ. Percentages of MTb-infected (mCherry+) cells are shown. (FIG. 15B) FACS analysis of MDM infected with HIV-1Bal/ZsGreen1 pre-treated with 0 or 1 µM NTZ for 30 min. Percentages of HIV-1 infected cells (ZsGreen+) are shown.

Figures 17A, 17B:
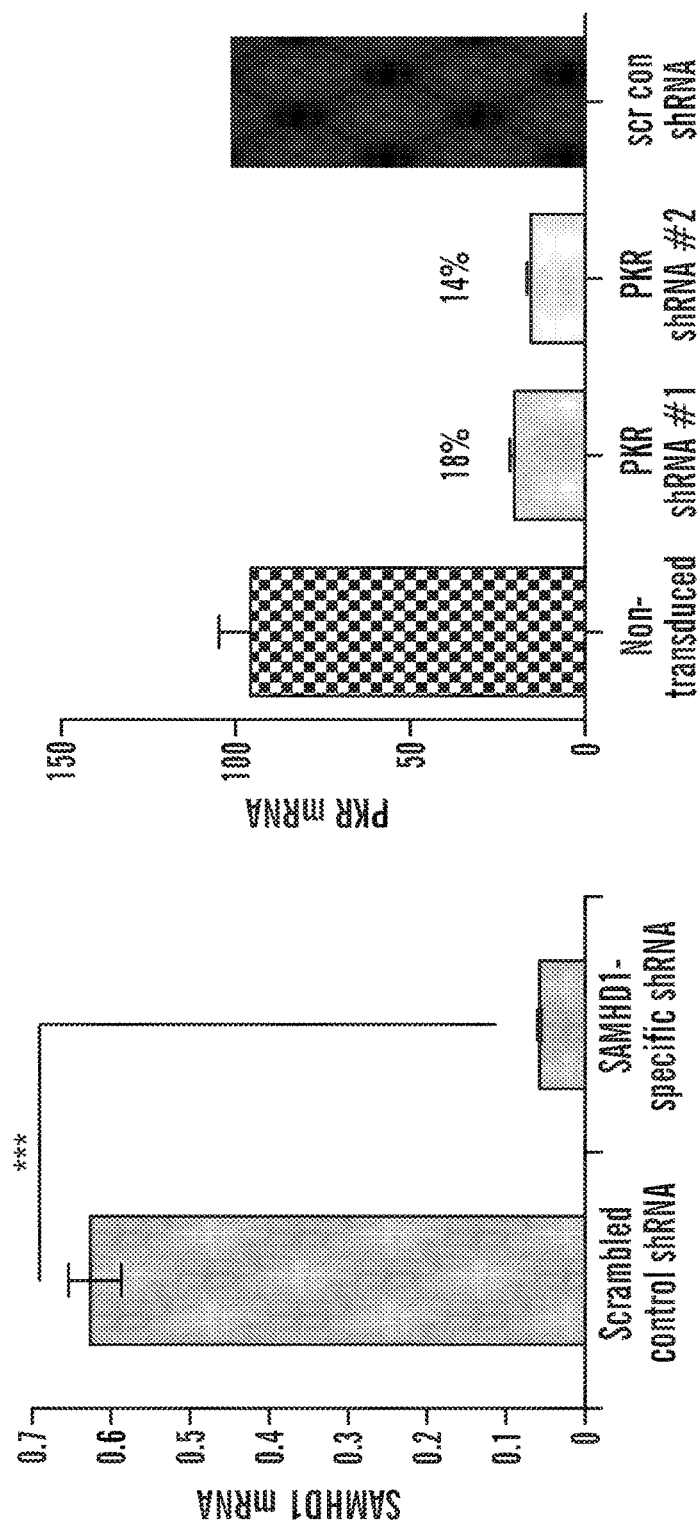

FIGS. 16A-16C show NTZ inhibits HIV LTR-mediated transcription. (FIG. 16A) Diagram of the "mini" HIV subtype C provirus integrated into THP-1 cells to create THP1/LTR-ZRT clones. (FIG. 16B) and C. THP-1/LTR/ZRT cells were treated with NTZ at 5 or 10 µM for 30 min, and NTZ-treated, untreated, and DMSO-treated (vehicle control) cells were then stimulated with (FIG. 16B) 200 ng/mL of Pam3Cys (P3C) or (FIG. 16C) 300 HA units/mL Sendai virus (SV) for 16 hrs. Levels of *Renilla* luciferase in relative light units (RLU) were normalized to firefly luciferase. *=$p<0.05$ FIGS. 17A-17B show that THP-1 cells were transduced with lentiviruses encoding scrambled control shRNA or shRNAs targeting (FIG. 17A) the SAMHD1 coding region or (FIG. 17B) two targets in the PKR coding region. SAMHD1 mRNA was normalized to cyclophilin B mRNA and PKR mRNAs were normalized to cyclophilin B mRNA followed by normalization to PKR mRNA levels in scrambled control shRNA-transduced cells. *=$p<0.001$ FIGS. 18A-18C NTZ treatment leads to stress granule formation. (FIG. 18A) NTZ induces stress granule formation in A549 cells. A549 cells were mock-treated or treated with sodium arsenite (0.5 µM) for 1 hr or NTZ (40 µM) for 4 hrs. Stress granules were detected after fixation and permeabilization with Rb anti-G3BP1 and DyLight-594-anti-Rb IgG antibodies. (FIG. 18**B) GADD34 transcription is induced by NTZ in A549 cells. A549 cells were treated with NTZ (40 µM) for the indicated lengths of time. RNA was then extracted and after oligoDT-based cDNA synthesis, GADD34 mRNA levels were measured by qPCR and normalized to cyclophilin B mRNA levels. Mean and SD of 3 independent experiments; *=$p<0.05$. (FIG. 18C) NTZ treatment of THP-1 cells results in increased cellular acidification. THP-1 cells were treated for 24 hrs with the indicated concentrations of NTZ (or IFN-beta as a positive control) and then stained with Lysotracker Red and analyzed by flow cytometry.

Figure 19A:
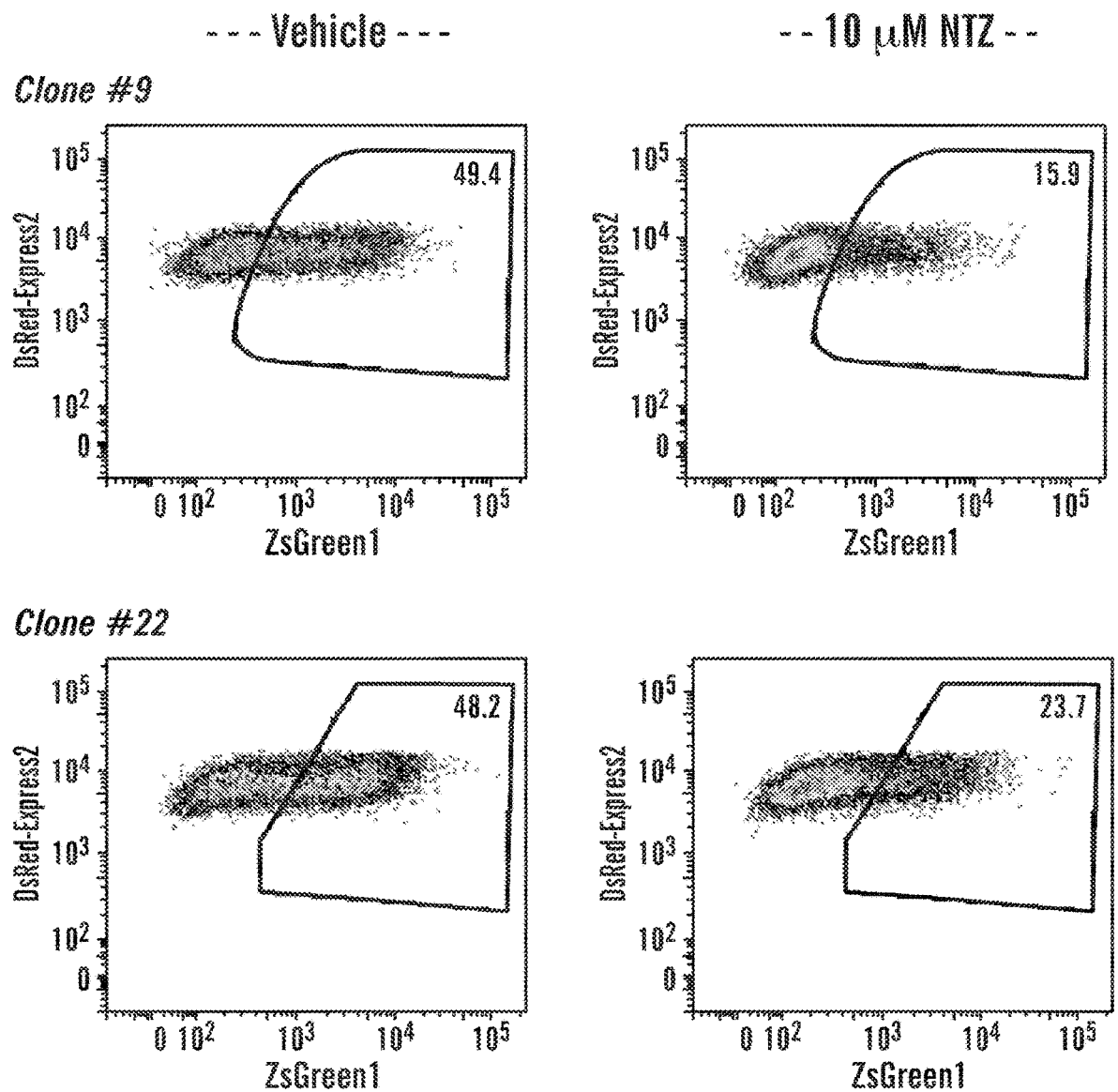
Figure 19B:
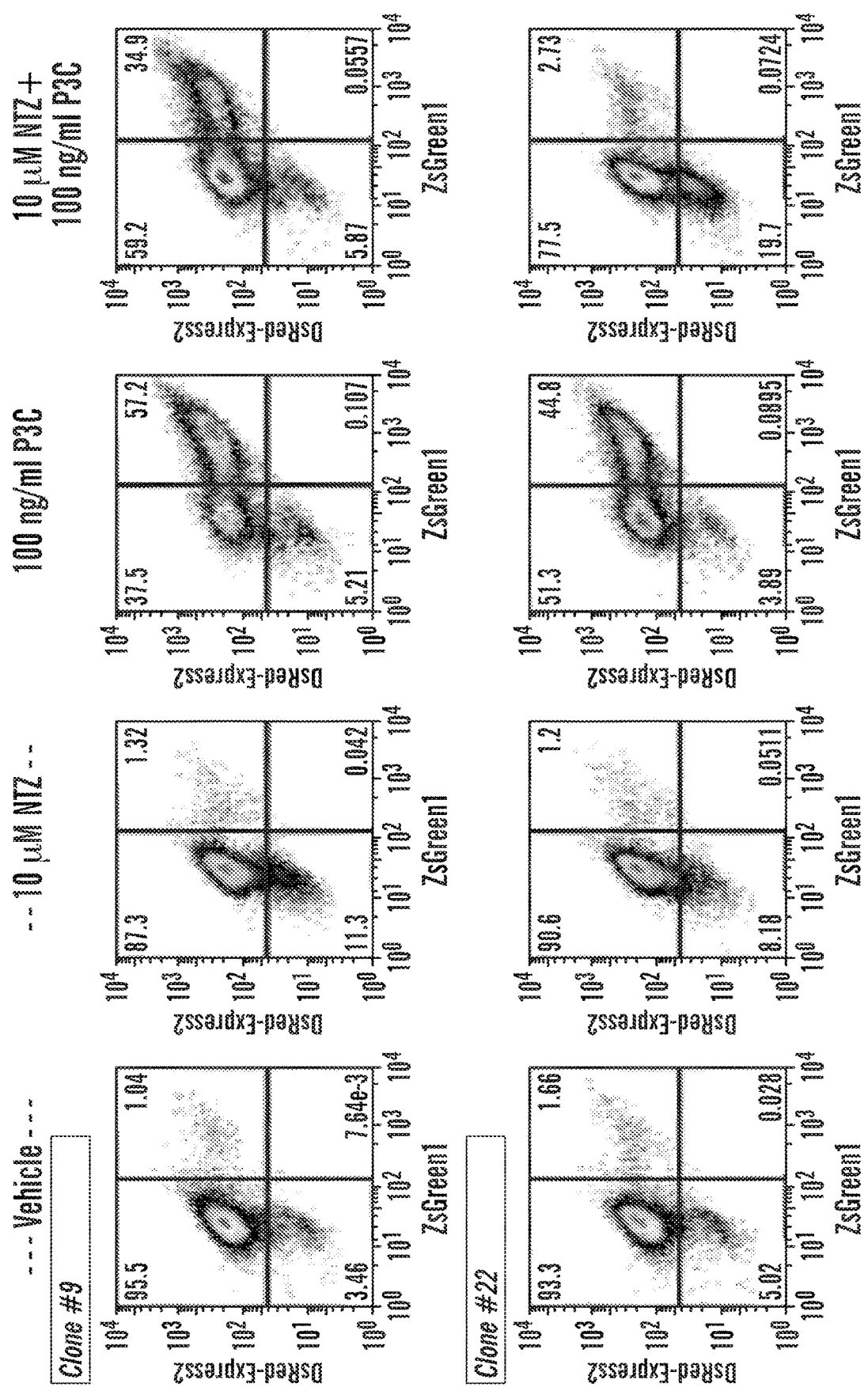

FIGS. 19A-19B (FIG. 19A) MTb-induced activation of latent HIV transcription is not enhanced by NTZ co-treatment. THP-1 cells with integrated HIV subtype C "mini" proviral genomes encoding ZsGreen1 (clone 9 and clone 22 indicate different integration sites) were infected with MTb and, after 6 hours, cells were analyzed by FACS to ascertain the level of HIV reactivation as measured by the induction of ZsGreen1 expression. (FIG. 19B) The latent THP-1 clones described above were stimulated with the TLR2 agonist Pam3Cys (P3C) in the presence or absence of 10 µM NTZ and then analyzed by FACS after 6 hrs to measure the level of LTR reactivation.

DETAILED DESCRIPTION

The invention is based, in part, on the discovery that nitazoxanide (NTZ) can increase the expression level of one or more IFITM proteins. Human IFITM proteins include IFITM1, IFITM2, IFITM3, and IFITM5. IFITM proteins have previously been shown to restrict *ebolavirus* and *marburgvirus* infection at an early post-entry step (Brass et al., Cell. 2009 Dec. 24; 139(7):1243-54; Huang et al., PLoS Pathog. 2011 Jan. 6; 7(1):e1001258). IFITM3 has also been shown to be critical in host restriction of dengue virus, the causative agent of dengue hemorrhagic fever (Brass et al., Cell. 2009 Dec. 24; 139(7):1243-54; Zhu et al., Cell Microbiol. 2015 January; 17(1):105-18), influenza virus (Brass et al., Cell. 2009 Dec. 24; 139(7):1243-54), and HIV (Lu et al., Journal of Virology, March 2011, p. 2126-2137 Vol. 85, No. 5), as well as other pathogenic enveloped viruses (reviewed in Perriera et al., Journal of Molecular Biology Volume 425, Issue 24, 13 Dec. 2013, Pages 4937-4955). Accordingly, various aspects and embodiments of the invention are related to the treatment of a disease that is treatable by increasing the expression level of one or more IFITM proteins in the subject.

Specifically, it was discovered that NTZ inhibits infection by *Zaire Ebolavirus* glycoprotein (GP)-pseudotyped lentiviral particles in human monocytes (THP-1 cells), human primary monocyte-derived macrophages (MDM), and human epithelial alveolar cells (A549 cells). Additionally, NTZ was also found to inhibit live Ebola virus in A549 cells tested. NTZ can thus be used either alone or in combination with other active agents to treat or prevent Ebola.

In one aspect, the technology described herein relates to a method of treating or preventing a disease that is treatable by increasing the expression level of one or more IFITM proteins in the subject, the method comprising administering a pharmaceutical composition comprising a therapeutically-effective amount of nitazoxanide or a related thiazolide to a subject in need thereof. The disease can be a result of viral or bacterial infection. In some embodiments, the infection can be inhibited by IFITM proteins. In some embodiments, the disease is causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*. *Marburgvirus* is a filovirus, and dengue virus belongs to a distinct family of viruses called Flaviviridae. And thus it is contemplated that any filovirus or a member of Flaviviridae can be treated by the method described herein.

It was also discovered that NTZ inhibits HIV reactivation in latently HIV infected human monocytes. Additionally NTZ was discovered to reduce LTR activation and not promote general inflammation in these cells upon bacterial infection and in response to TLR2 agonist. Accordingly, in one aspect, the technology described herein relates to a method of reducing the likelihood of an active recrudescent HIV infection in a subject, wherein the infection has become latent, the method comprising administering to the subject a therapeutically-effective amount of NTZ.

The IUPAC name for NTZ is [2-[(5-nitro-1,3-thiazol-2-yl)carbamoyl]phenyl] ethanoate. NTZ can be administered in a variety of routes. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The administration can be systemic or local. NTZ is sold under the brand names Nizonide, Nitaxide, Nitax, Zox, Netazox, Niazid, Toza, Daxon, Dexidex, Kidonax, Mitafar, Pacovanton, Paramix, Alinia, Adonid, NT-TOX, Nitamax, and Annita.

It is contemplated that derivatives or analogues of NTZ can be used in the methods described herein. Derivatives of NTZ are disclosed, for example, in US20130317070, US20060194853, and CN103070876 (see Table1). Non-limiting examples of derivatives of NTZ include compounds of formula I, Ia, Ib, Ic, Id, Ie, If, Ig, Ih, II, IIa, IIb, IIc, IId, III, IIIa, IIIb, IIIc, IIId, IIIe, IIIf, IIIg, IIIh, IIIi, IIIj, IV, Iva, IVb, IVc, IVd, V, Va, Vb, Vc, Vd, VI, VIa, VIb, VIc, VId, VPC 161180, VPC161183, VPC162047, VPC162080, VPC162087, VPC162088, VPC16a1011, VPC16a1060, VPC16b1089, VPC16b1090, VPC16b1092, VPC16b1093, and VPCb1094 as referenced in US20130317070, Compound C, compound D, compound E, or compound G as referenced in US2006019485.

NTZ is a prototypical member of a class of compounds termed "thiazolides". Romark Labs is currently investigating additional related compounds, including one derivative of NTZ referred to as "RM-5038". RM-5038 shows improved activity against *Cryptosporidium parvum* infection in gerbils as compared to NTZ (Gargala et al, AAC, 2013), has similar efficacy to NTZ in hepatitis B and C in vitro models (Korba et al, Antiviral Res, 2008; Stachulski et al, J. Med Chem, 2011a and b), and has been reported to be better absorbed than NTZ in the GI tract and better tolerated over 28-day dosing of dogs and rats (Rossignol, Antiviral Res, 2014). Active metabolites of NTZ include tizoxanide (TIZ) (see, e.g., Korba et al Antiviral Res, 2008; Rossignol, J B C, 2009; Ashton, Vet Med Int, 2010; and La Frazia et al, J. Virol, 2013) and tizoxanide glucuronide. It is contemplated that tizoxanide and/or tizoxanide glucuronide can be administered to advantage against viral infections as described herein for NTZ and its derivatives.

In some embodiments, the pharmaceutical composition comprising NTZ optionally comprises a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g., NTZ.

The pharmaceutical compositions can be specially formulated for administration in solid, liquid or gel form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally the compounds described herein can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, the pharmaceutical composition comprising NTZ can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of NTZ are well known to those skilled in the art. Examples include, without limitation: sterile water; water for injection USP; saline solution; glucose solution; aqueous vehicles such as but not limited to, sodium chloride injection, Ringer's injection, dextrose injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of NTZ can also be incorporated into the parenteral dosage forms of the disclosure, including conventional and controlled-release parenteral dosage forms.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, NTZ can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B 1;

each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, NTZ can be administered in a liposome formulation. As used herein, "lipid vesicle" or "liposome" refers to vesicles surrounded by a bilayer formed of lipid components usually including lipids optionally in combination with non-lipidic components. The interior of a vesicle is generally aqueous. One major type of liposomal composition not generally found in nature includes phospholipids other than naturally-derived phosphatidylcholine. Neutral lipid vesicle compositions, for example, can be formed from dimyristoyl phosphatidylcholine (DMPC) or dipalmitoyl phosphatidylcholine (DPPC). Anionic lipid vesicle compositions generally are formed from dimyristoyl phosphatidylglycerol. Another type of liposomal composition is formed from phosphatidylcholine (PC) such as, for example, soybean PC, and egg PC. Another type is formed from mixtures of phospholipid and/or phosphatidylcholine and/or cholesterol. Lipids for lipid vesicle or liposome formation are known in the art or described herein below. Liposomes are formed by the self-assembly of phospholipid molecules in an aqueous environment. The amphipathic phospholipid molecules form a closed bilayer sphere in an attempt to shield their hydrophilic groups from the aqueous environment, while still maintaining contact with the aqueous phase via the hydrophilic head group. The resulting closed sphere can encapsulate aqueous soluble drugs or agents such as the hemoglobin, enzyme and cofactor compositions described herein, within the bilayer membrane. Non-limiting examples of liposome compositions include those described U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556, each of which is incorporated herein by reference in its entirety.

In some embodiments, NTZ can be administered in an oral formulation. NTZ is commercially available in two oral dosage forms—tablet (500 mg) and oral suspension (100 mg per 5 ml when reconstituted). Examples of oral dosage forms include, but are not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms are prepared by combining the pharmaceutically acceptable salt of the disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents. Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary.

For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent. Examples of excipients that can be used in oral dosage forms of NTZ include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used to form pharmaceutical compositions and dosage forms of the disclosure include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

The term "effective amount" as used herein refers to the amount of a therapy needed to alleviate at least one or more symptoms of the disease or disorder, and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

In some embodiments, the pharmaceutical composition is administered to a subject in need thereof in accordance with the method described herein at a dosage and a frequency of administration that achieves one or more of the following: (i) decreases the production or concentration of viral RNA or DNA or viral protein or the production or activity of a virus induced cytopathic effect; (ii) decreases the viral titer of a subject or an animal model with a viral infection; (iii) reduces or ameliorates the severity of the viral infection and/or one or more symptoms associated therewith in a subject with the viral infection; (iv) reduces the number of symptoms and/or the duration of one or more symptoms associated with the viral infection in a subject with the viral infection; (v) prevents the onset, progression or recurrence of one or more symptoms associated with the viral infection in a subject with the viral infection; (vi) inhibits or reduces viral replication or the production or concentration of viral RNA or DNA or viral protein or the production or activity of a virus induced cytopathic effect associated with the viral infection in a subject or an animal model; and/or (vii) enhances or improves the therapeutic efficacy of another antiviral therapy in a subject with the viral infection or an animal model.

In some embodiments, the pharmaceutical composition is administered to a subject in accordance with the method described herein once a day or several times a day (e.g., twice a day, three times a day, or four times a day). In some embodiments, the pharmaceutical composition is administered to a subject in accordance with the method described herein once, twice, three times, or four times every other day (i.e., on alternate days), once, twice, three times, or four times every two days, once, twice, three times, or four times every three days, once, twice, three times, or four times every four days, once, twice, three times, or four times every 5 days, once, twice, three times, or four times a week, once, twice, three times, or four times every two weeks, once, twice, three times, or four times every three weeks, once, twice, three times, or four times every four weeks, once, twice, three times, or four times every 5 weeks, once, twice, three times, or four times every 6 weeks, once, twice, three times, or four times every 7 weeks, or once, twice, three times, or four times every 8 weeks. In some embodiments, the pharmaceutical composition is administered to a subject in accordance with the method described herein in cycles, wherein the pharmaceutical composition is administered for a period of time, followed by a period of rest (i.e., the pharmaceutical composition is not administered for a period of time).

The dosage can be determined by one of skill in the art and can also be adjusted by the individual physician in the event of any complication. Typically, the dosage of a pharmaceutical composition comprising NTZ can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, or from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, or from 4.5 g/kg body weight to 5 g/kg body weight. Effective doses may be extrapolated from dose-response curves derived from in vitro or animal model test bioassays or systems. The dosage should not be so large as to cause unacceptable adverse side effects.

In some embodiments, the therapeutically-effective amount of nitazoxanide is in the range of 100-3000 milligrams per day. In some embodiments, the therapeutically-effective amount of nitazoxanide is in the range of 200-3000 milligrams per day. In some embodiments, the therapeutically-effective amount of nitazoxanide is in the range of 200-2000 milligrams per day. In some embodiments, the therapeutically-effective amount of nitazoxanide is in the range of 200-1000 milligrams per day. In some embodiments, the therapeutically-effective amount of nitazoxanide is in the range of 200-500 milligrams per day.

In some embodiments, NTZ is the sole therapeutically-effective ingredient used in the method described herein. That is, in such embodiments, when the method described herein is used to treat a subject in need thereof, NTZ is the only antiviral agent administered to the subject.

In some embodiments, the method further comprises administering one or more therapeutically-effective ingredients other than NTZ for treating the disease. In some embodiments, NTZ is administered in combination with one or more other antiviral agents. Examples of antiviral agents that can be used in combination with NTZ include, but are not limited to, entry inhibitor, fusion inhibitor, helicase inhibitor, ribavirin, a ribavirin analogue, ribavirin and at least one or more of a nonpegylated interferon or a pegylated interferon, a TLR agonist, cyclophilin inhibitor, caspase or pancaspase inhibitor, immunomodulator, immunomodulator/antiinflammatory, antiinflammatory, antiinflammatory/antifibrotic, broad spectrum immune stimulator, antifibrotic, antioxidant, hemopurifier, IMPDH inhibitor, glycosidase inhibitor, glucosidase inhibitor, HIV inhibitor, RNA inhibitor, RNAi, anti-phospholipid therapy, protein therapeutic, interferon replacement agent, botanical or non-specific pharmaceutical.

Currently, no specific antiviral agents for treating Ebola, marburgvirus infection, or dengue virus infection have been approved. Experimental antiviral drugs being tested on Ebola patients include, but are not limited to, Brincidofovir and ZMapp™. Examples of drugs for treating HIV infection include, but are not limited to, non-nucleoside reverse transcriptase inhibitors, nucleoside analogue reverse transcriptase inhibitors (e.g., zidovudine, tenofovir, lamivudine, or emtricitabine). Examples of drugs for treating tuberculosis include, but are not limited to, antibiotics such as isoniazid and rifampicin.

In some embodiments, NTZ is administered in combination with one or more broad spectrum antibiotic or antiparasitic agents that have been shown to have some efficacy against the particular disease being treated. For example, for Ebola treatment, the broad spectrum antibiotic or antiparasitic agent can be chloroquine. See, e.g., Madrid et al., PLOS One 2013, 8, e60579 for a systematic screen of FDA-approved drugs for inhibitors of biological threat agents.

In some embodiments, the method described herein can be used to treat a subject having HIV infection and tuberculosis.

Ebola, marburgvirus infection, dengue virus infection, HIV infection, and tuberculosis can be diagnosed using methods known in the art. For example, Ebola can be diagnosed by isolating the virus, detecting its RNA or proteins, or detecting antibodies against the virus in a person's blood. Symptoms of Ebola include, but are not limited to, fatigue, fever, weakness, decreased appetite, muscle pain, joint pain, headache, sore throat, and vomiting.

In one aspect, the technology described herein relates to a method of increasing the expression level of a protein in a cell selected from the group consisting of an IFITM protein, protein kinase R (PKR), and retinoic acid-inducible gene 1 (RIG-I), the method comprising contacting the cell with nitazoxanide. Increased expression can be detected and measured by methods known to those of skill in the art and include, e.g., assays depending upon antibody binding to the target protein (e.g., ELISA, western Blot, or other immunoassay), assays based on nucleic acid amplification (e.g., RT-PCR, microarray analyzer), assays that measure bioactivity (e.g., via the target protein's effect on a reporter or marker in a bioassay).

In some embodiments, the IFITM protein is selected from the group consisting of IFITM1, IFITM2, IFITM3, and IFITM5.

In some embodiments, the contacting is in vitro.

In some embodiments, the contacting is in vivo.

Stress granules form in response to stress conditions, including pathogen infection and other environmental stressors. They are repositories for translationally stalled mRNA-ribonucleoprotein complexes that can rapidly initiate completed translation once the stress is relieved (Onomto K. et al, 2014). PKR is a factor directly implicated in stress granule pathway. NTZ has been demonstrated to induce PKR phosphorylation and PKR-mediated eIF2α phosphorylation (Ashiru, O. et. al. 2014) indicating that NTZ can lead to formation of stress granules. Accordingly, in one aspect of the invention described herein relates to a method of inducing formation of stress granules and/or cellular acidity in a cell.

PKR is one factor that has been directly implicated in the stress granule pathway, and evidence suggests that stress granules nucleated by the cytoplasmic factors G3BP1, G3BP2, and Caprin-1, form a platform for PKR activation (Reineke, L C. et al, 2015). In turn, active PKR phosphorylation of eIF2a enhances global protein synthesis downregulation and the assembly and maintenance of stress granules (Okonski, K M. et al, 2013, Yoo, J S. et. al, 2014, Zhang, P. et al, 2014). Of the genes that remain capable of being activated during eIF2α-induced translational shutdown, the phosphatase GADD34 is of major importance. GADD34 transcriptional activation is regulated by ATF4, which is directly activated by phosphorylated eIF2α (Ma, Y. et al. 2003, Novoa, I. et al. 2001). GADD34 is a phosphatase that functions in an auto-regulatory loop by dephosphorylating eIF2α leading to the resumption of translation and ATF4/GADD34 downregulation unless the stressor persists (Ma, Y. et al. 2003, Novoa, I. et al. 2001, Ruggieri, A. et al. 2012, Rojas, M. 2015). In some embodiments, the method described herein is used to increase the expression levels of GADD34 and/or phosphorylation of eIF2α.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although any known methods, devices, and materials may be used in the practice or testing of the invention, the methods, devices, and materials in this regard are described herein.

Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein the term "comprising" or "comprises" is used in reference to compositions, methods, and respective component(s) thereof, that are useful to an embodiment, yet open to the inclusion of unspecified elements, whether useful or not.

As used herein the term "consisting essentially of" refers to those elements required for a given embodiment. The term permits the presence of elements that do not materially affect the basic and novel or functional characteristic(s) of that embodiment of the invention.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein the term "in need thereof" means having a disease, being diagnosed with a disease, or being in need of preventing a disease. A subject in need thereof can be a subject in need of treating or preventing a disease.

As used herein, the terms "treat," "treatment," "treating," or "amelioration" refer to therapeutic treatments, wherein the object is to reverse, alleviate, ameliorate, inhibit, slow down or stop the progression or severity of an infectious disease, e.g., Ebola. The term "treating" includes reducing or alleviating at least one adverse effect or symptom of an infectious disease. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized, or the progression of Ebola is slowed or halted. The term "treatment" of a disease also includes providing relief from the symptoms or side-effects of the disease (including palliative treatment).

As used herein, the term "prevent" or "prevention" refers to stopping, hindering, and/or slowing down the onset and/or development of calcification in an infectious disease. In one embodiment, "prevent" is synonymous with "inhibit".

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, or intralesional.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples.

The terms "increased", "increase", or "enhance" are all used herein to generally mean an increase by a statically significant amount; for the avoidance of doubt, the terms "increased", "increase", or "enhance", mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In some embodiments, the reference level is the expression level of an IFITM protein in a subject who does not take NTZ.

The terms "decrease", "reduce", "reduction", or "inhibit" are all used herein generally to mean a decrease by a statistically significant amount. For example, "decrease", "reduce", "reduction", or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. In the context of a marker or symptom is meant a statistically significant decrease in such level. The decrease can be, for example, at least 10%, at least 20%, at least 30%, at least 40% or more, and is preferably down to a level accepted as within the range of normal for an individual without a given disease.

The term "statistically significant" or "significantly" refers to statistical significance and generally means a difference of two standard deviations (2SD) or more.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material necessary or used in formulating an active ingredient or agent for delivery to a subject. Each carrier must be "acceptable" in the sense of being compatible with the other ingredients of the formulation and not injurious to the patient.

As used herein, the term "in combination" refers to the use of more than one prophylactic and/or therapeutic agent simultaneously or sequentially and in a manner that their respective effects are additive or synergistic.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Embodiments of various aspects described herein can be defined in any of the following numbered paragraphs:

1. A method of treating a disease comprising administering a pharmaceutical composition comprising a therapeutically-effective amount of nitazoxanide to a subject having the disease, wherein the disease is causally linked to infection by one or more pathogens selected from the group consisting of members of the genus

*Ebolavirus*, members of the genus *Marburgvirus*, members of the species dengue virus, human immunodeficiency viruses 1 and 2, and members of the species *Mycobacterium tuberculosis*.
2. A method of preventing a disease comprising administering a pharmaceutical composition comprising a therapeutically-effective amount of nitazoxanide to a subject in need thereof, wherein the disease is causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*.
3. The method of paragraph 1 or 2, wherein the disease is causally linked to infection by one or more pathogens selected from the group consisting of members of the genus *Ebolavirus*, members of the genus *Marburgvirus*, members of the species dengue virus, and human immunodeficiency viruses 1 and 2.
4. The method of any one of paragraphs 1-3, wherein the pharmaceutical composition comprises nitazoxanide as the sole therapeutically-effective ingredient.
5. The method of any one of paragraphs 1-3, wherein the pharmaceutical composition comprises nitazoxanide in combination with another therapeutically-effective ingredient.
6. The method of any one of paragraphs 1-5, wherein the therapeutically-effective amount of nitazoxanide is in the range of 200-3000 milligrams per day.
7. The method of any one of paragraphs 1-6, wherein the administering is oral.
8. The method of any one of paragraphs 1-7, wherein the subject is a mammal.
9. The method of any one of paragraphs 1-8, wherein the subject is a human.
10. The method of any one of paragraphs 1-9, wherein the subject has tuberculosis and HIV infection.
11. A method of reducing the likelihood of an active recrudescent HIV infection in a subject, wherein the infection has become latent, the method comprising administering to the subject a therapeutically-effective amount of nitazoxanide.
12. A method of increasing expression level of a protein in a cell selected from the group consisting of an interferon-induced transmembrane (IFITM) protein, protein kinase R (PKR), retinoic acid-inducible gene 1 (RIG-I) and growth arrest and DNA damage-inducible protein (GADD34), the method comprising contacting the cell with nitazoxanide.
13. The method of paragraph 12, wherein the IFITM protein is selected from the group consisting of IFITM1, IFITM2, IFITM3, and IFITM5.
14. A method of inducing anti-viral stress response in a cell, the method comprising contacting the cell with nitazoxanide.
15. The method of paragraph 14, wherein the anti-viral stress response is formation stress granules and/or increase in cellular acidity.
16. A method of increasing phosphorylation of eIF2α in a cell, the method comprising contacting the cell with nitazoxanide.
17. The method of any one of paragraphs 12-16, wherein the contacting is in vitro.
18. The method of any one of paragraphs 12-16, wherein the contacting is in vivo.
19. The method of paragraph 18, wherein the in vivo contacting is done in a mammal.
20. The method of paragraph 18, wherein the mammal is a human.
21. Use of nitazoxanide for the treatment of a disease causally linked to infection by one or more pathogens selected from the group consisting of members of the genus *Ebolavirus*, members of the genus *Marburgvirus*, members of the species dengue virus, human immunodeficiency viruses 1 and 2, and members of the species *Mycobacterium tuberculosis*.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1: Anti-*Ebolavirus* Effects of NTZ

It was discovered herein that NTZ induces the transcriptional activation of IFITM3, a member of the IFN-inducible transmembrane (IFITM) family. Members of this family, which include IFITM1, 2, and 3, have been shown to restrict ebolavirus and marburgvirus infection when overexpressed, and IFNβ suppression of infection by both viruses is partially reversed by simultaneous knockdown IFITM1+IFITM3 (3). A non-replicating ebolavirus model system is utilized to demonstrate that NTZ pre-treatment of THP-1 monocytes significantly impedes entry of ZE-LV particles. Without wishing to be bound by theory, NTZ is thought to inhibit ebolavirus infection through induction of IFITM family member expression and overcomes viral interference with the host antiviral response. A single lentiviral vector encoding catalytically inactive Cas9 linked to the kruppel-associated box (KRAB) repressive domain and multiple unique guide RNAs is used to individually and combinatorially repress IFITM1, 2, and 3 induction in THP-1 cells to determine the contributions of these host proteins to NTZ's anti-ebolavirus effects. In separate experiments this approach is used to repress double-stranded RNA (dsRNA)-activated protein kinase (PKR) expression. Use of this approach can permit one to overcome the strong block of RNA interference pathways mediated by the ebolavirus viral protein 35 (VP35) and thus ensure ablation of these genes. Finally, by combining a focused investigation of the role of IFITM family members in NTZ's anti-ebolavirus activity with a global, RNA-seq-based approach to determine changes in coding and non-coding RNA synthesis that occur in human macrophages in response to NTZ, *Zaire ebolavirus*, or NTZ+*Zaire ebolavirus*, robust detection of host mechanisms critical for NTZ's antiviral effects and host responses that have been subverted by ebolavirus infection can be ensured—information that is useful for developing new host-based therapies, and providing the scientific underpinning for repurposing NTZ for treatment of ebolavirus infection.

IFITM family members are small (~15 kD) membrane-associated proteins that are expressed constitutively in numerous tissues (except for IFITM5, which is mainly expressed in bone) (5-7). Expression of IFITMs 1-3 is strongly induced by type I IFN treatment, and both IFITMl and IFITM3 can be induced by IFN-γ (8-12). IFITMs were originally associated with IFN-induced suppression of tumor cell growth (13, 14). Recently, their roles in viral infection have come to light. Initially shown to inhibit influenza virus, vesicular stomatitis virus (VSV), West Nile virus, and dengue virus, in cell culture (15), more recent studies have implicated one or more of the IFITM family members in restriction of lentiviruses, bunyaviruses, filoviruses, paramyxoviruses, reoviruses, and coronaviruses as well (3, 16-20). IFITM2 and IFITM3 are primarily associated with late endosomes and lysosomes, while IFITM1 has also been detected at the plasma membrane (21-24). It is becoming increasingly apparent that the IFITMs block viral envelope-host cell membrane fusion at a step that occurs after fusion initiates. For example, influenza virus hemagglutinin undergoes a conformational change upon exposure to the increasingly acidic environment found in the late endosome, triggering fusion and release of viral components into the cytoplasm (25). IFITM3, which potently inhibits influenza virus infection, appears to block fusion pore formation after viral hemagglutin-endosomal membrane hemifusion (26), and all three IFITMs have been found to interfere with productive fusion of viral envelope proteins with host cell membranes (27).

The ebolavirus GP mediates fusion of the viral envelope with the late endosomal lipid bilayer upon its cleavage by the acidic endopeptidases cathepsin B and/or cathepsin L (28-31), although other endosomal proteases can likely compensate for absence of these cathepsins in vivo (32). Farzan and colleagues found that overexpression of each of the IFITM family members inhibits *Zaire ebolavirus* infection in several different cell lines (3). Moreover, shRNA-mediated knockdown experiments indicated that IFITM3 and IFITM1 are the major IFITM family members involved in restricting *Zaire ebolavirus* infection of HeLa cells after IFNβ pre-treatment (3). Based on IFITM3's actions influenza virus infection, it can be speculated that fusion of ebolavirus GP with endosomal membranes is blocked by IFITMs at a step following acidification of the compartment and cathepsin B/L cleavage. Intriguingly, once monocytes begin to differentiate to macrophages, constitutive IFITMl-3 levels steadily decline, and this corresponds to increased susceptibility to *Zaire ebolavirus* infection (33). Moreover, *Zaire ebolavirus* infection of undifferentiated monocytes also inhibits expression of the IFITMs, suggesting that the virus actively works to reduce the impact of these host restriction factors in target cells. *Ebolavirus* viral protein 35 (VP35) is a potent inhibitor of dsRNA-triggered antiviral responses, including type I IFN production, which is major inducer of IFITM expression.

Figure 1C:
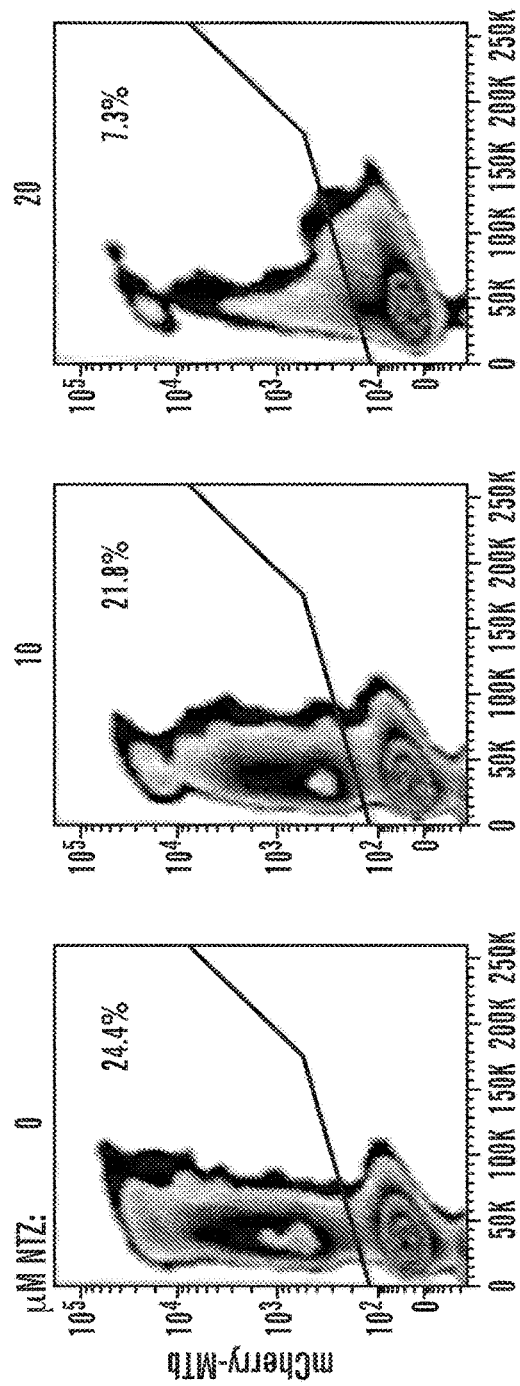
Figure 1D:
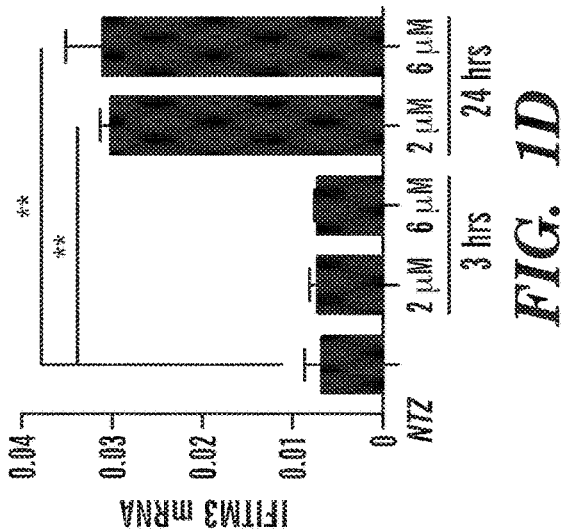

The role of IFN-induced host factors in controlling *Mycobacterium tuberculosis* (MTb) and HIV infections has been investigated. It was discovered that IFITM3 plays a key role in restriction of MTb infection as knockdown of IFITM3 (FIG. 1A) significantly enhances MTb infection in THP-1 cells (FIG. 1B). In parallel experiments, it was also discovered that the small molecule drug NTZ, which was first approved by the FDA in 2004 for the treatment of both *Giardia*- and *Cryptosporidium*-associated diarrhea (34), and has been used safely in an estimated 5 million patients, including those who are HIV-positive (35, 36), potently inhibits MTb infection of THP-1 cells in a concentration-dependent manner (FIG. 1C). Based on these findings, IFITMs may play a role in NTZ's anti-MTb activity. NTZ induces IFITM3 mRNA synthesis (FIG. 1D) and IFITM1 gene expression (data not shown) in human macrophages. These data suggest that NTZ-dependent upregulation of IFITM family member expression likely contributes to its ability to block MTb infection.

Figure 2A:
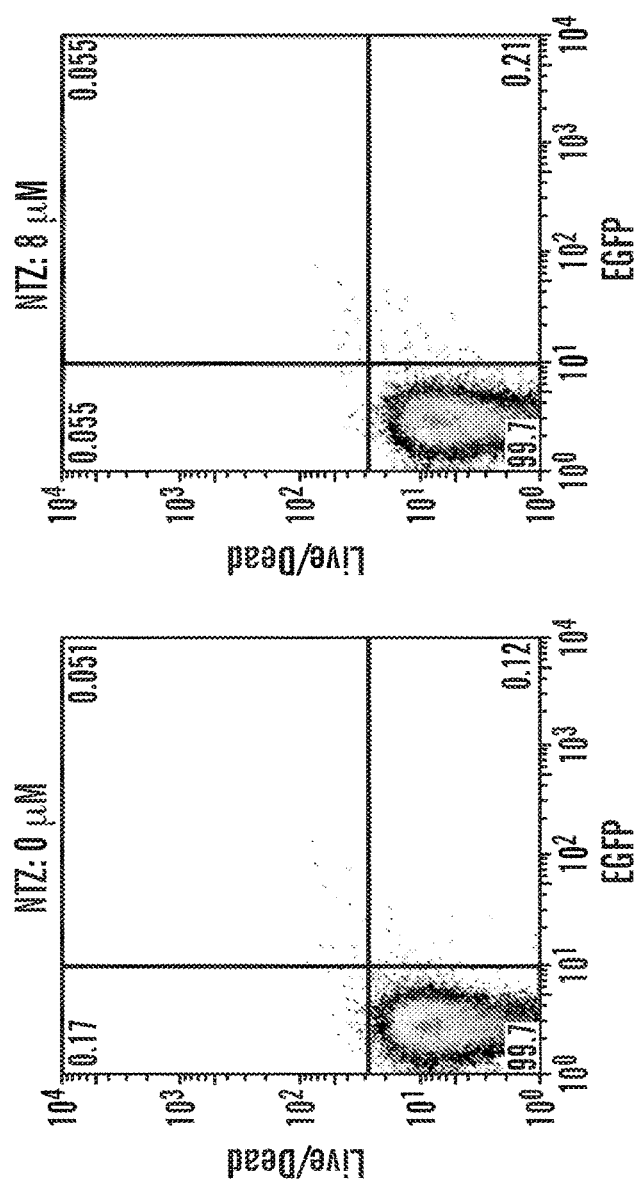
Figure 2B:
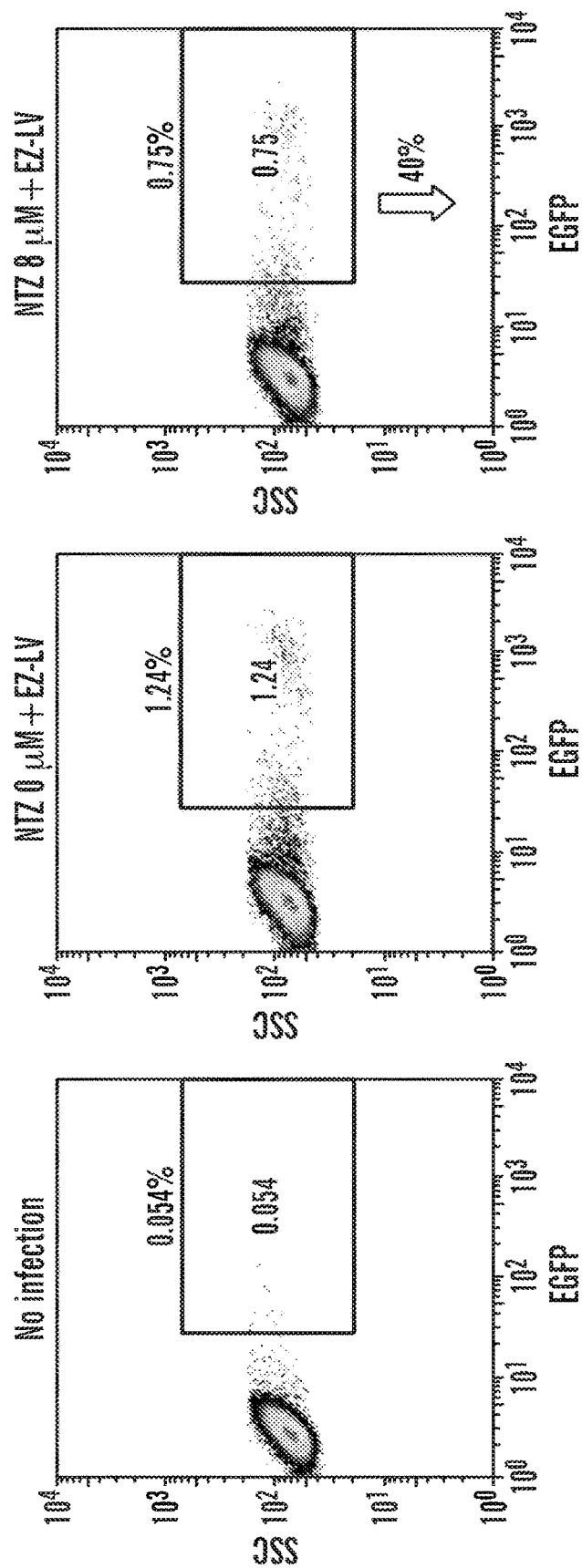

NTZ may have a suppressive effect on ebolavirus infection. It has been demonstrated that pre-treatment of THP-1 cells with 8 μM NTZ, which is well below peak mean plasma concentrations 26 μM of the active NTZ metabolite tizoxanide after a 500 mg dose of NTZ (37), shows no toxicity (FIG. 2A) and inhibits ZE-LV infection by ~40% (FIG. 2B). Because THP-1 cells share many characteristics of circulating monocytes, the effects of NTZ on ebolavirus infection of this cell type may in fact be reduced as compared to macrophages, which express lower constitutive levels of endogenous IFITMs. The effects of NTZ on ZE-LV infection are tested in human primary MDM, and on live *Zaire ebolavirus* infection of THP-1 cells and MDM.

Without wishing to be bound by theory, NTZ-mediated inhibition of ebolavirus infection may depend on this drug's ability to induce the transcription of IFITMs. The relative importance of IFITM1, IFITM2, and IFITM3 in the inhibition of ZE-LV infection is investigated in undifferentiated THP-1 cells and PMA-differentiated THP-1 macrophages. Macrophages are a major in vivo target of ebolavirus, and activation of these antigen-presenting cells results in proinflammatory mediator production and local tissue damage (38, 39). The role of PKR activation by NTZ in the induction of IFITM gene expression and suppression of ZE-LV infection is determined. And the ability of NTZ to overcome the potent block on type I IFN production and the antiviral response imposed by VP35 is determined. This analysis can be extended to the global transcriptome of macrophages treated with NTZ, or infected with *Zaire ebolavirus* in the presence or absence of NTZ. CRISPR-Cas9-based gene deletion studies can be performed to determine the true relevance of observed transcriptional differences on NTZ antiviral activity and, more generally, *Zaire ebolavirus* infection. In summary, these experiments elucidate the major cellular mechanisms underlying NTZ's anti-ebolavirus activity. Such information is useful in repurposing NTZ for ebolavirus treatment and for drug discovery aimed at identifying secondary reagents that target host factors that may synergize with NTZ in blocking ebolavirus infection.

Figure 3A:
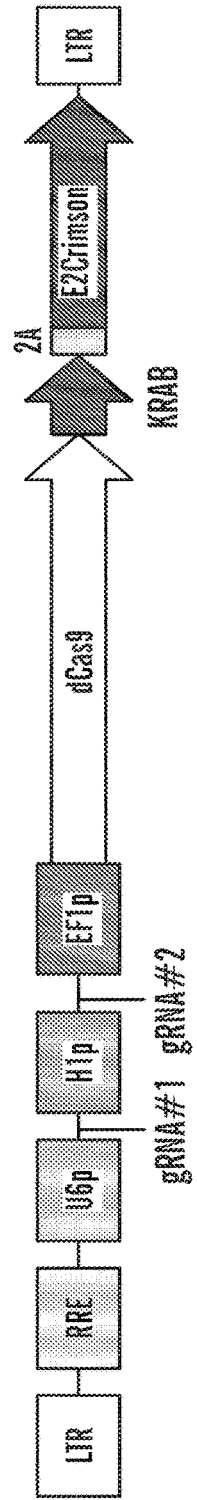
Figure 3B:
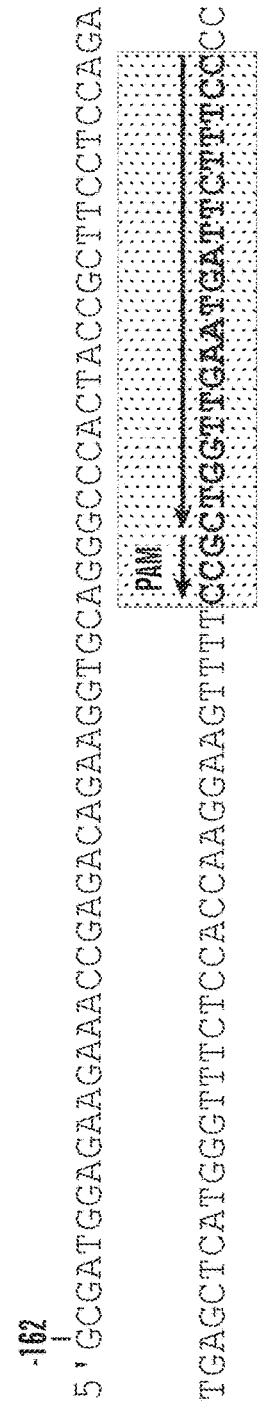
Figure 3B:
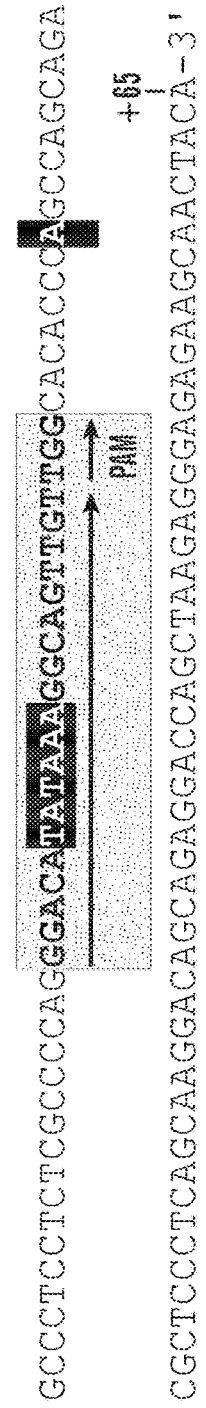

Impact of CRISPR/Cas9-Mediated IFITM Family Member Depletion on NTZ Inhibition of *Ebolavirus* Infection While siRNA and shRNA approaches are useful for gene knockdown under many circumstances, these approaches have several limitations. First, gene knockdown rarely ablates expression >80-90%, and this is especially the case with highly inducible genes like the IFITM family members. Second, there is concern that in monocyte/macrophages, which are highly sensitive to foreign dsRNA, use of siRNA or shRNA to knockdown target genes may nonspecifically activate type I IFN responses (40). Such nonspecific effects would be highly problematic for investigating the roles of IFN-inducible genes in NTZ-mediated ebolavirus inhibition. Finally, ebolavirus VP35 is a strong inhibitor of RNAi, can block shRNA-mediated knockdown of unrelated genes, and interacts with the Dicer partners PACT and TRBP (41, 42). A lentiviral vector has been constructed in which the catalytically inactive form of Cas9 (termed "dead" Cas9 or dCas9) is fused to the KRAB domain, and is expressed along with one or more distinct guide RNAs from unique pol III promoters. In addition, the transcript that encodes dCas9-KRAB also encodes the far-red E2-Crimson reporter, which is released from dCas9-KRAB during translation through ribosomal stuttering at a 2A sequence (FIG. 3A). E2-Crimson expression allows for facile sorting and enrichment of cells that constitutively express the CRISPR components. This system has been used to abrogate LPS-induced TNF gene expression in THP-1 cells. Specifically, when guide RNAs specific to the TATAA box and flanking sequence in the TNF core promoter (FIG. 3B) are expressed in combination with dCas9-KRAB in THP-1 cells, LPS activation of TNF gene expression is knocked down >98% as compared to THP-1 cells expressing dCas9-KRAB and guide RNAs with no human genome sequence identity (FIG. 3C—left panel). No effect is seen on the LPS-induced 1L6 gene, demonstrating the specificity of this approach (FIG. 3C—right panel).

To investigate the importance of IFITM1, IFITM2, and IFITM3 in mediating NTZ's anti-ebolavirus effects, a panel of guide RNAs specific to the IFITM1, IFITM2, and IFITM3 promoters is tested using the above lentiviral system. The promoters of these genes contain clearly defined interferon-sensitive response elements (ISREs), as well as conserved binding sites for C/EBP and Ets transcription factors. Unique guide RNAs that individually abrogate IFN13-induced expression of IFITM1, IFITM2 or IFITM3 in THP-1 cells are identified. As controls, expression of the non-targeted IFITMs (i.e. IFITM2 and IFITM3 expression in the presence of an IFITM1-specific guide RNA), as well as the expression of the IFN-induced gene ISG15 is quantified. Cells are transduced with two control lentiviruses that encode unique guide RNAs containing at least 3 mismatches with any human genomic sequence. Cells are enriched by FACS after transduction and only used if >95% E2-Crimsont Once specific guide RNAs that ablate expression of each IFITM by >90% are identified, lentiviruses that encode all combinations of two guide RNAs (i.e., guides specific to IFITM1+IFITM2) and a lentivirus encoding all three guide RNAs are constructed. Single guide RNAs are expressed from the U6 pol III promoter, two guides from the U6 and H1 pol III promoters, and three guides from the U6, H1, and 7SK promoters. As shown in FIG. 3D, it has been functionally demonstrated that the ability of a single lentivirus encoding wild-type Cas9 and two guides RNAs driven by the U6 and H1 promoters, respectively, to homozygously delete a 325 bp region in the INF/LT locus in THP-1 cells, clearly showing that strong expression of both guide RNAs is driven by the tandem pol III promoters in this system.

To determine the roles of the three IFITMs in NTZ's anti-ebolavirus effects, including any redundancy, THP-1 cells expressing dCas9-KRAB and the single or multiple IFITM-specific guide RNA(s), or control guide RNAs, are mock-treated or treated with NTZ at 5, 10 or 20 µM (or, as a positive control, 1 nM recombinant IFNβ for 8 or 24 hours, and then infected with ZE-LV particles as shown in FIG. 2. After addition of GP-lentiviral particles and mixing, cells are centrifuged at 500×g for 30 minutes, incubated at 37 C/5% $CO_2$ for 4 days, and then subjected to flow cytometry to measure EGFP$^+$ cells.

PMA-differentiated THP-1 cells are much more susceptible to ebolavirus infection than nondifferentiated THP-1 cells, which correspond to a drop in IFITMI-3 levels (33). To determine if NTZ has a greater effect on ebolavirus infection in PMA-differentiated THP-1 cells, the same control and guide RNA-IFITM-targeted THP-1 cells are differentiated toward a macrophage-like phenotype with 100 nM PMA (Sigma) for 24 hours prior to NTZ/IFNβ treatment and infection with ZE-LV (no spinoculation) as described above. IFITM1-3 levels at the time of infection and in response to NTZ treatment are also measured by qRT-PCR and western blotting to compare their expression in differentiated versus undifferentiated THP-1 cells, and ZE-LV infection are analyzed by flow cytometry after four days.

Role of PKR in NTZ-Mediated Inhibition of *Ebolavirus* Infection

Although very little is known about cellular targets of NTZ, an intriguing study found that NTZ directly induces the autophosphorylation of PKR in hepatoma cells (44). PKR activation amplifies the IFN response by: i) activating the NF-κB, p38, JNK, and STAT1/3 pathways, resulting in transcription of antiviral response genes such as those encoding IFNβ and TNF (45); and by ii) suppressing general mRNA translation via phosphorylation and inhibition of eIF2α (46-48). Because type I IFNs are potent activators of IFITM expression, and the NF-κB pathway has been implicated in both IFITM1 and IFITM3 gene activation (49, 50), it is hypothesized that NTZ inhibition of ebolavirus infection depends, at least in part, on PKR activation.

The ability of NTZ to activate PKR is first established in the THP-1 cells and in human monocyte-derived macrophages (MDM). For MDM, monocytes are isolated from peripheral blood by magnetic selection (StemCell Technologies) and differentiated with GM-CSF (50 ng/ml) for six days. Cells are treated with 0, 2, 6, or 10 µM of NTZ for 30, 60, or 120 minutes and then processed for western blotting with antibodies directed against total PKR and PKR that is phosphorylated at threonine 451, which is the primary PKR autophosphorylation target residue (51) (Millipore). Next, three complementary avenues are pursued to directly elucidate the role of PKR in NTZ-mediated inhibition of ebolavirus infection. First, THP-1 cells in which PKR gene activation is ablated are generated using the CRISPR/dCas9-KRAB technology, and PKR-deficient THP-1 cells will be treated with NTZ at 0, 10 or 20 µM (or 1 nM recombinant IFNβ for 4, 8, or 24 hours, and IFITM1-3 levels are measured. Second, control or PKR-deficient cells (with or without prior PMA differentiation) are infected with ZE-LV after NTZ or IFNβ treatment and, after four days, infection is monitored by flow cytometry. Third, human MDM are treated with the specific PKR inhibitors C16 (Sigma) or 2-aminopurine for 30 min, followed by NTZ for 30 min, and are then infected with ZE-LV at 4 or 8 hrs post-treatment. EGFP level is monitored by flow cytometry. Findings in support of a role for NTZ-activated PKR in control of ZE-LV infection can be validated with live *Zaire ebolavirus* infection.

Ability of NTZ to Overcome Ebola Virus VP35-Mediated Inactivation of Double-Stranded RNA Responses Viral protein 35 (VP35) of ebolavirus, which potently inhibits IFN induction in infected cells (52-54), has been shown to block PKR autophosphorylation and eIF2α phosphorylation (55, 56). VP35, is also a major component of the viral replication/transcription nucleocapsid complex (57, 58), binds strongly to dsRNA (59-62), both coating the dsRNA molecule and covering the dsRNA blunt ends that are pattern recognition receptor triggers (62, 63). Although a major focus of research on VP35 suppression of IFN responses has been on its role in blocking RIG-I and IRF3 activation (43, 54, 60, 64-66), the interaction between VP35 and dsRNA likely also contributes to its ability to inhibit PKR activation.

Normally, PKR autophosphorylation occurs only after the enzyme binds to dsRNA, which triggers its autophosphorylation (67, 68). The reported ability of NTZ to directly induce autophosphorylation of PKR (44), however, suggests that NTZ may overcome VP35-mediated inhibition of PKR activation by bypassing the requirement for detectable dsRNA to activate PKR. To investigate this possibility, the following approaches are employed. First, THP-1 cells will be transduced with a pLKO.1 lentiviral expression vector in which the SV40 promoter drives the constitutive expression of a C-terminal Flag-tagged *Zaire ebolavirus* i) wild-type VP35 protein or ii) VP35 protein containing K319A and R322A substitutions, which disrupt VP35-dsRNA interaction but have no impact on VP35 contribution to viral replication/transcription (69). Cells are selected with puromycin and strong expression of VP35-Flag and VP35 (KRA)-Flag are validated by flag-tag western blotting. Next, cells are treated with NTZ at 0, 5, 10 or 20 µM (or, as a control to stimulate high levels of dsRNA to confirm VP35 function in this system, cells will be infected with Sendai virus) for 4, 8, or 24 hours. Next, PKR activation are measured as described previously, and cell supernatants are collected and IFNβ protein are measured by ELISA (Pierce) to quantitate the activity of NTZ on the innate antiviral response over and above repression of this response mediated by VP35. Finally, to determine if NTZ remains effective at ZE-LV infection in the context of VP35 overexpression, the VP35-Flag and VP35(KRA)-Flag THP-1 cells (with or without PMA differentiation) are infected after pre-treatment with 0, 5, 10 or 20 µM of NTZ for 4, 8, or 24 hours. Infection levels are determined by flow cytometry of EGFP expression.

Characterization of Gene Expression Profiles in NTZ+/− *Ebolavirus*-Infected Primary Human Macrophages In spite of the paucity of data on immune correlates of survival versus death in *Zaire ebolavirus* patients, it is clear that impaired T cell immunity, with concomitant dysregulated innate inflammation, is a hallmark of poor outcome. In the first days following symptomology, transient increases in circulating TNF, IL-6, and IL-1β correspond to survival, but continued increases in these proinflammatory cytokines over the next 2-3 days precede death, indicating that a regulated balance of innate mediator production is critical for host control of disease (70-73). At the same time, massive T cell lymphopenia, accompanied by Fas/CD95 surface expression in the T cell compartment, is associated with fatal outcome (73).

Although IFITMs are anticipated to play a major role in NTZ's inhibitory effects on ebolavirus infection, it is likely that additional factors induced by NTZ also contribute to its activity. At another level, NTZ may induce changes in host gene expression that are unrelated to the innate antiviral response, but that are of critical importance for other processes such as adaptive immunity that play a major role in vivo. Although very little is known about cellular targets of NTZ other than PKR, NTZ has been shown to suppress MTb proliferation in cell cultures by inhibiting the mammalian target of rapamycin (mTOR) pathway, leading to activation of autophagy (74). Autophagy has been linked to the control of a number of viral infections (75), but its role in ebolavirus infection has not been studied.

Figure 4:
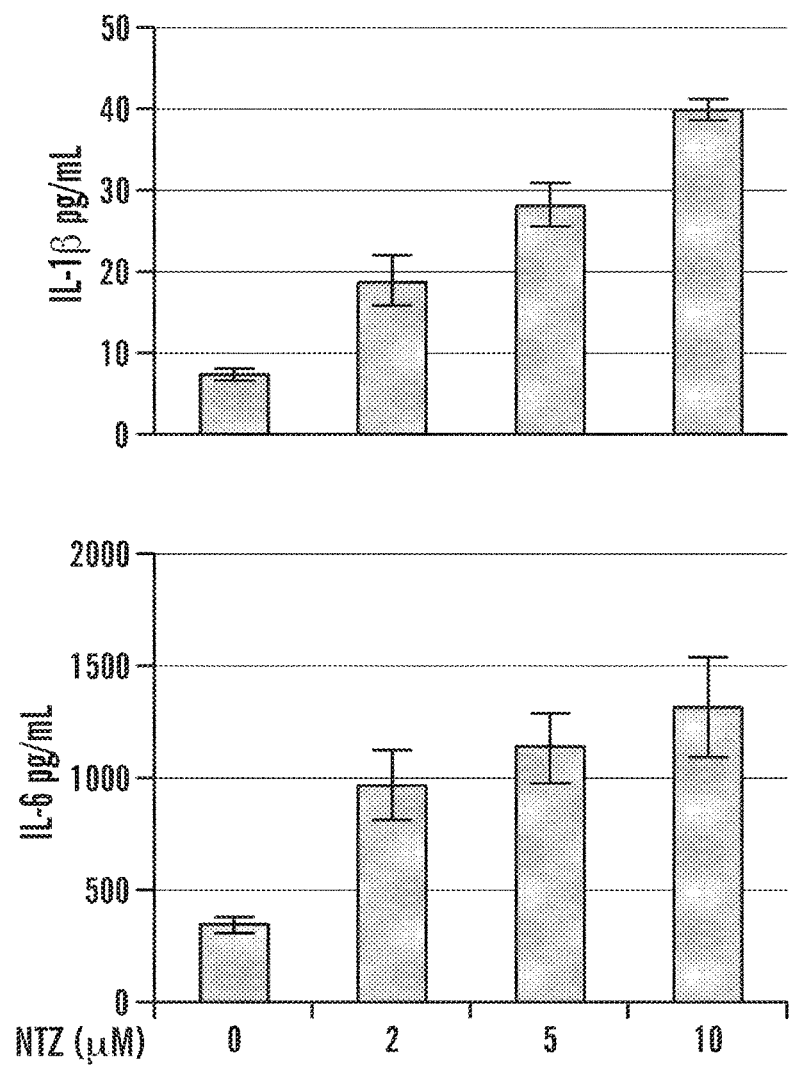

The data examining NTZ's effect on the innate immune system demonstrate that NTZ induces the expression and release of IL-β and IL-6 in human PBMC (FIG. 4), while TNF, IL-2, IL-4, IL-8, IL-10, and IFN-γ, were not affected. Because a key function both IL-β and IL-6 is to promote antigen-specific T cell activation and memory responses (76-79), this finding suggests that prophylactic treatment with NTZ may also enhance ebo/avirus-specific T cell immunity during the first days post-infection. A more global approach is necessary to get a deeper understanding of NTZ's effects and to detect novel regulatory pathways that cannot be predicted a priori. Whole transcriptome analysis of human macrophages in response to NTZ treatment, *Zaire ebolavirus* infection, or dual NTZ+*Zaire ebolavirus*, may reveal patterns of coding and non-coding RNA changes that correspond to i) viral suppression by this FDA-approved small molecule, and ii) induction of regulatory pathways that either modulate or enhance innate immune activity. Analysis of select transcripts in THP-1 cells using CRISPR/Cas9 technology is performed. These experiments can provide important insights into how NTZ affects the transcriptional program in primary macrophages, which play a critical role during ebolavirus infection. These experiments can also elucidate NTZ-mediated changes in gene expression that are sustained during ebolavirus infection and associated with viral inhibition, which is of immediate value as biomarkers of clinical response as this FDA-approved compound is repurposed for treatment of ebolavirus infection.

Measurement of Changes in the Whole Transcriptome in Human Macrophages in Response to NTZ, *Ebolavirus*, and NTZ+*Ebolavirus*

To date, studies of ebolavirus's effects on global gene expression have relied on microarray-based assays. These analyses have revealed that several pathways, including apoptotic, cell adhesion, and innate inflammatory pathways, are triggered upon *Zaire ebolavirus* infection of liver cell lines (80) and human macrophages (81). Although important, these studies were limited by the number of transcripts analyzed (13,000 genes), and their focus only on mRNA transcripts. The increasing realization that non-coding RNAs, in particular long non-coding RNAs play a critical role in gene regulation in immunity underscores the importance of measuring changes in these RNA species in addition to mRNA in order to obtain a fuller understanding of how infection and/or therapeutics affect a cell's transcriptional program (82).

To obtain a detailed picture of how NTZ and *Zaire ebolavirus* infection impact the full transcriptome in human macrophages, the following protocol can be used. Briefly, human MDM from three different healthy donors are i) left untreated; ii) treated with NTZ (10 µM) for 24 hours; iii) infected with *Zaire ebolavirus* (MOI: 0.5) for 24 hours; or iv) treated with NTZ for 4 hours and then infected with *Zaire ebolavirus* for 20 hours. Total RNA are prepared by Trizol extraction and ethanol precipitation, completely eliminating any infectious viral material. RNA are frozen and shipped to a facility where labeling and library preparation are performed (Agilent) and next gen sequencing are performed using, e.g., an Illumina HiSeq system. Data analysis focusing on transcripts that are differentially up- or down-regulated (>3-fold) by NTZ, ebolavirus, or NTZ+ebolavirus, are identified.

Impact of Candidate Transcripts Identified by RNA-Seq on NTZ Inhibition of *Ebolavirus* Infection The functional relevance of the RNA-seq data obtained is investigated. Transcripts that i) are upregulated or down-regulated >3-fold by NTZ in comparison to no treatment, and ii) are unaffected or only marginally affected by ebolavirus infection are focused on. This permits one to identify gene targets that can be regulated by NTZ even in the presence of the full complement of viral components, including VP35. First, the NTZ- and/or ebolavirus-induced changes detect by RNA-seq are reproduced in THP-1 cells by selected qRT-PCR analysis. Cas9-based disruption methods in THP-1 cells are employed to knock out expression of the target genes using a lentiviral vector encoding wild-type Cas9 in place of dCas9-KRAB, homozygous gene disruptions are validated by PCR, and clonal populations are expanded after single-cell sorting (see FIG. 3D). Next NTZ and *Zaire ebolavirus* challenges are performed on these cells to elucidate the impact of these genes on viral infection and NTZ's inhibitory activity on infection.

REFERENCES FOR EXAMPLE 1

1. Dhillon R S, Srikrishna D, Sachs J. Controlling Ebola: next steps. Lancet. 2014.
2. Gostin L O, Friedman E A. Ebola: a crisis in global health leadership. Lancet. 2014; 384(9951):1323-5.
3. Huang I C, Bailey C C, Weyer J L, Radoshitzky S R, Becker M M, Chiang J J, Brass A L, Ahmed A A, Chi X, Dong L, Longobardi L E, Boltz D, Kuhn J H, Elledge S J, Bavari S, Denison M R, Choe H, Farzan M. Distinct patterns of IFITM-mediated restriction of filoviruses, SARS coronavirus, and influenza A virus. PLoS Pathog. 2011; 7(1):e1001258.
4. Team WHOER. Ebola Virus Disease in West Africa—The First 9 Months of the Epidemic and Forward Projections. N Engl J Med. 2014.
5. Hickford D, Frankenberg S, Shaw G, Renfree M B. Evolution of vertebrate interferon inducible transmembrane proteins. BMC genomics. 2012; 13:155.
6. Siegrist F, Ebeling M, Certa U. The small interferon-induced transmembrane genes and proteins. J Interferon Cytokine Res. 2011; 31(1):183-97.
7. Moffatt P, Gaumond M H, Salois P, Sellin K, Bessette M C, Godin E, de Oliveira P T, Atkins G J, Nanci A, Thomas G. Bril: a novel bone-specific modulator of mineralization. J Bone Miner Res. 2008; 23(9):1497-508.
8. Reid L E, Brasnett A H, Gilbert C S, Porter A C, Gewert D R, Stark G R, Kerr I M. A single DNA response element can confer inducibility by both alpha- and gamma-interferons. Proc Natl Acad Sci USA. 1989; 86(3):840-4.
9. Lewin A R, Reid L E, McMahon M, Stark G R, Kerr I M. Molecular analysis of a human interferon-inducible gene family. Eur J Biochem. 1991; 199(2):417-23.
10. McKendry R, John J, Flavell D, Muller M, Kerr I M, Stark G R. High-frequency mutagenesis of human cells and characterization of a mutant unresponsive to both alpha and gamma interferons. Proc Natl Acad Sci USA. 1991; 88(24):11455-9.
11. Friedman R L, Manly S P, McMahon M, Kerr I M, Stark G R. Transcriptional and posttranscriptional regulation of interferon-induced gene expression in human cells. Cell. 1984; 38(3):745-55.
12. Kelly J M, Gilbert C S, Stark G R, Kerr I M. Differential regulation of interferon-induced mRNAs and c-myc mRNA by alpha- and gamma-interferons. Eur J Biochem. 1985; 153(2):367-71.
13. Yang G, Xu Y, Chen X, Hu G. IFITM1 plays an essential role in the antiproliferative action of interferon-gamma. Oncogene. 2007; 26(4):594-603.
14. Brem R, Oraszlan-Szovik K, Foser S, Bohrmann B, Certa U. Inhibition of proliferation by 1-8U in interferon-alpha-responsive and non-responsive cell lines. Cell Mol Life Sci. 2003; 60(6):1235-48.
15. Brass A L, Huang I C, Benita Y, John S P, Krishnan M N, Feeley E M, Ryan B J, Weyer J L, van der Weyden L, Fikrig E, Adams D J, Xavier R J, Farzan M, Elledge S J. The IFITM proteins mediate cellular resistance to influenza A H1N1 virus, West Nile virus, and dengue virus. Cell. 2009; 139(7):1243-54.
16. Zhang W, Zhang L, Zan Y, Du N, Yang Y, Tien P. Respiratory Syncytial Virus Infection is Inhibited by Interferon-Induced Transmembrane Proteins. The Journal of general virology. 2014.
17. Mudhasani R, Tran J P, Retterer C, Radoshitzky S R, Kota K P, Altamura L A, Smith J M, Packard B Z, Kuhn J H, Costantino J, Garrison A R, Schmaljohn C S, Huang I C, Farzan M, Bavari S. IFITM-2 and IFITM-3 but not IFITM-1 restrict Rift Valley fever virus. J Virol. 2013; 87(15):8451-64.
18. Anafu A A, Bowen C H, Chin C R, Brass A L, Holm G H. Interferon-inducible transmembrane protein 3 (IFITM3) restricts reovirus cell entry. J Biol Chem. 2013; 288(24):17261-71.
19. Chutiwitoonchai N, Hiyoshi M, Hiyoshi-Yoshidomi Y, Hashimoto M, Tokunaga K, Suzu S. Characteristics of IFITM, the newly identified IFN-inducible anti-HIV-1 family proteins. Microbes Infect. 2013; 15(4):280-90.
20. Lu J, Pan Q, Rong L, He W, Liu S L, Liang C. The IFITM proteins inhibit HIV-1 infection. J Virol. 2011; 85(5):2126-37.
21. John S P, Chin C R, Perreira J M, Feeley E M, Aker A M, Savidis G, Smith S E, Elia A E, Everitt A R, Vora M, Pertel T, Elledge S J, Kellam P, Brass A L. The CD225 domain of IFITM3 is required for both IFITM protein association and inhibition of influenza A virus and dengue virus replication. J Virol. 2013; 87(14):7837-52.
22. Amini-Bavil-Olyaee S, Choi Y J, Lee J H, Shi M, Huang I C, Farzan M, Jung J U. The antiviral effector IFITM3 disrupts intracellular cholesterol homeostasis to block viral entry. Cell Host Microbe. 2013; 13(4):452-64.
23. Feeley E M, Sims J S, John S P, Chin C R, Pertel T, Chen L M, Gaiha G D, Ryan B J, Donis R O, Elledge S J, Brass A L. IFITM3 inhibits influenza A virus infection by preventing cytosolic entry. PLoS Pathog. 2011; 7(10): e1002337.
24. Weston S, Czieso S, White I J, Smith S E, Kellam P, Marsh M. A membrane topology model for human interferon inducible transmembrane protein 1. PLoS One. 2014; 9(8):e104341.
25. Mair C M, Ludwig K, Herrmann A, Sieben C. Receptor binding and pH stability—how influenza A virus hemagglutinin affects host-specific virus infection. Biochimica et biophysica acta. 2014; 1838(4):1153-68.
26. Desai T M, Marin M, Chin C R, Savidis G, Brass A L, Melikyan G B. IFITM3 restricts influenza A virus entry by blocking the formation of fusion pores following virus-endosome hemifusion. PLoS Pathog. 2014; 10(4): e1004048.
27. Li K, Markosyan R M, Zheng Y M, Golfetto O, Bungart B, Li M, Ding S, He Y, Liang C, Lee J C, Grafton E, Cohen F S, Liu S L. IFITM proteins restrict viral membrane hemifusion. PLoS Pathog. 2013; 9(1):e1003124.
28. Bale S, Liu T, Li S, Wang Y, Abelson D, Fusco M, Woods V L, Jr., Saphire E O. Ebola virus glycoprotein needs an additional trigger, beyond proteolytic priming for membrane fusion. PLoS neglected tropical diseases. 2011; 5(11):e1395.
29. Brecher M, Schornberg K L, Delos S E, Fusco M L, Saphire E O, White J M. Cathepsin cleavage potentiates the Ebola virus glycoprotein to undergo a subsequent fusion-relevant conformational change. J Virol. 2012; 86(1):364-72.
30. Schornberg K, Matsuyama S, Kabsch K, Delos S, Bouton A, White J. Role of endosomal cathepsins in entry mediated by the Ebola virus glycoprotein. J Virol. 2006; 80(8):4174-8.
31. Chandran K, Sullivan N J, Felbor U, Whelan S P, Cunningham J M. Endosomal proteolysis of the Ebola virus glycoprotein is necessary for infection. Science. 2005; 308(5728):1643-5.

32. Marzi A, Reinheckel T, Feldmann H. Cathepsin B & L are not required for ebola virus replication. PLoS neglected tropical diseases. 2012; 6(12):e1923.
33. Martinez O, Johnson J C, Honko A, Yen B, Shabman R S, Hensley L E, Olinger G G, Basler C F. Ebola virus exploits a monocyte differentiation program to promote its entry. J Virol. 2013; 87(7):3801-14.
34. Hussar D A. New drugs of 2003. J Am Pharm Assoc (2003). 2004; 44(2):168-206; quiz 7-10.
35. Doumbo O, Rossignol J F, Pichard E, Traore H A, Dembele T M, Diakite M, Traore F, Diallo D A. Nitazoxanide in the treatment of cryptosporidial diarrhea and other intestinal parasitic infections associated with acquired immunodeficiency syndrome in tropical Africa. Am J Trop Med Hyg. 1997; 56(6):637-9.
36. Rossignol J F, Hidalgo H, Feregrino M, Higuera F, Gomez W H, Romero J L, Padierna J, Geyne A, Ayers M S. A double-'blind' placebo-controlled study of nitazoxanide in the treatment of cryptosporidial diarrhoea in AIDS patients in Mexico. Transactions of the Royal Society of Tropical Medicine and Hygiene. 1998; 92(6): 663-6.
37. Marcelin-Jimenez G, Contreras-Zavala L, Maggi-Castellanos M, Angeles-Moreno A P, Garcia-Gonzalez A. Development of a method by UPLC-M S/M S for the quantification of tizoxanide in human plasma and its pharmacokinetic application. Bioanalysis. 2012; 4(8): 909-17.
38. Martinez O. Leung L W, Basler C F. The role of antigen-presenting cells in filoviral hemorrhagic fever: gaps in current knowledge. Antiviral research. 2012; 93(3):416-28.
39. Ansari A A. Clinical features and pathobiology of *Ebolavirus* infection. Journal of autoimmunity. 2014.
40. Judge A D, Sood V, Shaw J R, Fang D, McClintock K, MacLachlan I. Sequence-dependent stimulation of the mammalian innate immune response by synthetic siRNA. Nature biotechnology. 2005; 23(4):457-62.
41. Fabozzi G, Nabel C S, Dolan M A, Sullivan N J. *Ebolavirus* proteins suppress the effects of small interfering RNA by direct interaction with the mammalian RNA interference pathway. J Virol. 2011; 85(6):2512-23.
42. Haasnoot J, de Vries W, Geutjes E J, Prins M, de Haan P, Berkhout B. The Ebola virus VP35 protein is a suppressor of RNA silencing. PLoS Pathog. 2007; 3(6):e86.
43. Luthra P, Ramanan P, Mire C E, Weisend C, Tsuda Y, Yen B, Liu G, Leung D W, Geisbert T W, Ebihara H, Amarasinghe G K, Basler C F. Mutual antagonism between the Ebola virus VP35 protein and the RIG-I activator PACT determines infection outcome. Cell Host Microbe. 2013; 14(1):74-84.
44. Elazar M, Liu M, McKenna S A, Liu P, Gehrig E A, Puglisi J D, Rossignol J F, Glenn J S. The anti-hepatitis C agent nitazoxanide induces phosphorylation of eukaryotic initiation factor 2alpha via protein kinase activated by double-stranded RNA activation. Gastroenterology. 2009; 137(5):1827-35.
45. Goldfeld A E, Maniatis T. Coordinate viral induction of tumor necrosis factor a and interferon b in human B cells and monocytes. Proceedings of the National Academy of Sciences USA. 1989; 86(5):1490-4.
46. Pindel A, Sadler A. The role of protein kinase R in the interferon response. Journal of interferon & cytokine research: the official journal of the International Society for Interferon and Cytokine Research. 2011; 31(1):59-70.
47. Kang R, Tang D. PKR-dependent inflammatory signals. Sci Signal. 2012; 5(247):pe47. Epub 2012/10/25.
48. Munir M, Berg M. The multiple faces of proteinkinase R in antiviral defense. Virulence. 2013; 4(1):85-9. Epub 2013/01/15.
49. Nakajima A, Ibi D, Nagai T, Yamada S, Nabeshima T, Yamada K. Induction of interferon-induced transmembrane protein 3 gene expression by lipopolysaccharide in astrocytes. European journal of pharmacology. 2014.
50. Kim J Y, Kim H, Suk K, Lee W H. Activation of CD147 with cyclophilin a induces the expression of IFITMI through ERK and PI3K in THP-1 cells. Mediators of inflammation. 2010; 2010:821940.
51. Elazar M, Liu M, McKenna S A, Liu P, Gehrig E A, Puglisi J D, Rossignol J-F, Glenn J S. The anti-hepatitis C agent nitazoxanide induces phosphorylation of eukaryotic initiation factor 2a via protein kinase activated by double-stranded RNA activation. Gastroenterology. 2009; 137(5): 1827-35.
52. Basler C F, Wang X, Muhlberger E, Volchkov V, Paragas J, Klenk H D, Garcia-Sastre A, Palese P. The Ebola virus VP35 protein functions as a type I IFN antagonist. Proc Natl Acad Sci USA. 2000; 97(22):12289-94.
53. Hartman A L, Ling L, Nichol S T, Hibberd M L. Whole-genome expression profiling reveals that inhibition of host innate immune response pathways by Ebola virus can be reversed by a single amino acid change in the VP35 protein. J Virol. 2008; 82(11):5348-58.
54. Hartman A L, Bird B H, Towner J S, Antoniadou Z A, Zaki S R, Nichol S T. Inhibition of IRF-3 activation by VP35 is critical for the high level of virulence of ebola virus. J Virol. 2008; 82(6):2699-704.
55. Schumann M, Gantke T, Muhlberger E. Ebola virus VP35 antagonizes PKR activity through its C-terminal interferon inhibitory domain. J Virol. 2009; 83(17):8993-7.
56. Feng Z, Cerveny M, Yan Z, He B. The VP35 protein of Ebola virus inhibits the antiviral effect mediated by double-stranded RNA-dependent protein kinase PKR. J Virol. 2007; 81(1):182-92.
57. Muhlberger E, Weik M, Volchkov V E, Klenk H D, Becker S. Comparison of the transcription and replication strategies of marburg virus and Ebola virus by using artificial replication systems. J Virol. 1999; 73(3):2333-42.
58. Elliott L H, Kiley M P, McCormick J B. Descriptive analysis of Ebola virus proteins. Virology. 1985; 147(1):169-76.
59. Zinzula L, Esposito F, Pala D, Tramontano E. dsRNA binding characterization of full length recombinant wild type and mutants *Zaire ebolavirus* VP35. Antiviral research. 2012; 93(3):354-63.
60. Cardenas W B, Loo Y M, Gale M, Jr., Hartman A L, Kimberlin C R, Martinez-Sobrido L, Saphire E O, Basler C F. Ebola virus VP35 protein binds double-stranded RNA and inhibits alpha/beta interferon production induced by RIG-I signaling. J Virol. 2006; 80(11):5168-78.
61. Leung D W, Ginder N D, Fulton D B, Nix J, Basler C F, Honzatko R B, Amarasinghe G K. Structure of the Ebola VP35 interferon inhibitory domain. Proc Natl Acad Sci USA. 2009; 106(2):411-6.
62. Leung D W, Prins K C, Borek D M, Farahbakhsh M, Tufariello J M, Ramanan P, Nix J C, Helgeson L A, Otwinowski Z, Honzatko R B, Basler C F, Amarasinghe G K. Structural basis for dsRNA recognition and interferon antagonism by Ebola VP35. Nat Struct Mol Biol. 2010; 17(2):165-72.

63. Bale S, Julien J P, Bornholdt Z A, Krois A S, Wilson I A, Saphire E O. *Ebolavirus* VP35 coats the backbone of double-stranded RNA for interferon antagonism. J Virol. 2013; 87(18):10385-8.
64. Basler C F, Mikulasova A, Martinez-Sobrido L, Paragas J, Muhlberger E, Bray M, Klenk H D, Palese P, Garcia-Sastre A. The Ebola virus VP35 protein inhibits activation of interferon regulatory factor 3. J Virol. 2003; 77(14): 7945-56.
65. Hartman A L, Dover J E, Towner J S, Nichol S T. Reverse genetic generation of recombinant *Zaire* Ebola viruses containing disrupted IRF-3 inhibitory domains results in attenuated virus growth in vitro and higher levels of IRF-3 activation without inhibiting viral transcription or replication. J Virol. 2006; 80(13):6430-40.
66. Prins K C, Cardenas W B, Basler C F. Ebola virus protein VP35 impairs the function of interferon regulatory factor-activating kinases IKKepsilon and TBK-1. J Virol. 2009; 83(7):3069-77.
67. Thomis D C, Samuel C E. Mechanism of interferon action: evidence for intermolecular autophosphorylation and autoactivation of the interferon-induced, RNA-dependent protein kinase PKR. J Virol. 1993; 67(12):7695-700.
68. Galabru J, Hovanessian A. Autophosphorylation of the protein kinase dependent on double-stranded RNA. J Biol Chem. 1987; 262(32):15538-44.
69. Prins K C, Delpeut S, Leung D W, Reynard O, Volchkova V A, Reid S P, Ramanan P, Cardenas W B, Amarasinghe G K, Volchkov V E, Basler C F. Mutations abrogating VP35 interaction with double-stranded RNA render Ebola virus avirulent in guinea pigs. J Virol. 2010; 84(6):3004-15.
70. Leroy E M, Baize S, Volchkov V E, Fisher-Hoch S P, Georges-Courbot M C, Lansoud-Soukate J, Capron M, Debre P, McCormick J B, Georges A J. Human asymptomatic Ebola infection and strong inflammatory response. Lancet. 2000; 355(9222):2210-5.
71. Leroy E M, Baize S, Debre P, Lansoud-Soukate J, Mavoungou E. Early immune responses accompanying human asymptomatic Ebola infections. Clinical and experimental immunology. 2001; 124(3):453-60.
72. Baize S, Leroy E M, Georges A J, Georges-Courbot M C, Capron M, Bedjabaga I, Lansoud-Soukate J, Mavoungou E. Inflammatory responses in Ebola virus-infected patients. Clinical and experimental immunology. 2002; 128(1):163-8.
73. Wauquier N, Becquart P, Padilla C, Baize S, Leroy E M. Human fatal zaire ebola virus infection is associated with an aberrant innate immunity and with massive lymphocyte apoptosis. PLoS neglected tropical diseases. 2010; 4(10).
74. Lam K K Y, Zheng X, Forestieri R, Balgi A D, Nodwell M, Vollett S, Anderson H J, Andersen R J, Av-Gay Y, Roberge M. Nitazoxanide stimulates autophagy and inhibits mTORC1 signaling and intracellular proliferation of *Mycobacterium tuberculosis*. PLoS Pathog. 2012; 8(5): e1002691.
75. Deretic V, Saitoh T, Akira S. Autophagy in infection, inflammation and immunity. Nat Rev Immunol. 2013; 13(10):722-37.
76. Singh V, Jain S, Gowthaman U, Parihar P, Gupta P, Gupta U D, Agrewala J N. Co-administration of IL-1+ IL-6+TNF-alpha with *Mycobacterium tuberculosis* infected macrophages vaccine induces better protective T cell memory than BCG. PLoS One. 2011; 6(1):e16097.
77. Ben-Sasson S Z, Hu-Li J, Quiel J, Cauchetaux S, Ratner M, Shapira I, Dinarello C A, Paul W E. IL-1 acts directly on CD4 T cells to enhance their antigen-driven expansion and differentiation. Proc Natl Acad Sci USA. 2009; 106 (17):7119-24.
78. Khoruts A, Osness R E, Jenkins M K. IL-1 acts on antigen-presenting cells to enhance the in vivo proliferation of antigen-stimulated naive CD4 T cells via a CD28-dependent mechanism that does not involve increased expression of CD28 ligands. Eur J Immunol. 2004; 34(4): 1085-90.
79. Leal I S, Smedegard B, Andersen P, Appelberg R. Interleukin-6 and interleukin-12 participate in induction of a type 1 protective T-cell response during vaccination with a tuberculosis subunit vaccine. Infect Immun. 1999; 67(11):5747-54.
80. Kash J C, Muhlberger E, Carter V, Grosch M, Perwitasari O, Proll S C, Thomas M J, Weber F, Klenk H D, Katze M G. Global suppression of the host antiviral response by Ebola- and Marburgviruses: increased antagonism of the type I interferon response is associated with enhanced virulence. J Virol. 2006; 80(6):300920.
81. Wahl-Jensen V, Kurz S, Feldmann F, Buehler L K, Kindrachuk J, DeFilippis V, da Silva Correia J, Fruh K, Kuhn J H, Burton D R, Feldmann H. Ebola virion attachment and entry into human macrophages profoundly effects early cellular gene expression. PLoS neglected tropical diseases. 2011; 5(10):e1359.
82. Atianand M K, Fitzgerald K A. Long non-coding RNAs and control of gene expression in the immune system. Trends in molecular medicine. 2014.

Example 2: A Role for IFITM3 in Restriction of Infection by *Mycobacterium Tuberculosis*

The interferon (IFN)-inducible transmembrane (IFITM) proteins are critical mediators of the host antiviral response. Here, the role of these proteins is expanded to the restriction of *Mycobacterium tuberculosis* (MTb) intracellular growth. It is shown that inhibition of IFITM3 expression by RNA interference significantly enhances MTb growth in human monocytic and alveolar/epithelial cells, and reciprocally, that overexpression of IFITM3 inhibits MTb growth. Furthermore, MTb infection of primary human macrophages, the direct engagement of Toll-like receptor (TLR)s 2, 4, and MyD88 signaling, or cellular stimulation with the MTb-induced cytokines tumor necrosis factor (TNF), interleukin-1 (IL-1), or IL-6, all induce IFITM3 gene expression. After MTb infection, IFITM3 co-localizes with MTb bacilli at intracellular endosomal compartments and is enriched at vesicles containing the late endosomal protein Rab7. These studies expand IFITM3's role to host defense against intracellular bacterial infection and establish its role in the restriction of MTb.

It is shown that IFITM3 is transcriptionally activated in response to MTb infection, as well as by several proinflammatory cytokines produced during MTb infection in addition to IFN-β. Using cells deficient in IFITM3 or that overexpress the protein, it is shown that IFITM3 restricts MTb infection and growth in diverse cell types. Finally, it is demonstrated that IFITM3 is enriched at MTb phagosomes that contain the late endosome/lysosome marker Rab7. These findings provide the first evidence that an IFITM family member directly inhibits a bacterial pathogen.

Results

IFITM3 is an MTb-Inducible Gene

Figure 5A:
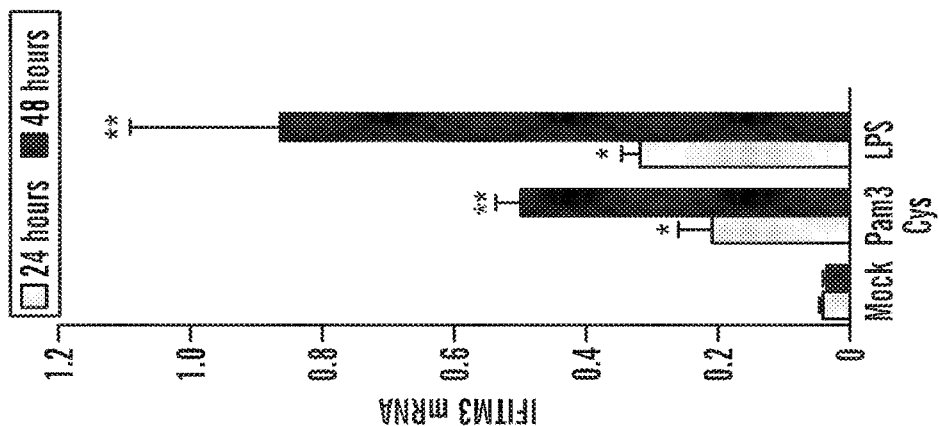

To determine if MTb could directly induce IFITM3 gene expression, primary human monocyte-derived macrophages (MDM) were infected with the clinical MTb strains CDC1551 and HN878 and the virulent lab-adapted MTb strain H37Rv and measured IFITM3 mRNA levels at 3, 24, and 48 hours post-infection (FIG. 5A). Strikingly, infection of MDM with all three strains significantly induced IFITM3 mRNA levels after 24 and 48 hours (FIG. 5A), demonstrating that a member of the IFITM family as a bacterially inducible gene.

Figure 5B:
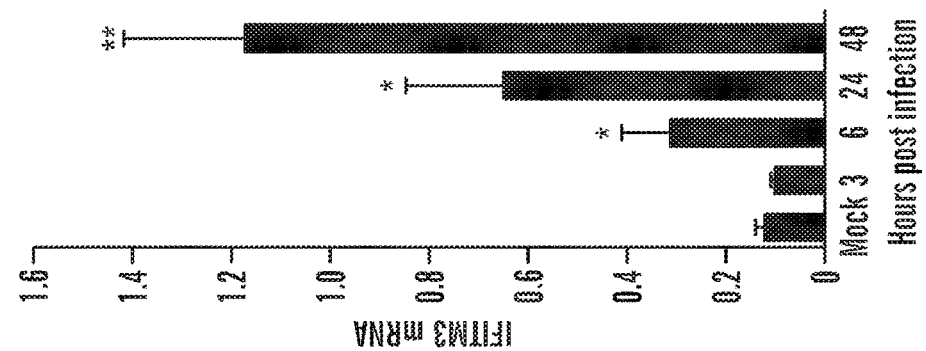
Figure 5C:
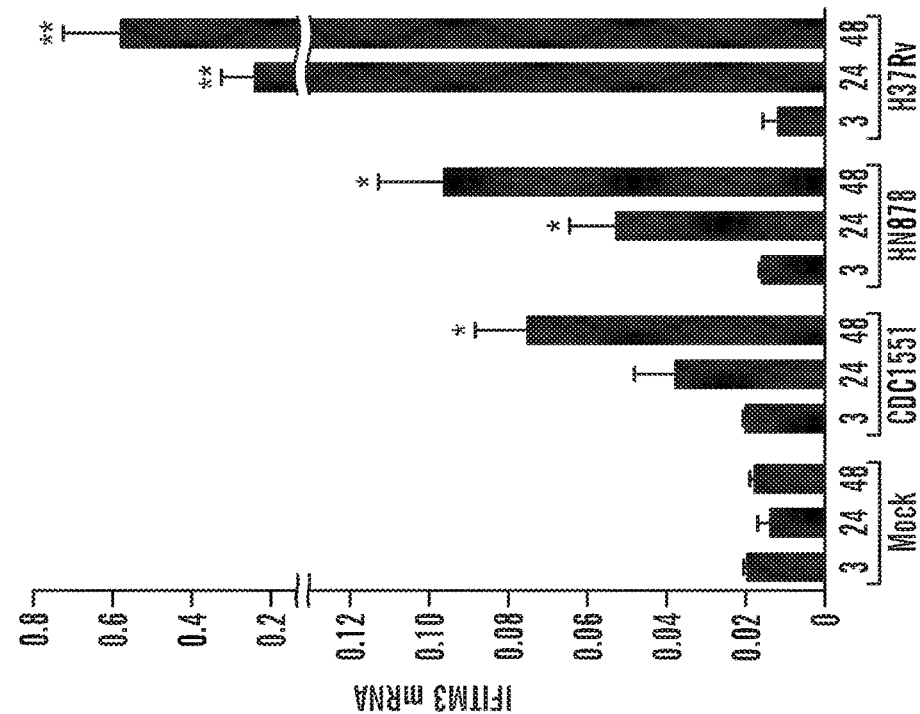

TLR2/4 and MYD88 Signaling Pathways are Involved in MTb-Induced Expression of IFITM3 mRNA Several MTb components trigger signaling of the major pathogen pattern recognition receptors (PRRs) TLR2 and TLR4, which then leads to the activation of innate immune response genes (Means et al., 1999; Underhill et al., 1999). In order to examine the signal transduction pathways involved in MTb-dependent induction of IFITM3 expression, the human monocytic cell line THP-1 is next utilized, which is commonly used as a model system for infection by MTb and other pathogens of the lung (Shattock et al., 1993; Shattock et al., 1994; Sibille et al., 1994). Consistent with the results in primary cells, IFITM3 mRNA levels were significantly elevated at 24 and 48 hours post-infection and were already significantly induced by 6 hours post-infection with H37Rv-MTb (FIG. 5B). Furthermore, activation of THP-1 cells with the TLR2 agonist Pam3Cys, or with the TLR4 agonist LPS, also significantly induced IFITM3 gene expression (FIG. 5C), and after 24 and 48 hours IFITM3 mRNA levels were comparable to those induced by live MTb infection, demonstrating that these PRRs can directly transmit signals capable of activating IFITM3 gene expression.

Upon engagement of TLR2 or TLR4, the adaptor molecule MyD88 transmits signals to downstream kinases, including IRAK1 and TRAF6, which are critical for the ultimate activation of the MAPK and NF-κB pathways and transcriptional induction of host immune response genes (Burns et al., 1998; Kawai et al., 1999; Medzhitov et al., 1998; Muzio et al., 1998; Takeuchi et al., 2000; Yang et al., 1999). To determine the contribution of these signaling intermediaries to MTb-induced IFITM3 gene expression, THP-1 cells stably expressing shRNAs to MyD88, IRAK1, or TRAF6 were infected with MTb H37Rv and IFITM3 mRNA levels were measured. As shown FIG. 5D, knockdown of each protein led to a significant reduction in IFITM3 transcript production as compared to THP-1 cells stably expressing a scrambled control shRNA, indicating that MTb activation of IFITM3 gene expression is direct and at least partially dependent on MTb-activated signaling by components downstream of TLRs.

MTb infection also induces the expression of numerous proinflammatory innate immune cytokines that are critical mediators of the host response, including TNF, IL-10, and IL-6, in addition to type I IFNs (Etna et al., 2014). While IL-1β signaling requires the MyD88/IRAK1/TRAF6 axis, TNF and IL-6 activate distinct signaling pathways. All three of these cytokines and are themselves significantly induced by TLR2 or TLR4 activation in THP-1 cells by 3 hours (or in the case of IL-6 by 24 hrs post-TLR2 stimulation) post-stimulation (Falvo et al. 2011; and FIG. 9). To investigate the ability of these cytokines to induce IFITM3 gene expression in monocytic cells, THP-1 cells were treated with recombinant IL-1β, IL-6, or TNF, and, as a positive control, IFN-β, and IFITM3 mRNA expression was assessed after 24 and 48 hours. As shown in FIG. 5E, IFN-β stimulation resulted in a ~6-fold and ~12-fold increase in IFITM3 mRNA at 24 and 48 hours, respectively. IL-6 also induced a significant increase in IFITM3 transcript levels by 24 hours post-stimulation, while TNF and IL-1β induced a slower accumulation of IFITM3 mRNA, which was however significantly elevated as compared to untreated control cells by 48 hrs. Taken together, these data indicate that IFITM3 gene expression is induced by several signaling pathways that are activated during MTb infection; these include direct engagement of the TLR2 and TLR4 signaling pathways and via secondary activation by MTb-induced cytokines.

Figure 6A:
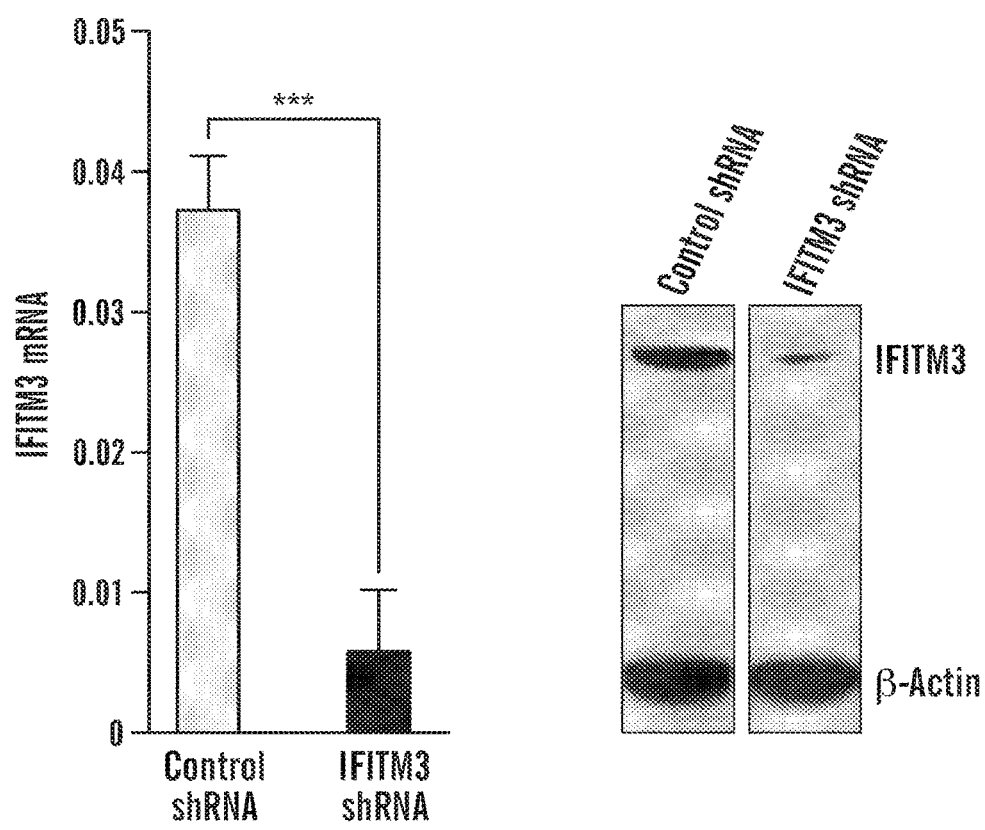
Figure 6B:
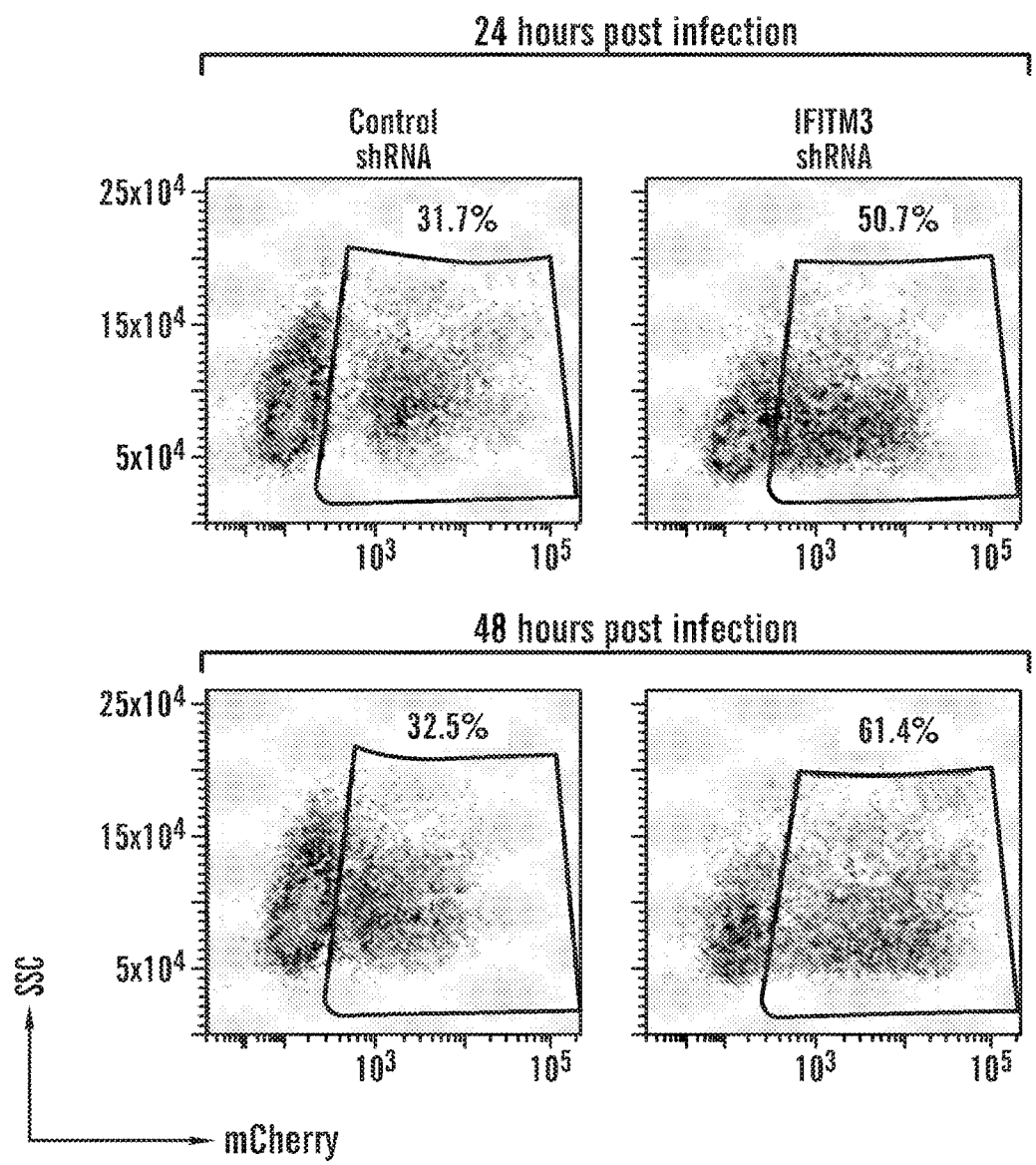

Inhibition of Endogenous IFITM3 Increases Intracellular Growth of MTb in Monocytes To directly assess the role of IFITM3 in MTb infection, IFITM3 expression in THP-1 cells is inhibited and the effect of reduced IFITM3 levels on MTb infection and replication is investigated. Lentiviral delivery of an IFITM3-specific shRNA to knock down IFITM3 gene expression resulted in a reduction in IFITM3 mRNA levels of approximately 90% (FIG. 6A), which corresponded to a marked reduction in IFITM3 protein levels (FIG. 6B). As shown in FIG. 2C, infection of IFITM3-knock down (KD) THP-1 cells with mCherry-expressing virulent H37Rv MTb (mCherry-H37Rv) resulted in 1.7-fold and 1.9-fold increases in the percentage of MTb-infected cells at 24 and 48 hours post-infection, respectively, as compared to THP-1 cells transduced with a scrambled control shRNA. In addition, mCherry mean fluorescence intensity (MFI) was significantly higher in IFITM3-KD THP-1 cells versus control cells by 48 hours post-infection, indicating the presence of increased MTb bacteria per cell (FIG. 6D). To confirm that this effect was due to intracellular MTb replication, colony-forming unit (CFU) assays in H37Rv-MTb infected scrambled control and IFITM3-KD THP-1 cells were next performed. Consistent with the FACS analysis of mCherry-H37Rv, a significant increase ($p<0.01$) in MTb replication was observed at two and three days post-MTb infection in IFITM3-KD THP-1 cells versus control THP-1 cells (FIG. 6E). Taken together, these results demonstrate that reduction of IFITM3 expression results in increased MTb infection and/or replication in human monocytic cells.

IFITM3 Restricts MTb Infection in Human Lung Alveolar Cells

Figure 7B:
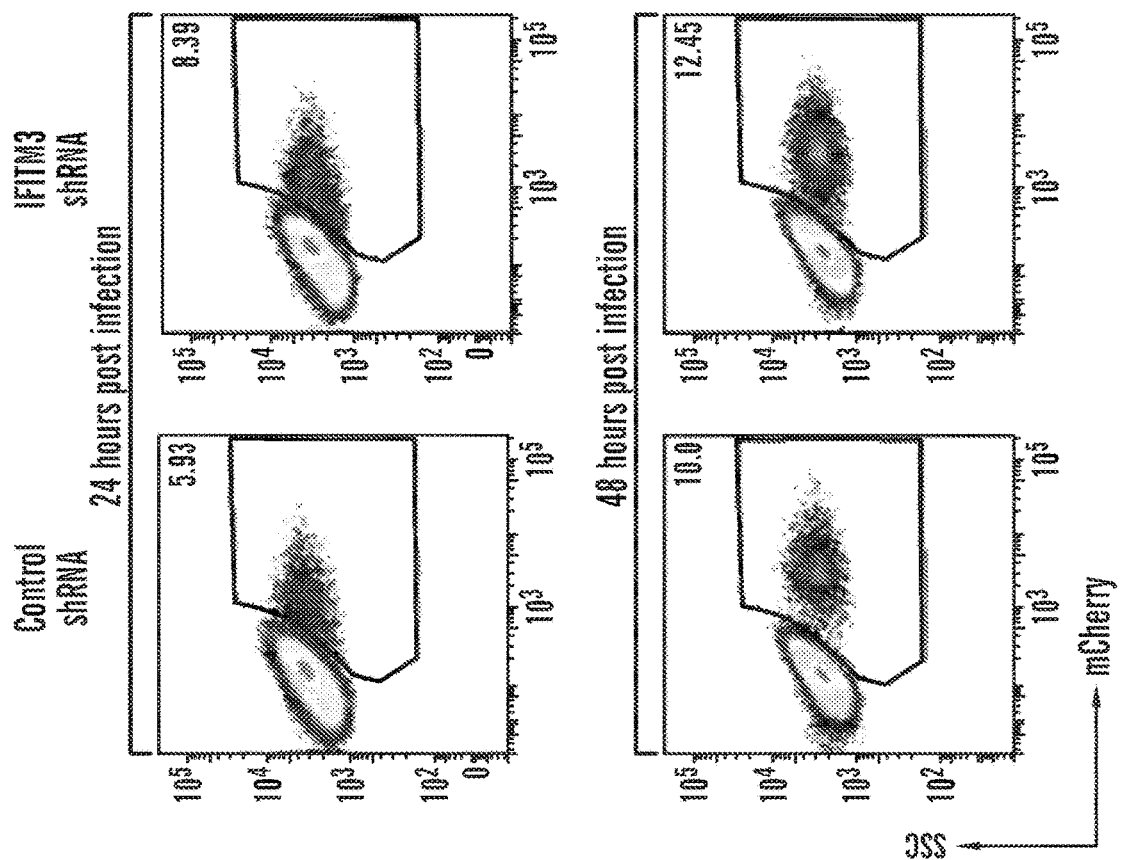
Figure 7A:
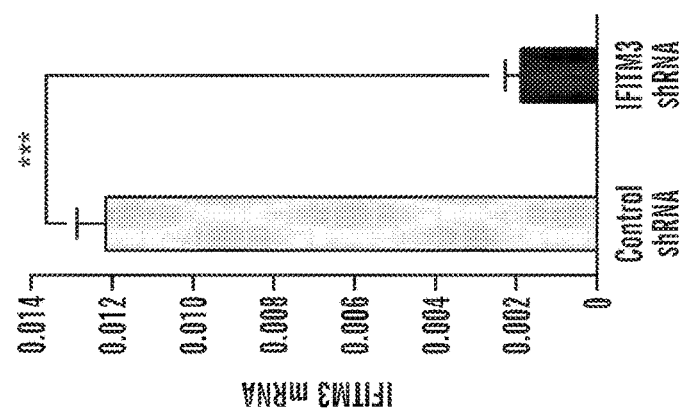
Figure 9A:
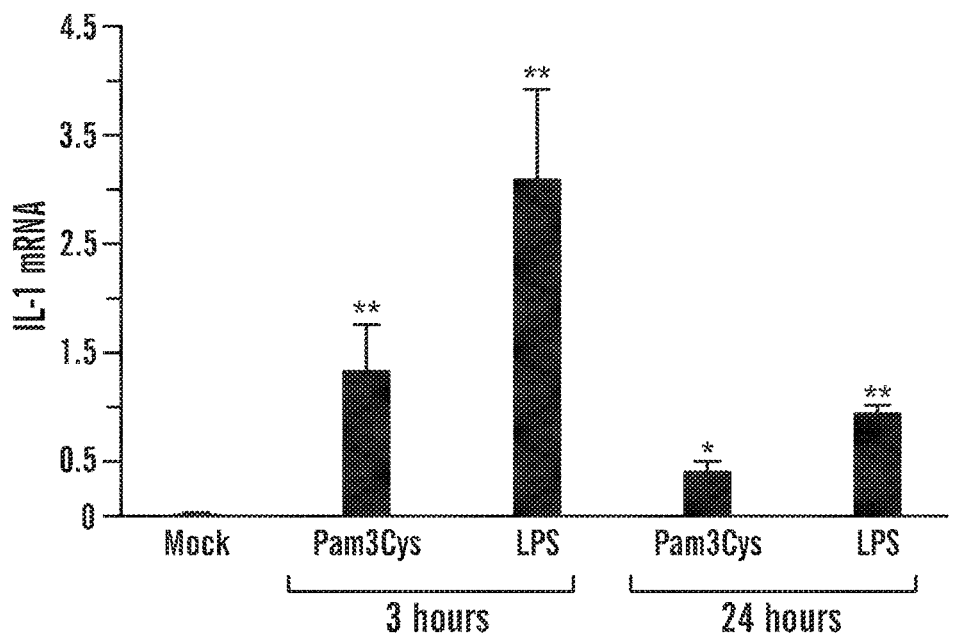
Figure 9B:
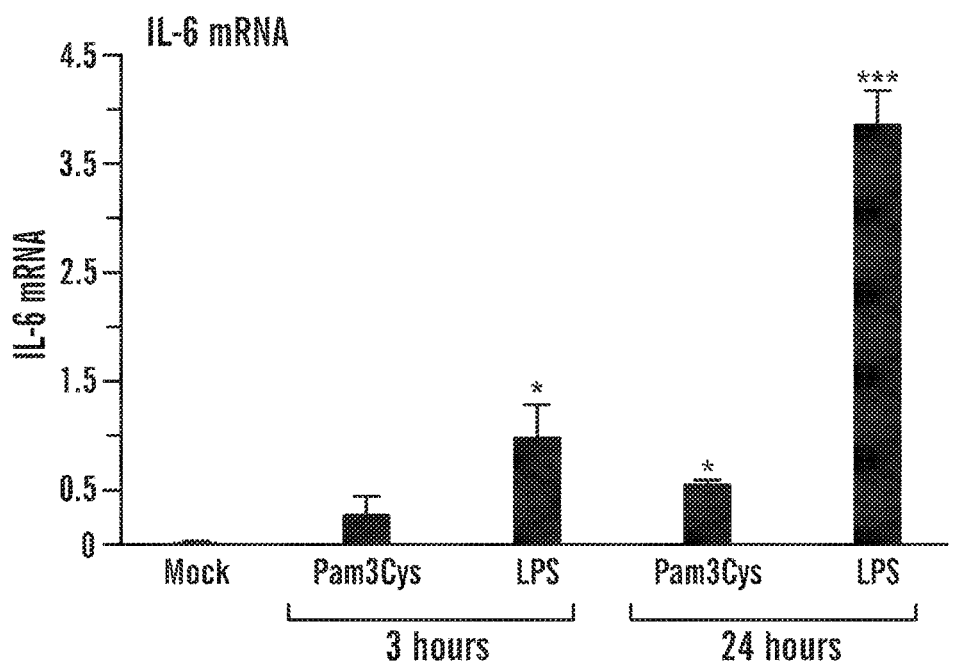
Figure 9C:
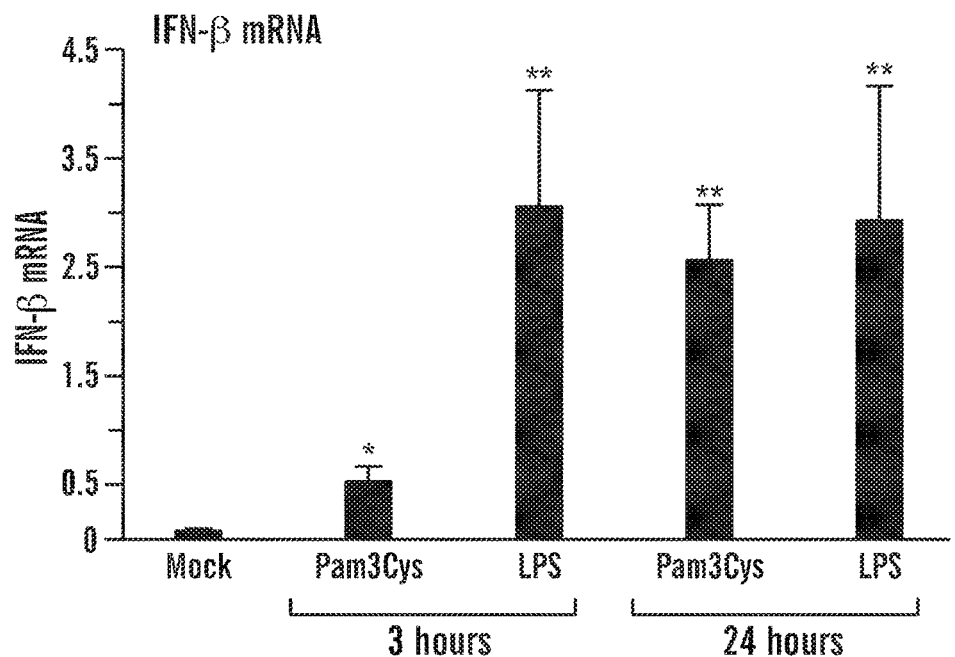
Figure 9D:
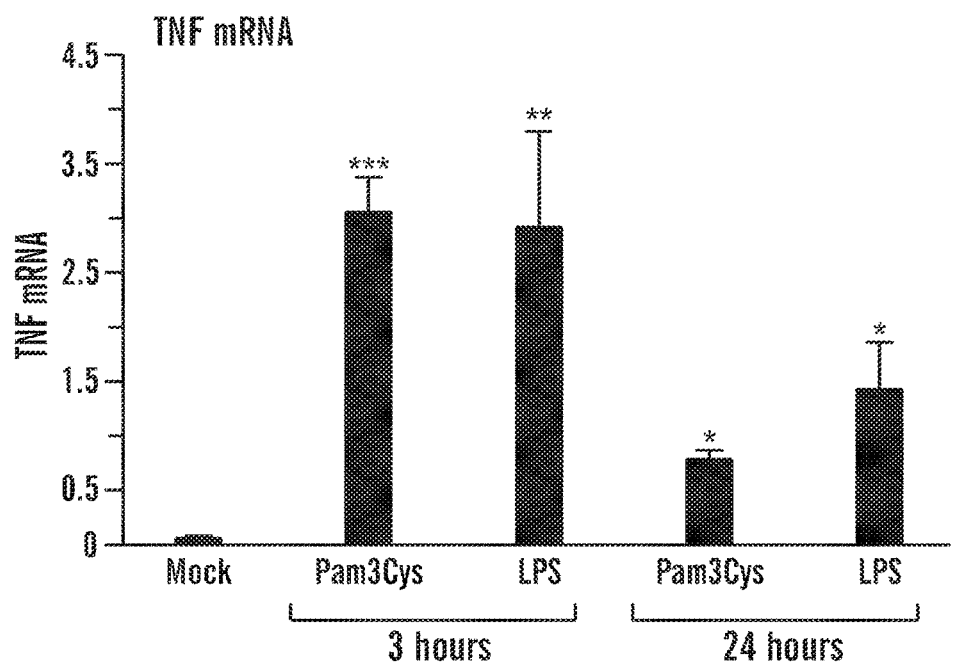

The IFITMs show differential antiviral effects depending on cell type (Huang et al., 2011). To determine whether IFITM3 also impairs MTb infection in non-myeloid cells, the studies were extended to the A549 human lung alveolar epithelial carcinoma cell line, which has provided a long-standing model for MTb infection (Bermudez and Goodman, 1996; McDonough and Kress, 1995), and more recently for functional analysis of IFITM3 antiviral activity (Huang et al., 2011). Similar to the findings with THP-1 cells, when IFITM3 is knocked down in A549 cells (FIG. 7A) an increase in MTb infection was found at 24 and 48 hrs of ~1.4-fold and ~1.5-fold, respectively, as compared to A549 cells transduced with the control shRNA (FIG. 7B). To further confirm the inhibitory capacity of IFITM3 on MTb infection, A549 cells that constitutively overexpressed IFITM3 by lentiviral transduction were next generated and incubated with mCherry-H37Rv infected cells (FIG. 7C). As shown in FIG. 7D, overexpression of IFITM3 inhibited MTb infection by ~1.3 and ~1.4 fold at 24 and 48 hours post-infection, respectively (FIG. 7D). These findings thus demonstrate a broad spectrum of activity of IFITM3 in restricting MTb infection of host cells that are primary targets during natural infection.

Intracellular Localization of IFITM3 Overlaps with MTb Bacilli in Early and Late Phagosomes MTb prevents phagosome maturation and fusion with late endosomes and lysosomes and blocks v-ATPase recruitment to the maturing phagosome, thereby excluding proteins associated with these acidic compartments such as Rab7 and CD63 (Clemens and Horwitz, 1995; Hmama et al., 2004; Roberts et al., 2006; Via et al., 1997). Notably, IFITM3's antiviral activity has been associated with its distribution to late endosomal/lysosomal membranes and its ability to promote increases in the number and size of acidic intracellular compartments (Feeley et al., 2011; Mudhasani et al., 2013; Wee et al., 2012). Based on the findings that IFITM3 restricts MTb infection of human myeloid and alveolar epithelial cells, one mechanism underlying IFITM3's antimycobacterial activity might be its ability to co-localize with MTb in compartments of increased acidity. To investigate this possibility, A549 cells were transduced with a lentiviral vector encoding IFITM3 tagged at its C-terminus with a V5 epitope tag, or with an empty lentiviral vector as a control. Stable overexpression of native or epitope-tagged IFITM3 has been shown to localize mainly to the late endosome and lysosome in A549 cells (Amini-Bavil-Olyaee et al., 2013; Feeley et al., 2011; Huang et al., 2011; Williams et al., 2014). IFITM3-V5 and control A549 cells were infected with mCherry-H37Rv and then analyzed by confocal microscopy. As shown in FIG. 8, internalized MTb bacilli co-localized to some extent with IFITM3 at early Rab5+ phagosomal compartments (FIGS. 8A & 8B), and its co-localization with IFITM3 with late Rab7+ phagosomal compartments was stronger (FIGS. 8C & 8D), thus indicating that IFITM3 is primarily found at phagosomal membranes that are progressing to phagolysosomal maturation. IFITM3 overexpression increased the staining intensity of Rab7 (FIG. 8B), consistent with previous observations (Feeley et al., 2011).

Discussion

Historically, the IFITMs have been considered IFN-inducible proteins, although a previous report has shown that recombinant IL-1β can stimulate the induction of IFITM3 mRNA synthesis in human hepatocarcinoma cells (Zhu and Liu, 2003), and two recent reports found that murine astrocytes produce IFITM3 in response to TLR3 activation by polyI:C, TLR4 activation by LPS, or stimulation with recombinant TNF or IL-1β (Ibi et al., 2013; Nakajima et al., 2014). Here, it is shown that infection of human myeloid cells by virulent MTb strains induces the expression of IFITM3 transcription, and that several other pathways triggered by MTb infection, including signaling through TLR2/TLR4 and via the signaling cascades stimulated by the proinflammatory cytokines TNF, IL-6, and IL1-β, also induce IFITM3 gene expression. Moreover, it is shown that overexpression of IFITM3 restricts MTb infection and that its deficiency results in enhanced MTb growth and replication in two different cell types targeted during live MTb infection. These data thus expand the role of IFITM proteins to the restriction of a bacterial pathogen.

Previous reports have demonstrated that IFITM3 overexpression leads to an increase in the size and number of acidic compartments in murine and human cells (Feeley et al., 2011; Mudhasani et al., 2013; Wee et al., 2012), and that IFITM3 interacts with v-ATPase and promotes phagosomal acidification (Wee et al., 2012). Arrest of phagosome maturation is a hallmark of virulent MTb infection (Armstrong and Hart, 1971), and MTb mutants with impaired ability to block phagosome maturation generally exhibit impaired growth in macrophages (Casonato et al., 2014; Corrales et al., 2012; MacGurn and Cox, 2007; Pethe et al., 2004; Stewart et al., 2005). Furthermore, mycobacterial factors have been shown to specifically block the v-ATPase at phagosomal membranes resulting in the inhibition of acidification (Bach et al., 2008; Sturgill-Koszycki et al., 1994; Wong et al., 2011). Thus, the finding that knockdown of IFITM3 increases MTb replication in human monocytic cells and A549 epithelial cells, taken together with the demonstration that IFITM3 co-localizes with MTb in Rab7+ late phagosomes, suggests a role for IFITM3 in the acidification of cellular compartments where MTb growth is restricted.

Notably, a study examining bacterial burden of MTb in the lungs of C57BL/6 mice lacking the ifitm3 gene did not differ significantly from that of wild-type mice over the course of the first 28 days post-aerosol infection with H37Rv MTb (Everitt et al., 2013). However, compared to humans, mice possess two additional ifitm family members, termed ifitm6 and ifitm7 (Lange et al., 2008). Furthermore, ifitm6 expression is strongly induced in murine macrophages in response to TLR activation (Han et al., 2011), consistent with a redundant functional role with the function of Ifitm3, given the demonstration that IFITM3 is highly inducible by TLR signaling. Moreover, the murine background of C57BL/6 mice has been shown to poorly recapitulate human responses to trauma and inflammatory assault, and to be a particularly poor model for pathways that are critical during MTb infection, such as macrophage phagocytosis activity and TLR signaling (Seok et al., 2013). Thus, it is not a fair comparison or informative to extrapolate data from the isolated deletion of Ifitm3 in C57BL6 mice to the role of human IFITM3 in human TB.

Finally, the studies described herein demonstrate that a potent host viral restriction factor also exhibits activity against a clinically important intracellular bacterium, MTb. Intriguingly, in the primate lineage in particular, IFITM gene duplication events are common, leading to diverse numbers of immune-related IFITM genes (Zhang et al., 2012). In the case of TB, which is thought to have emerged from Africa along with the first humans, MTb infection has been a persistent and powerful cause of human mortality (Gagneux, 2012). It is thus interesting to speculate that IFITM genes have co-evolved with mycobacteria and have played an important role in the co-evolution of the host-pathogen dynamic caused by TB in humans.

Experimental Procedures

MTb Culture

The MTb strains H37Rv, H37Rv-mCherry (H37Rv expressing mCherry fluorescent protein), HN878, and CDC1551 were prepared by adding 100 µl of frozen bacterial stock into 10 ml of Middlebrook 7H9 medium (Difco BD, www.bd.com) supplemented with albumin dextrose complex (ADC) and 0.05% Tween 80 (Sigma-Aldrich, www.sigmaaldrich.com). The cultures were grown to an $OD_{650}$ of 0.4 at 37° C. to ensure that they were in the logarithmic growth phase. Bacteria were then pelleted, washed with PBS, resuspended in PBS, and passed through a 5 µm filter to ensure that the bacteria were in a single cell suspension. Bacterial cell numbers were determined by measurement of $OD_{650}$ before further dilution with RPMI 1640 medium for cell infection studies. H37Rv-mCherry (Sale et al., 2011) was kindly provided by Dr. Sarah Fortune.

Cell Culture

Peripheral blood mononuclear cells (PBMC) from normal unidentified donors were obtained from the Boston Children's Hospital Blood Donor Center and isolated by Ficoll-Hypaque (Pharmacia Corporation, Peapack, N.J.) density gradient centrifugation. Human monocytes were isolated from PBMC preparations by positive selection with CD14 microbeads (STEMCELL Technologies, Inc., www.stemcell.com) as described by the manufacturer, and were cultured at $1\times10^6$ cells per well in 6-well plates in RPMI 1640 medium with 2 mM L-glutamine (BioWhittaker, Inc., Walkersville, Md.) supplemented with 5% heat-inactivate human AB serum (Atlanta Biologicals, www.atlantabio.com) and 50 ng/ml recombinant human GM-CSF (R&D Systems, Inc., www.rndsystems.com). The cell cultures were incubated at 37° C. and 5% $CO_2$ for 5 days, after which supernatant was replaced with fresh medium lacking GM-CSF before manipulation. More than 98% of the adherent cells obtained with this technique were $CD14^+$ macrophages as verified by flow cytometry. THP-1 cells were obtained from ATCC (www.atcc.org) and cultured in RPMI 1640 medium supplemented with 10% FCS (BioWhittaker, www.lonzabio.com). 293T and A549 cells were obtained from ATCC and were maintained in Dulbecco's Modified Eagle's medium (DMEM) (BioWhittaker, www.lonzabio.com) supplemented with 10% FCS.

Construction of Cell Lines Expressing shRNA or Protein

Lentiviral plasmids (pLKO.1 parent vector) expressing shRNA targeting human IFITM3 or a scrambled sequence shRNA (control) were obtained from Open Biosystems (www.openbiosystems.com) and validated. The pLX304-IFITM3-V5 tag plasmid expressing IFITM3 protein and the pLX304-V5 parent vector were obtained from the Dana Farber/Harvard Cancer Center DNA Resource Core and Addgene (www.addgene.org), respectively. Lentiviruses were generated by transfecting 293T cells with the plasmids above in combination with the packaging plasmid psPAX2 and the envelope plasmid pMD2.G using Effectene transfection reagent (Qiagen, www.qiagen.com). Supernatants were collected 24 and 48 hours post-transfection, clarified by centrifugation, and stored at −80° C. THP-1 or A549 cells were transduced with the lentiviral particles by culturing the cells with supernatants from the virus-producing cells in the presence of 8 μg/ml polybrene (Millipore, www.millipore.com) and spinoculation for two hours at 500×g). Successfully transduced cells were selected and expanded by treatment with 1 μg/ml puromycin or 10 μg/m blasticidin. THP-1 cells expressing shRNA targeting MYD88, IRAK1, or TRAF6 were prepared as described previously (Ranjbar et al., 2012).

Quantitative PCR

The mRNA expression levels were determined by SYBR Green-based real-time PCR (Applied Biosystems, www.appliedbiosystems.com) with the following gene-specific primers: IFITM3 (forward 5'-ATGTCGTCTGGTCCCT-GTTC-3' (SEQ ID NO: 1) and reverse 5'-GGGATGACGAT-GAGCAGAAT-3') (SEQ ID NO: 2); IL-1β forward 5'-GCT-GAGGAAGATGCTGGTTC-3' (SEQ ID NO: 3) and reverse 5'-TCCATATCCTGTCCCTGGAG-3') (SEQ ID NO: 4); IL-6 (forward 5'-AGGAGACTTGCCTGGTGAAA-3' (SEQ ID NO: 5); and reverse 5'-CAGGGGTGGTTATTGCATCT-3') (SEQ ID NO: 6); IFN-β (forward 5'-GAATGGGAG-GCTTGAATACTGCCT-3'(SEQ ID NO: 7) and reverse 5'-TAGCAAAGATGTTCTGGAGCATCTC-3') (SEQ ID NO: 8); TNF (forward 5'-TCTTCTCGAACCCCGAGTGA-3' (SEQ ID NO: 9) and reverse 5'-CCTCTGATGGCAC-CACCA-3') (SEQ ID NO: 10); Cyclophilin B (forward 5'-AGAAGAAGGGGCCCAAAGT-3'(SEQ ID NO: 11) and reverse 5'-AAAGATCACCCGGCCTACAT-3') (SEQ ID NO: 12). The reaction conditions were 95° C. for 10 minutes followed by 40 cycles of 95° C. for 15 sec and 60° C. for 1 minute. The results were normalized using cyclophilin B mRNA as an internal control and expressed as relative values.

Western Blot Assay

Whole cell extracts were collected with lysis buffer containing 150 mM NaCl, 50 mM Tris-HCl, pH 7.5, 1% Triton X-100, 10% glycerol, and 1 tablet of Complete EDTA-free Protease Inhibitor Cocktail (Roche, lifescience.roche.com) per 25 ml of buffer. Extracts were boiled for 5 minutes in 1× Laemmli sample buffer with 5% v/v 2-mercaptoethanol and proteins were separated by SDS-PAGE. The gel was transferred to a nitrocellulose Trans-Blot Transfer Membrane (BioRad, www.bio-rad.com). The blot was then blocked for 1 hour at room temperature in a solution of 5% non-fat milk and 0.1% Tween-20 (BioRad, www.bio-rad.com) in a buffer containing 50 mM Tris and 150 mM NaCl at pH 7.6 (milk-TBST). Primary incubation was carried out with a 1:1500 dilution of mouse monoclonal anti-IFITM3 antibody (clone 4C8-1B10, Sigma, www.sigmaaldrich.com) and a rabbit anti-β-Actin (ab 8227, Abcam, www.abcam.com) in milk-TB ST for 2 hours at room temperature. The blot was washed 3×5 minutes in TBST and incubated in 1:6000 goat anti-rabbit-HRP (sc2030, Santa Cruz Biotechnology) or goat anti-mouse-HRP (A00160, GenScript, www.genscript.com) as appropriate for 1 hour. The blot was again washed 3×5 minutes in TBST and developed with SuperSignal West Pico Chemiluminescent Reagent (Pierce, www.piercenet.com).

Flow Cytometry

Cells were left uninfected or infected with MTb-mCherry for the indicated time points, after which the cultures were terminated. Cells were washed with PBS, fixed with 4% paraformaldehyde, and analyzed by 5-laser FACSAria II systems (Becton Dickinson, www.bdbiosciences.com) according to standard techniques. Results were analyzed using Flowjo software package (Flowjo, www.flowjo.com).

Colony Forming Unit (CFU) Assay

THP-1 cells expressing IFITM3 shRNA or control shRNA ($1\times10^6$) were seeded in 6-well plates in triplicate and were infected with H37Rv at a ratio of 1:10 cells:bacilli. After a 3-hour incubation at 37° C. the cultures were treated with 200 μg/ml puromycin for 20 minutes. Cells were washed 3 times with PBS and were cultured in 1.5 ml fresh RPMI plus 10% FCS for 0, 48, and 72 hours and incubated at 37° C. and 5% $CO_2$. Following each time point, cultures were terminated, cells were treated with lysis buffer and sonicated, and serial dilutions were prepared and inoculated in Middlebrook 7H11 agar in triplicate. Colonies were analyzed on day 25 post-infection.

Fluorescence Microscopy

A549 cells transduced with IFITM3-V5 tagged expressing vector or empty vector were seeded on a small coverslip in 12 well plates in fresh media and were infected with MTb-mCherry (1:10 cells:bacilli) for three hours after which the cultures were washed and fresh media was added. Cells were further incubated at 37° C. for 20 hours. MTb-infected cells were fixed with 4% paraformaldehyde before they were blocked and permeabilized with buffer containing 5% normal donkey serum and 0.3% Triton X-100 in PBS for 2 hours. Cells were labeled with 1:150 rabbit anti-Rab5 or 1:100 rabbit anti-Rab7 antibody (Cell Signaling, www.cellsignal.com) overnight in antibody dilution buffer containing 1% BSA followed by 1:500 secondary Donkey anti-Rabbit DyLight 649 antibody (Biolegend, www.biolegend.com) for 2 hours. Cells were further labeled with mouse FITC anti-VS antibody (Invitrogen, www.lifetechnologies.com) overnight after which slides were mounted in mounting media with DAPI. Images were captured with an Olympus (FV1000) confocal microscope and Fluoview Software 2. Analysis was performed using ImageJ software.

Example 3: Mechanisms of NTZ Regulation of TB/HIV Co-Infection

Tuberculosis (TB) is the leading cause of mortality in human immunodeficiency virus (HIV)-infected patients, and is estimated to be responsible for a third to a half of all HIV-related deaths (10). MTb infection drives enhanced HIV replication and disease progression, while HIV-associated immune changes such as CD4+ T cell depletion lead to increased risk of de novo MTb infection and, most importantly, much greater rates of reactivation of latent MTb (8). The standard therapeutic approach to reducing MTb reactivation in areas of endemic HIV is isoniazid (INH) monotherapy; however cure is not durable in HIV patients with skin-test+ latent TB treated with INH, nor does INH treatment decrease the incidence of TB in high burden settings (11-13). Furthermore, treatment of active TB and HIV is complicated by drug-drug toxicity, development of drug resistance, and risk of immune reconstitution inflammatory syndrome (IRIS)(14). Thus, novel treatments are needed to better control latent TB reactivation and active TB in the context of HIV co-infection. Specific host restriction factors may be capable of modulating both latent and active MTb and HIV infections, and that these host factors present therapeutic targets for novel treatment strategies to control TB/HIV co-infection.

It was discovered that the interferon-stimulated gene (ISG) product, interferon-inducible trans-membrane protein 3 (IFITM3), inhibits MTb growth in human monocytes and its transcription is induced by MTb infection. Notably, IFITM3 has previously been shown to inhibit HIV-1 infection (15-17). Based on these findings, IFITM3 may be an important host restriction factor for TB/HIV co-infection and is able to inhibit MTb replication and establishment of latency in human macrophages by promoting phagosome maturation via perturbation of host lipid biosynthesis and assembly and augmenting phagosome acidification. The ability of IFITM3 to inhibit MTb in ex vivo monocyte-derived macrophage (MDM)/lymphocyte and alveolar macrophage (AM)/lymphocyte model systems is examined. The signaling pathways involved in MTb induction of IFITM3 expression in MDM and AM is elucidated, and IFITM3-dependent cellular mechanisms in lung epithelial cells and macrophages that drive MTb phagosome-lysosome fusion and MTb degradation are dissected. These studies define the role of IFITM3 in MTb/HIV co-infection of cells that are major in vivo targets of TB/HIV infection. Furthermore, these studies can identify IFITM3-associated factors that may serve as targets for immunomodulatory or transcriptional approaches aimed at expediting latent TB clearance while simultaneously augmenting antiretroviral treatment in TB/HIV patients.

It was also found that IFITM3 transcription is upregulated in human myeloid cells by the FDA-approved small molecule drug nitazoxanide (NTZ), which has been shown previously to inhibit both non-replicating and replicating MTb in in vitro culture (18, 19). NTZ has been widely used for treatment of diverse infections, including hepatitis C, protozoa, and influenza (20-23). Data demonstrate that NTZ is able to induce the expression of several other immune-related genes in human macrophages in addition to IFITM3, including the HIV-1 restriction factor SAMHD1. Studies also show NTZ inhibits MTb and HIV-1 infection of human monocytes/macrophages and suppresses TLR-mediated activation of a latently integrated HIV-1 minigenome in human monocytic cells. Based on these data, NTZ may inhibit HIV infection and MTb replication and establishment of latent TB via its induction of IFITM3 and other host factors in MDM and AM. These experiments can provide important data in support of rapid repurposing of NTZ for treatment of latent and active TB in HIV+ patients.

The role of IFITM3 in regulation of TB/HIV co-infection of primary human cells is determined. The signal transduction pathways involved in MTb regulation of IFITM3 gene expression is determined. The cellular mechanisms involved in IFITM3-mediated restriction of MTb infection are elucidated.

Macrophages:

Macrophages are among the first cells infected during acute HIV infection (25, 26) and lung AMs are the primary target of infection by inhaled mycobacteria (27) and are a major source of latent organisms within granulomous environments (28). In addition, tissue-resident macrophages have been implicated as a major HIV reservoir that persists during successful antiretroviral therapy (29-32). AMs are also infected by HIV during acute infection (32). However, within a few weeks post-HIV infection, viral replication is suppressed in AM in the lungs—a process that has been linked to transiently elevated IFN levels (33). Data suggest that low-level viral replication continues in AM during asymptomatic infection, leading to a persistent reservoir of HIV-infected AMs from which virus can be reactivated during stimulation by neighboring cells during a secondary lung infection such as by MTb, which has been linked to increased viral load (34, 35). Notably, when isolated macrophages, whether MDM differentiated in vitro by granulocyte monocyte colony stimulating factor (GM-CSF), or AMs prepared from bronchoalveolar lavage (BAL), are infected with HIV and then co-infected with MTb ex vivo, HIV replication is suppressed (33, 36). However, when activated autologous lymphocytes are added to the macrophage culture, the inhibition is reversed, and MTb augments HIV replication recapitulating what is found in vivo in patients (37). Both soluble lymphocyte-derived factors and direct lymphocyte-macrophage contacts were found to be critical for MTb enhancement of HIV transcriptional activation during co-infection (37). This finding underscores the importance of analyzing MTb/HIV co-infection in macrophages in isolation to discern mechanistic processes regulating infection and growth of both pathogens in this cell type while, at the same time, complementing such studies with systems incorporating co-culture of macrophages with lymphocytes in order to understand host responses in a cellular milieu that is more reflective of in vivo co-infection. Experiments are performed with i) MDM prepared from peripheral blood or AM obtained from BAL, and ii) MDM or AM reconstituted with autologous lymphocyte cultures or PBMC cultures after experimental manipulation or chemical treatment of the macrophages. Such methods have been successfully employed to study T cell activation/anergy in the context of TB, and in experiments studying HIV replication driven by MTb (38, 39). By examining co-infection in macrophages in the absence or presence of autologous lymphocytes, mechanisms involved in the response to co-infection that are wholly dependent on macrophage-related factors, and those that only come into play when the co-infected macrophage is in a milieu that includes lymphocytes can be clearly distinguished.

Members of the IFITM protein family (40, 41) were previously shown to inhibit growth of the HIV subtype B isolate BH10 in SupT1 T cells at an early step and were enriched in endocytic membranes after HIV infection (17). IFITMs 1-3 are induced by type I IFN, however, IFITM1 and IFITM3 can also be stimulated by IFN-γ (42-46), and all three isoforms inhibit a broad spectrum of viruses (15, 47-49). Notably, those viruses that are strongly inhibited by IFITM3 overexpression, such as influenza, primarily fuse with host-cell membranes in late endosomes and/or multivesicular bodies (MVBs)(50-55). After IFN stimulation, IFITM3 resides in late endosomes and lysosomes (56). By contrast, arenaviruses, which are not restricted by IFITMs, are taken up in clathrin-coated recycling endosomes (57, 58). The antiviral activity of IFITM3 appears to be due, in part, to its ability to disrupt cholesterol homeostasis (59). Specifically, IFITM3 interacts with vesicle-membrane-protein-associated protein A (VAPA) and blocks its interaction with oxysterol-binding protein (OSBP), leading to excess accumulation of cholesterol in late endosomes and MVBs. This, in turn, inhibits viral envelope-endosomal membrane fusion and viral access to the cytoplasm (59). VAPA-OSBP interaction is also required for sphingomyelin (SM) biosynthesis (60-62).

IFITM3's role in bacterial infections is poorly understood. A recent report found that an IFITM3 promoter polymorphism reduced transcriptional activity was associated with susceptibility to TB in Han Chinese children (63). In the C57BL/6 mouse model, no difference in MTb H37Rv lung burden was reported between wild-type and Ifitm3$^{-/-}$ C57BL/6 mice in the first 30 days after aerosolized MTb infection (64), although the relevance of this study to human TB is unclear, as C57BL/6 mice may poorly reflect the human inflammatory response (65). IFITM3 has also been found to associate with components of the vacuolar proton ATPase (v-ATPase) and promote the recruitment of the v-ATPase into endosomes/phagosomes (66). Notably, the v-ATPase is required for acidification of the phagosome, and MTb actively excludes the v-ATPase from the phagosome (67), which promotes virulent MTb survival and is a necessary precursor to MTb expansion in infected myeloid cells. Intriguingly, evidence suggests that MTb inhibition of phagosome maturation may not be complete, and that some organisms can delay maturation long enough to undergo transcriptional reprogramming, leading to a dormant, less drug-susceptible state that can persist in the hypoxic granuloma (68). A major problem with current treatment efforts for latent TB involves poor killing of such dormant bugs. New therapies that could overcome MTb-mediated phagosome maturation delay might preclude the development of these latent forms.

Data demonstrate that MTb infection of THP-1 monocytic cells (FIG. 10A) induces IFITM3 gene expression. In turn, stable knockdown of IFITM3 in THP-1 cells (FIG. 10B) markedly enhances growth of an H37Rv MTb strain that expresses the fluorescent reporter mCherry (mCherry-MTb) (69) (FIG. 10B-10C), a finding confirmed by colony forming unit (CFU) assay with wild-type H37Rv MTb (FIG. 10E). Furthermore, no difference in MTb uptake in cells transduced with control or IFITM3 shRNA (measured after puromycin killing of extracellular mycobacteria 3 hours post-MTb infection) (data not shown) was found, indicating that IFITM3 functions to restrict MTb infection at a post-uptake step. To extend the biological significance of these results, the ability of different MTb strains to induce IFITM3 mRNA in human MDM was tested. As shown in FIG. 10F, clinical MTb strains HN878 and CDC1551 also induce IFITM3 mRNA synthesis, although they vary in strength as inducers of IFITM3. IFITM3 knockdown also inhibited replication of a single-cycle HIV infectious clone that encodes EGFP in THP-1 cells (70) (FIG. 10D).

Based on these data, IFITM3 may be a critical modulator of containment of TB and HIV co-infection in the human host. Furthermore, given that IFITM3 functions in host lipid synthesis and v-ATPase recruitment to the maturing phagosome, IFITM3 may restrict MTb growth and latency establishment by modulating lipid incorporation into cellular membranes and increasing phagosome acidity, respectively, leading to enhanced phagosome maturation and mycobacterial degradation.

Role of IFITM3 in Regulation of TB/HIV Co-Infection in Primary Human Cells

IFITM3 expression in human MDM and AM may play an important role in restricting MTb/HIV co-infection. Two distinct full-length HIV subtype B infectious molecular clones of different cellular tropism that express ZsGreen1 are employed, which allows one to visualize HIV infection/replication by FACS even at early time points post-co-infection (FIG. 11A-11B), along with mCherry-MTb (FIG. 10C). Specifically, HIV$_{BAL}$ (R5-tropic) and HIV$_{LAI}$ (X4-tropic) that express ZsGreen1 in a 2A-fusion protein with Nef (FIG. 11A) are used, in a PBMC assay system that includes primary MDM where IFITM3 is ablated. A modified lentiviral vector (parent pLKO.1) that encodes the fluorescent reporter E2-Crimson are also constructed, which is a far-red emitter, allowing for simultaneous detection of cells expressing the IFITM3 shRNA (or, as described below, an expression vector encoding IFITM3), ZsGreen1-HIV, and mCherry-MTb. A similar vector encoding EGFP is used to transduce primary human monocytes, which are notoriously difficult to transduce, with good efficiency using high MOI$^+$ spinoculation. The feasibility of this technique has been demonstrated before.

Briefly, monocytes are isolated from peripheral blood by magnetic selection (StemCell Technologies). >95% purity of CD14$^+$ monocytes can be routinely obtained. These cells are differentiated with GM-CSF (50 ng/ml) for six days to make MDM. Next, the IFITM3-specific shRNA sequence used to successfully knock down IFITM3 expression in THP-1 cells (FIG. 10B) are cloned into the E2-Crimson lentiviral vector and MDM will be transduced at high MOI as shown in FIG. 12. Ablation of IFITM3 is confirmed by measuring mRNA and protein levels by quantitative PCR (qPCR) and western blotting, respectively. After 48 hours, IFITM3-ablated MDM are divided into two portions. The first portion of MDM are used directly to examine IFITM3 regulation of MTb and HIV infection, while the second portion of MDM are reconstituted with autologous cells from the same initial PBMC sample. The cultures are then mock-infected or infected with dual-tropic HIV$_{BAL}$ZsGreen1 (for MDM alone) or either HIV$_{BAL}$ZsGreen1 or T-tropic HIV$_{LAI}$Zs-Green1 (for MDM$^+$PBMC) at 50 TCID$_{50}$ and, after 24 hours, mock-infected or infected with mCherry-MTb at a 1:10 ratio of bacteria to cells. Cells are harvested at 2, 4, and 7 days post-MTb infection (in order to analyze the kinetics of infection at early, intermediate, and later stages), stained with fluorescently conjugated antibodies to CD3, CD4, and CD14, and analyzed by FACS to detect ZsGreen1, mCherry, and E2-Crimson levels in individual macrophages and ZsGreen1 levels in CD4$^+$ T cells. In each experiment, a portion of cells are retained for CFU analysis to quantitatively assess MTb levels in parallel with the FACS analysis.

Specifically, at the time of harvest for FACS, cells are lysed and sonicated, and serial dilutions are inoculated in Middlebrook 7H11 agar in triplicate, with colony analysis on day 25.

In a second approach the impact of constitutive IFITM3 overexpression in MDM on MTb/HIV co-infection is determined. Exogenous proteins are routinely overexpressed in cell culture (71). The human IFITM3 coding sequence under the control of the EF1α promoter are cloned into the E2-Crimson lentiviral vector for easy detectability by cytometry of transduced IFITM3+ cells. The IFITM3 overexpression vector (or a control vector lacking the IFITM3 coding sequence) is used to transduce MDM, which are then cultured and infected with HIV and MTb as above, followed by FACS analysis and CFU measurement. IFITM3 overexpression is compared to endogenous IFITM3 levels after MTb infection or IFN treatment by western blotting to confirm that physiologic levels of "stimulus-induced" IFITM3 are obtained.

In the event that manipulation of IFITM3 levels affects HIV and MTb growth and replication in MDM and/or in the reconstituted PBMC cultures, the analysis can be expanded to include primary isolates of HIV subtypes C and AE, which are dominant in regions of endemic TB (72) and routinely used (47, 50, 53), to ascertain the spectrum of IFITM3 anti-HIV activity. Briefly, MDM/PBMC cultures transduced with vectors encoding control shRNA, IFITM3 shRNA, or IFITM3 cDNA are infected with HIV$^{IN22}$ (R5; C subtype), HIV$_{92TH64}$ (X4; E subtype) or HIV$_{92TH03}$ (R5; E subtype). 24 hours after co-infection with wild-type MTb H37Rv at a 1:10 ratio of bacteria to cells, supernatants will be harvested after 4, 7, and 10 days, and viral replication are measured by standard p24 ELISA (Perkin Elmer).

In a complementary approach, the findings in MDM are confirmed to reflect what is occurring in AM. Excess fluid is obtained from BALs performed on healthy, adult, HIV-negative, consenting volunteer subjects. These individuals have normal spirometry, are non-smokers, and have no active pulmonary disease. From each pooled lavage, typically ~20-30×10$^6$ AM that are 98% viable as determined by trypan blue dye exclusion and by 95% positive nonspecific esterase staining (73-75) are obtained. From each donor, AMs are isolated by CD14+ bead selection (see above) and T cells by CD3-negative bead selection (StemCell Technologies). After transduction of AM with mock, IFITM3 shRNA, or IFITM3 overexpression lentiviral vectors, T cells are returned to half of the culture at a 1:1 T cell to AM ratio. After 48 hours, ZsGreen1-HIV and/or mCherry-MTb infections are performed on the AM alone and the AM+T cell cultures as described above. The impact of deletion or add-back of IFITM3 upon MTb are assessed by FACS and CFU analyses at 2, 4, and 7 days post-MTb infection.

IFITM3 knockdown may significantly increase MTb and R5-tropic HIV infection and that IFITM3 overexpression may significantly decrease MTb and R5-tropic HIV infection of MDM and AM alone or with autologous T cells during single and dual infection. In addition, IFITM3 ablation in macrophages may also enhance both X4- and R5-tropic HIV replication in autologous CD4+ T cells, most likely due to elevated levels of MTb-induced proinflammatory factors produced by MTb-infected MDM that drive HIV replication as previously shown (76). The converse may be true when IFITM3 is overexpressed in MDM. Finally, these experiments can provide a detailed analysis of the importance of IFITM3 in host regulation of MTb/HIV co-infection in a physiological ex vivo model system using both lab-adapted and primary HIV isolates.

Signal Transduction Pathways Involved in MTb Regulation of IFITM3 Gene Expression The classical transcriptional activator of IFITM3 is type I IFN, which signals via induction of IFN-inducible transcription factors that bind to an interferon stimulated response element (ISRE) located in the IFITM3 gene's core promoter (42-44), although IFN-γ also induces IFITM3 transcription (42-46). The finding that MTb infection induces IFITM3 expression in myeloid cells (see FIG. 10) expands the repertoire of potential signaling pathways capable of inducing expression of this host factor. To begin to delineate the cellular factors involved in MTb regulation of IFITM3 transcriptional activation, the role of the TLR signaling molecules MyD88, IRAK-1, and TRAF6 (77) is next probed. As shown in FIG. 13A, shRNA ablation of each of these factors in THP-1 cells modestly, but significantly, inhibits MTb-induced IFITM3 mRNA synthesis. Further investigation revealed that both the TLR2 agonist Pam3Cys and the TLR4 agonist LPS drive enhanced IFITM3 transcription in THP-1 cells, with LPS showing somewhat greater enhancement (FIG. 13B). Both TLR2 and TLR4 are activated by MTb (78). IFITM3 mRNA was also not induced by treatment with TNF or MCP-1, but was, as expected, strongly induced by IFN-γ (data not shown).

Interestingly, in murine macrophages, TLR4 activation, but not TLR2 activation, results in IFN-β synthesis and STAT1 activation (79), and MTb infection leads to TLR2- and TLR4-independent IFN-β production and STAT1 activation (80). Intriguingly, overexpression of STAT1 homodimers in a human hepatoma cell line resulted in significantly increased IFITM3 expression (81). The role of STAT1 in MTb infection is complex. While STAT1 homodimers form in response to IFN-γ signaling and promote mycobacterial control in myeloid cells, STAT1 forms a complex with STAT2 and IRF9 in response to type I IFN signaling, and this heterotrimeric transcription factor drives the expression of factors that restrain the immune response to MTb such as IL-10 (82-87). Because IFITM3 is potently induced by both type I and type II IFNs, demonstration that MTb induces IFITM3 mRNA synthesis via STAT1 induction/activation would identify a host target that restrains MTb growth/latency in the presence of signals that both enhance and impair the host response to MTb infection. To determine the importance of STAT1-dependent MTb induction of IFITM3, a series of STAT1-specific shRNA lentiviral vectors (sequences provided by Open Biosystems) is tested. After validation of at least two unique shRNAs that knock down STAT1 protein expression by >80% in THP-1 cells, studies are extended to MDM and AM, using the E2-Crimson lentivirus to deliver the STAT1 shRNAs. Briefly, MDM and AM are transduced with control shRNA or STAT1-specific shRNA E2-Crimson lentiviral vectors and, 48 hours after transduction, E2-Crimson+ cells are sorted, allowed to recover and attach for 24 hours, and then infected with MTb (strain H37Rv) at a ratio of 1:1 bacteria to cells. At 4, 8, 24, and 48 hours post-transfection, total RNA and protein are harvested and IFITM3 mRNA levels are measured by qPCR and IFITM3 protein levels are assayed by blotting. Cyclophilin B are used as a housekeeper for these analyses, as it was found to not be affected by TLR activation (88).

The role of surface receptors upstream of STAT1 (or other possible downstream intermediaries) on MTb-induced IFITM3 gene expression is characterized. Because all type I IFNs signal through the IFN-α receptor (IFNαR), the effect of ablating the IFN-α receptor subunit 1 (IFNaR1) transcripts with shRNAs targeting the receptor is tested, which is validated according to the techniques described above.

These shRNAs are used to transduce MDM and AM, and IFITM3 mRNA and protein expression in response to MTb infection of E2-Crimson⁺/IFNaR1 shRNA⁺ cells are measured. Second, MDM or AM are treated with antibodies to IFNα and IFNβ at a range of concentrations between 1-10 µg/ml just prior to infection with MTb (H37Rv) at a 1:1 bacterium to cell ratio, and IFITM3 mRNA/protein are quantitated at 6, 24, and 48 hours post-infection. All antibodies are first titered on MDM or AM from two different donors to determine concentrations that do not affect cell viability. Neutralizing antibodies have been successfully used to IL-6, TNF, and MCP-1 to demonstrate strain-specific MTb activation of HIV replication in PBMC, and to demonstrate the impact of MTb-specific CD4⁺ T cell responses on HIV replication (38, 76). To next determine the importance of TLR4 signaling on IFITM3 upregulation during MTb infection, two complementary approaches are used. First, MDM or AM are treated with the highly specific TLR4 signaling inhibitor CLI-095 (Invitrogen) at concentrations ranging from 50 nM to 1 for 1 hour, and then the cells as described are infected with H37Rv-MTb as described above. As a positive control for the experiments and to verify CLI-095 efficacy, cells are stimulated with the TLR4-specific agonist LPS at 100 ng/ml after CLI-095 treatment; LPS-stimulated TNF mRNA levels should be blocked by CLI-095. Second, the cells are treated with neutralizing antibodies to TLR4 and perform treatment, infection, and IFITM3 measurement as described above.

Finally, the importance of IFITM3 in differential regulation of HIV replication is investigated by the clinical MTb isolates HN878 and CDC1551. It was previously reported that CDC1551 drives significantly higher replication of HIV subtype B, C, and E viruses in PBMC as compared to HN878, and this was due in part to higher levels of TNF, IL-6, and MCP-1 synthesis (76). As shown in FIG. 10F, the clinical isolate HN878 induces ~3-fold greater IFITM3 mRNA synthesis in MDM as compared to the clinical isolate CDC1551, while the lab-adapted strain H37Rv drives even higher levels of IFITM3 transcription. Intriguingly, HN878 has been shown to induce markedly higher type I IFN expression in human cells in vitro and in MTb-infected mice as compared to infection with CDC1551 (89, 90). Based on these data, increased levels of IFITM3 in response to HN878 versus CDC1551 infection may contribute to the reduced HIV replication in HN878 co-infected cultures. MDM and AM are transduced with the E2-Crimson control or IFITM3-specific shRNA lentivirus. After 48 hours, cells are left untouched or reconstituted to PBMC, infected with $HIV_{BAL}$-ZsGreen1 (for MDM/AM) or $HIV_{BAL}$ZsGreen1 and $HIV_{LAI}$ZsGreen1 at 50 $TCID_{50}$ (for MDM/AM⁺PBMC) and, after 24 hours, mock-infected or infected at a 1:10 ratio of bacterial to cells with CDC1551, HN878 or H37Rv. At 48, 72, and 96 hours post-MTb infection, viral replication are monitored by FACS.

Inhibition of STAT1 in both MDM and AM is expected to block MTb-induced IFITM3 expression, and that suppression of MTb-induced IFITM3 expression may occur when type I IFN signaling is blocked. Inhibition of TLR4 signaling is expected to partially inhibit MTb induction of IFITM3. If IFITM3 levels are unchanged in response to MTb infection when TLR4 signaling is blocked, this would suggest that additional PRRs triggered by MTb that depend on MyD88/IRAK1/TRAF6, such as TLR9 or the IL-1β receptor, contribute to IFITM3 transcriptional activation by MTb (91) rather than a STAT1-dependent pathway. In this case, these possibilities are investigated with a combination of approaches targeting these molecules/pathways as described above, including neutralizing antibodies, agonists, and shRNA. Finally, IFITM3 knockdown, as well as STAT1 knockdown, is expected to result in greater enhancement of HIV replication in MDM/lymphocyte and AM/lymphocytes cultures when viral infection is performed in combination with HN878 infection as compared to CDC1551 infection, demonstrating that IFITM3 can differentially modulate viral replication in response to distinct clinical isolates of MTb. These experiments provide insight on how MTb strain-specific regulation of IFITM3 contributes to HIV replication, which has direct clinical relevance in regions where unique MTb strains are endemic and HIV infection rates are high. IFITM3 may also contribute to control of MTb by limiting its capacity to shift to a dormant phenotype. Thus, the findings here also define signaling mechanisms that are important for the expression of an important host factor that blocks establishment of MTb latency.

Cellular Mechanisms Involved in IFITM3-Mediated Restriction of MTb Infection

There is a growing appreciation of the role of IFITM3 in disrupting endosomal trafficking of enveloped viruses after cellular entry, including HIV (15-17, 47, 56, 92, 93). A critical facet of virulent MTb survival and subsequent establishment of latency at the site of infection is its ability to impede maturation of the phagosome in which it resides, preventing lysosome fusion and acid-based killing (94, 95). IFITM3-mediated control of endosomal trafficking and acidification can be a key mechanism involved in its inhibition of MTb growth and persistence in infected macrophages.

As noted above, one mechanism for IFITM3-mediated antiviral activity against influenza and VSV appears to be IFITM3's ability to disrupt the VAPA-OSBP interaction (59), which is required for biosynthesis of sphingomyelin (SM) (60-62), an essential component of lipid rafts (96). Rafts are critical for MTb infection of macrophages, as the MTb-encoded surface molecule, glycolipid mannose-capped lipoarabinomannan (ManLAM), inserts into host cell lipid raft microdomains, promoting the inhibition of MTb phagosomal maturation by blocking delivery of lysosomal components from the trans-Golgi network to the MTb phagosome (94, 97, 98). Lipid rafts are also involved in MTb infection of another cell type found in the lung space—alveolar epithelial cells (AEC) (99). AEC are critical targets of MTb during pulmonary disease and evidence is growing that they may be a major contributor to pathogenesis in the lung. For example, MTb infection of AEC results in lower levels of apoptosis and higher levels of necrosis than is seen in MTb-infected alveolar macrophages (100, 101). Moreover, IFITM3 is potently induced by type I IFN in AEC (102).

Because MTb requires lipid rafts for productive infection of macrophages and AEC, and because IFITM3 disruption leads to accumulation of MTb in monocytes (FIG. 10C), one mechanism underlying IFITM3 inhibition/control of MTb infection may be its suppression of cellular SM levels, leading to raft impairment and decreased MTb intracellular survival. The effects of IFITM3 knockdown/overexpression on MTb intracellular trafficking are first determined in the human AEC cell line A549, which has been extensively used for analysis of MTb infection in vitro (101, 103, 104), and which forms a tight monolayer on tissue culture surfaces, allowing for microscopic imaging that is difficult with cell lines in suspension such as THP-1 cells. Indeed, A549 cells have also been used to microscopically characterize IFITM3's role in blocking West Nile Virus replication (47). Briefly, A549 cells are grown to confluence on coverslip-bottom dishes (for microscopic visualization). Forty-eight hours after transduction with control, IFITM3 knockdown, or IFITM3-overexpressing lentiviral vectors, the cells are infected with mCherry-MTb (at 1:1, 5:1, and 10:1 bacteria to cell ratios). At 15 min, 30 min, 1 hr, 2 hr, 4 hr, and 8 hr after infection cells are fixed with 1% paraformaldehyde, permeabilized with 0.2% Triton X-100, and stained with Alexa488-conjugated antibodies to the early endosomal marker Rab5, the late endosomal markers Rab7 and CD63, or the lysosomal markers LAMP-1 and LAMP2 (105-107). Co-localization of mCherry-MTb and the endosomal/lysosomal markers are determined by confocal microscopy.

Manipulation of IFITM3 levels may affect SM synthesis, A549 cells transduced with IFITM3 shRNA, IFITM3-overexpressing, or the control vectors are lysed in hypotonic buffer and, after removal of nuclei by centrifugation, SM levels are measured using a standard SM colorimetric assay (Abcam). At the same time, the hypothesis that IFITM3 is a critical mediator of lipid raft assembly can be tested by directly examining the effect of low or high intracellular IFITM3 levels on lipid raft content in host cell membranes. Rafts are isolated from the control, IFITM3 knockdown, and IFITM3-overexpressing A549 cells using a hypotonic lysis/density gradient procedure described previously (108), and raft levels are measured by SDS-PAGE/blotting of the raft-associated markers Ras and Gq. Total cell lysates are used to normalize for protein levels, and blotting of the transferrin receptor control for non-raft contamination (108).

As described above, MTb impairs incorporation of the v-ATPase into the maturing phagosome, and IFITM3 has been shown to promote recruitment of the v-ATPase complex to phagosomes. Lewis et al. have defined a set of five MTb transcripts that are strongly associated with establishment of a dormant state, persistence, and drug tolerance (109). Here the hypothesis that IFITM3 regulates the establishment of this transcriptional pattern associated with mycobacterial persistence in AM is tested. AM are first infected transduced with the control IFITM3-overexpressing, or IFITM3 shRNA vectors and, at 1, 2, 4, 8, 24, and 48 hours post-MTb-infection, transcript levels of the five dormancy genes (Rv0215c, RV1152, Rv2497c, Rv2517c, and Rv3290c) are quantitated. To mechanistically link IFIMT3 levels to restriction of dormancy establishment, control and IFITM3 knockdown or IFITM3 overexpressing A549 is transduced with a lentiviral vector encoding the v-ATPase subunit H protein fused to GFP based on the approach described by Wong et al (67). After stable expression is obtained, these cells are infected with mCherry-MTb and co-localization of MTb and the v-ATPase are ascertained over time by confocal imaging: MTb trafficking to late endosomal and lysosomal compartments is expected to be reduced when IFITM3 is ablated in A549 cells, and that trafficking to lysosomal compartments is expected to increase when IFITM3 is overexpressed. This would demonstrate a novel role for IFITM3 in promoting MTb phagosome maturation and provide a mechanism for the first direct biological evidence for IFITM3 in controlling a bacterial infection. In addition, there may exist a direct link between IFITM3 expression and impaired OSBP-VAPA-mediated SM biosynthesis resulting in perturbation of raft organization. Finally, IFITM3 ablation is expected to result in increased mycobacterial transcripts associated with the switch to dormancy, and that this process can correspond to reduced v-ATPase incorporation into the maturing MTb-containing phagosome. Such findings would demonstrate that IFITM3 plays multiple roles in restricting MTb growth and persistence in infected myeloid cells of the lung, and would underscore its promise as a therapeutic target for i) improved control of MTb during the early stages of infection and ii) reducing the dormant mycobacterial population in the lung that persist during latent TB, which may expedite sterile clearance of latent organisms in combination with isoniazid or other therapies. As the data indicate IFITM3 is also a potent modulator of HIV infection, targeting this host factor may even have a synergistic effect in cases of TB/HIV co-infection—both pre- and post-TB reactivation.

Mechanisms of NTZ Regulation of TB/HIV Co-Infection

The FDA first approved NTZ in 2004 for the treatment of both *Giardia*- and *Cryptosporidium*-associated diarrhea (110), and it has been safely used in $HIV^+$ patients (23, 111). Recently, it has been shown to have efficacy in the treatment of uncomplicated influenza (20), and addition of NTZ to the standard HCV treatment regimen of ribavirin plus pegylated IFN can significantly improve HCV virological response (22). Because NTZ has been used safely and effectively in many different patient populations, including children, identification of mechanisms underlying its action, as well as its host targets over and above its direct effect upon organisms is of great value.

While cytotoxic T cell responses play a critical role in preventing MTb escape from the granuloma, there is extensive evidence that local hypoxic conditions in granuloma microenvironments lead to persistence of "dormant", nonreplicating mycobacteria that readily adapt to these conditions by changing metabolic requirements (112). Indeed, because isoniazid chemotherapy predominantly kills replicating mycobacteria, it has been suggested that the long treatment window required for putative MTb clearance from the lung is due to the poor activity of INH against these nonreplicating organisms (113). Notably, Nathan and colleagues demonstrated that NTZ is a potent killer of nonreplicating MTb in culture (114). Indeed, at human physiological doses (16 µg/ml), NTZ reduced viable, nonreplicating MTb (initial inoculum of 108 CFU/ml to mimic mycobacteria concentrations found in cavitary lesions) by over 2 log units over four days, and this effect was stronger than what was seen with replicating MTb. In addition, no evidence of resistance mutants was found even when extremely high inocula were used for experiments. Thus, NTZ is a promising agent for treatment of latent TB infection, and efforts to examine its molecular mechanisms in more physiological ex vivo model systems and its effects upon host responses, particularly in the context of HIV, are needed.

NTZ also influences host responses. For example, NTZ suppresses MTb proliferation in cell cultures by inhibiting the mammalian target of rapamycin (mTOR) pathway, leading to activation of autophagy (115). One target of NTZ that may contribute to its anti-HCV effects is the double-stranded RNA-activated protein kinase (PKR), as a recent report showed that NTZ induces autophosphorylation of PKR in a hepatoma cell line (116). PKR activation, in turn, amplifies the IFN response by: i) activating the NF-KB, p38, JNK, and STAT1/3 pathways, resulting in transcription of genes involved in the antiviral response such as IFN-β and TNF; and ii) suppressing general mRNA translation via phosphorylation and inhibition of eIF2α (117-119). PKR activation also promotes autophagy by inducing eIF2α-mediated phosphorylation of LC3 (118, 120), which promotes LC3 association with bacterial phagosomes leading to phagosomal maturation and bacterial degradation. Therefore, NTZ could promote autophagy via PKR activation in addition to its effects on mTORC1.

It was discovered that NTZ enhances gene expression of IFITM3 (FIG. 14A) and the HIV restriction factor SAMHD1

(FIG. 14B) in MDM. Furthermore, when similar NTZ concentrations to those shown to inhibit MTb growth in liquid cultures is used, it was shown that mCherry-MTb infection of THP-1 cells is inhibited by NTZ (FIG. 15A). It was also found that pretreatment of human MDM at much lower concentrations (1 µM) of NTZ suppresses $HIV_{BAL}Z$-sGreen1 infection of MDM (FIG. 15B). Since new treatments for latent and/or active TB that target host factors should not lead to immune activation that augments HIV transcriptional activation or reactivation of HIV-1 from the viral reservoir, the effect of NTZ on the reactivation of a silent, integrated HIV subtype C minigenome in THP-1 cells is also (FIG. 16). Pretreatment of the cells with NTZ at 5 or 10 µM for 1 hour prior to stimulation with the TLR2 agonist Pam3Cys or with Sendai virus infection inhibited HIV transcriptional activation (FIGS. 16B and 16C). NTZ may inhibit MTb replication via induction of IFITM3, and NTZ inhibits MTb-stimulated HIV-1 replication at early post-entry and transcriptional steps via its modulation of the host factors IFITM3, SAMHD1, and PKR.

Involvement of IFITM3 in NTZ Inhibition of MTb Replication

To mechanistically link NTZ's inhibitory effect upon MTb growth in monocytes with its induction of IFITM3, wild-type THP-1 cells and THP-1 IFITM3 deficient cells are pretreated with NTZ (10, 15, and 20 µM) and infected with mCherry-MTb as described above. A portion of the cells are analyzed by FACS as shown in FIG. 15, and a portion by CFU, to examine and confirm the requirement of IFITM3 for NTZ's inhibition of MTb growth. The role of IFITM3 in NTZ's effect in primary MDM and AM where IFITM3 is knocked down using the IFITM3-specific shRNA E2-Crimson lentiviral vector is confirmed. The dormancy-related transcripts in IFITM3hi and IFIMT3lo AM that have been pre-treated with NTZ and infected with MTb as described above are measured in order to determine whether NTZ can also limit metabolic changes in MTb that lead to increased mycobacterial persistence, and the requirement for IFITM3 in this process.

Mechanisms Involved in NTZ Inhibition of Early Steps of HIV Entry

SAMHD1 was identified in 2011 as a restriction factor that inhibits HIV reverse transcription in primary myeloid cells and resting $CD4^+$ T cells by hydrolyzing cytoplasmic dNTPs (121-128). It has recently been shown that SAMHD1 is regulated by phosphorylation at threonine 592 by cyclin A2/CDK1, and that this phosphorylated form of SAMHD1 fails to restrict HIV infection (129, 130). Intriguingly, IFN-β treatment of PBMC reduces SAMHD1 phosphorylation, providing another mechanism for type I IFN suppression of HIV infection (129). A recent ex vivo study found that NTZ synergizes with glucocorticoids to suppress X4-tropic HIV replication in human PBMC by inhibiting a step between release of viral components into the cytoplasm (post-fusion) and reverse transcription (131). Intriguingly, this is a step in the viral life cycle where SAMHD1 also acts. NTZ-mediated enhancement of IFITM3 and SAMHD1 levels and/or activity of SAMHD1 may lead to suppression of HIV infection at an early post-entry step in both MDM and AM, and that this antiviral effect may occur even in the context of MTb co-infection in ANT/lymphocyte cultures.

To determine whether IFITM3 is important for NTZ's suppressive effect on HIV, or if NTZ works via an IFITM3-independent mechanism, the E2-Crimson lentiviral IFITM3 shRNA knockdown protocol is employed to ablate IFITM3 in MDM. Forty-eight hours after control or IFITM3 shRNA transduction, cells will be treated with NTZ at 0, 2, 4, or 8 µM for 30 min, washed, and infected with $HIV_{BAL}ZsGreen1$ at an MOI of 1. At 3, 5, and 7 days post-infection, $ZsGreen1^+$ cells and ZsGreen1 levels per cell are detected by FACS. As current literature suggests a role for IFITM3 in inhibition of HIV, NTZ-enhanced IFITM3 may be at least partially responsible for NTZ's suppressive effect upon HIV. The mechanisms involved in NTZ induction of IFITM3 gene expression can be defined, using AMs as well as MDM to expand the physiological relevance of the experiments. Specifically, because IFITM3 is an ISG, the relative importance of IFN-independent and IFN-dependent processes in the induction of IFITM3 expression by NTZ is examined. Freshly isolated MDMs and AMs are treated with 0, 2, 4, or 8 µM of NTZ for 8, 24, or 48 hours in the presence or absence of neutralizing antibodies to IFN-γ, IFN-α and/or IFN-β and RNA and protein fractions are isolated to analyze IFITM3 mRNA and protein levels, respectively.

It is next determined if NTZ treatment affects the SAMHD1 phosphorylation status of SAMHD1 using the method described by Cribier et al., whereby proteins are separated on a Phos-tag acrylamide gel (Waco Pure Chemical Industries). This allows resolution of phosphorylated and unphosphorylated versions of the protein of interest, which can then be detected via standard anti-SAMHD1 western blotting (129). Finally, SAMHD1 in MDM and AM is knocked down using shRNA to SAMHD1 that were validated in THP-1 cells (FIG. 17A); SAMHD1- or control knockdown MDM and AM are treated with NTZ, infection with $HIV_{BAL}ZsGreen1$, and $ZsGreen1^+/E2$-$Crimson^+$ cells are analyzed.

Because MTb drives enhanced HIV replication in MDM and AM in the context of autologous activated lymphocytes (37), it is important to determine whether NTZ-mediated enhancement of IFITM3 and SAMHD1 in this ex vivo system is able to overcome MTb-induced HIV replication. To address this issue, after transduction of MDM and AM with the control, IFIMT3-, or SAMHD1-specific shRNA E2-Crimson lentiviruses and reconstitution with autologous lymphocytes, the cells are treated with 0, 2, 4 or 8 µM of NTZ. This is followed by infection with $HIV_{BAL}ZsGreen1$ or $HIV_{LAI}ZsGreen1$, followed by mCherry-MTb. Viral growth is then be followed by FACS at 2, 4, and 7 days after infection.

NTZ induction of IFITM3 is expected to be an important mechanism in NTZ's inhibition of MTb growth. NTZ-induced IFITM3 and SAMHD1 in MDM and AM is expected to inhibit productive HIV infection at early post-entry steps, as these host factors have been linked to inhibition of viral membrane fusion and reverse transcription, respectively. IFITM3 and SAMHD1 expression is expected to occur in two phases, with direct transcriptional activation of these genes followed by a secondary activation phase that is regulated by autocrine/paracrine IFN production, which is also promoted by NTZ. MTb augmentation of HIV replication in the MDM or AM/lymphocyte system is expected to be suppressed by NTZ, and that this effect is partially ablated by knockdown of IFITM3 and/or SAMHD1.

Role of PKR in NTZ's Inhibition of TB-Driven HIV LTR Activation

Given a previous report that NTZ activates PKR (116), which, as described above, promotes the synthesis of many different proinflammatory molecules, it is possible that NTZ might be problematic for treatment of TB/HIV co-infection if it promotes viral transcriptional activation or reactivation from latency. To address this issue, two THP-1 clones (termed THP-1/LTR-ZRT) are constructed and established that each contain a single integrated copy of an HIV subtype C "minivirus" (at different genomic sites) where ZsGreen1, *Renilla* luciferase (RLuc), and viral Tat expression are controlled by the viral LTR (diagrammed in FIG. 16A) and that are transcriptionally quiescent. The LTR in these clones is strongly activated by different stimuli, including the TLR2 agonist Pam3Cys, and Sendai virus, which signals through TLR3 and TLR9 (FIG. 16). Each THP-1 clone also possesses a stably integrated cassette that encodes firefly luciferase (FFLuc) and DsRed under the control of the GAPDH promoter, which provides an internal control for cell viability and off-target treatment effects. Notably, pretreatment of the THP-1/LTR-ZRT clones with NTZ for as little as 30 minutes significantly inhibits both Pam3Cys and Sendai virus activation of the integrated LTR-*Renilla* reporter gene (FIGS. 16B and 16C) and MTb infection (not shown). Thus, any NTZ activation of PKR in this system does not overcome the suppressive effects of this compound. Indeed, previous studies have shown that PKR inhibits full-length HIV transcription via phosphorylation of the cellular factor RNA helicase A (132), which, in its unphosphorylated form, binds the viral RNA TAR element, promoting transcript extension (133, 134). Although PKR also activates NF-κB (135), which is a critical player in nascent HIV transcription, the fact that RNA helicase A acts at a post-transcriptional step (TAR binding) suggests that any enhancement of nascent viral transcription induced by PKR activation may be mitigated by its ability to deactivate RNA helicase A. NTZ may inhibit MTb-stimulated HIV LTR reactivation through PKR, which, in turn, inhibits RNA helicase A-mediated viral transcriptional enhancement.

The ability of NTZ to activate PKR in the THP-1/LTR-ZRT clones is first established. The cells are treated with NTZ at 0, 2, 4, or 8 µM of NTZ for 30, 60, or 120 minutes and then processed for western blotting with antibodies directed against total PKR and PKR that is phosphorylated at threonine 451, which is the primary PKR autophosphorylation target residue (136)(Millipore). Antibodies directed against eIF2α that is phosphorylated at serine 51 (Cell Signaling Technology) are used, which is a PKR target residue. Based on the report in hepatoma cells (136), NTZ is expected to activate PKR in THP-1 cells, and that these experiments can provide a base from which to determine the importance of PKR for NTZ-mediated suppression of viral transcription using two complementary approaches. First, cells are treated with the specific PKR inhibitor C16 (Sigma) for 30 min, followed by NTZ for 30 min, and are mock-stimulated, or infected with Sendai virus (as a positive control for PKR activation) or MTb H37Rv at a ratio of 1:1 bacteria:cells. To determine the relative importance of PKR activation for NTZ-mediated inhibition viral transcription at the quantitative and per cell level, RLuc are assessed at 8 and 16 hours and ZsGreen1$^+$ cells will be detected by FACS. Second, the THP-1/LTR-ZRT clones are transduced with a PKR-specific shRNA lentiviral vector; two shRNA lentiviral vectors targeting PKR in THP-1 cells are generated (FIG. 17B). PKR knockdown in the THP-1/LTR-ZRT clones are verified by Western blotting. Control- and PKR-shRNA THP-1/LTR-ZRT cells will then be treated with NTZ for 30 min at the concentrations outlined above, infected with MTb or Sendai virus for 8 or 16 hours, and RLuc and ZsGreen1 levels are assayed.

It is next tested whether NTZ treatment interferes with RNA helicase A promotion of viral transcription. After NTZ treatment of the THP-1/LTR-ZRT clones and infection with MTb or Sendai virus, levels of overall and phosphorylated RNA helicase A are measured using the Phospho-tag acrylamide SDS-PAGE system and antibodies directed against RNA helicase A (Abcam). Next, an RNA-protein co-immunoprecipitation assay is adapted to detect RNA helicase A interaction with HIV TAR (134): THP1/LTR-ZRT clones are treated with 0, 2, 4, or 8 µM of NTZ for 30 min, infected with MTb or Sendai virus and, at 1, 2, 4 and 8 hrs, cells are fixed with 1% PFA, and lysed to obtain nuclei. Sonicated nuclei are precipitated with an RNA helicase A antibody (Abcam) and Protein G beads (NEB), washed, and total RNA are column-purified (Qiagen). RNA is reverse transcribed using random hexamers and primers flanking the TAR element are used to perform qPCR of the RNA helicase A pull-down product.

The data described herein are the first to suggest that NTZ regulates HIV at the transcriptional level. Thus, in addition to its effects on IFITM3 and SAMHD1 expression, this additional inhibitory mechanism is dependent upon another NTZ target—PKR. The fact that HIV is so sensitive to NTZ and is inhibited at very low doses as compared to TB suggests that these distinct pathways synergize in inhibition of the viral life cycle. Demonstration that NTZ inhibits viral RNA synthesis in response to MTb infection is particularly relevant for TB/HIV co-infection of latently HIV-infected myeloid cells, since it is important to ensure that any novel treatment involving host targets does not drive HIV. NTZ is expected to activate PKR in THP-1/LTR-ZRT cells, which, in turn, results in phosphorylation of RNA helicase A and diminished viral transcription due to reduced RNA helicase A recruitment to viral TAR. RNA helicase A promotes the replication of many viruses and is highly conserved in mammals (137-140), suggesting that NTZ may be an effective compound for suppressing diverse viruses via this mechanism. In the event that NTZ is not found to affect RNA helicase A phosphorylation and/or its recruitment to TAR, this would indicate that NTZ suppresses LTR activation through a different mechanism, perhaps by inducing expression of alternative soluble factors that can inhibit LTR stimulation. To address this issue, the effect of NTZ treatment on cytokine/chemokine production in PBMC using Luminex assays is determined, and ii) the effects of NTZ treatment on recruitment of transcription factors, including Sp1, NF-κB, and NFAT5, to the viral LTR secondary to MTb infection are determined by using chromatin immunoprecipitation (ChIP), allowing for "reverse identification" of pathways affected by NTZ in monocytes.

Ability of NTZ to Suppress TB/HIV Co-Infection Via its Induction of Autophagy

One mechanism by which MTb survives in infected cells is by its blocking the maturation of phagosomes into phagolysosomes (143). Thus, stimulation of autophagy can strongly inhibit MTb infection through circumvention of MTB's phagosome maturation block and the delivery of antimicrobial peptides to MTb-containing phagosomes (reviewed in (144)). Autophagy also inhibits HIV infection and MTb/HIV co-infection of macrophages (145-147), although HIV Nef is capable of blocking autophagosomal maturation and subsequent viral degradation by inhibiting beclin-1, which is critical for lysosome fusion with the autophagosome (148).

NTZ promotes autophagy in MTb-infected THP-1 cells and human monocytes through inhibition of NQO1, a quinone oxidoreductase, which leads to activation of the TSC1-TSC2 complex, disassembly of the mTORC1 complex, and activation of factors that contribute to autophagosome initiation (115). Among these activated factors is LC3, which marks early autophagosomes and is required for autophagic membrane expansion (149). Another critical mechanism of autophagy induction in response to viral infection involves PKR phosphorylation of eukaryotic initiation factor (eIF) 2α (120, 150). PKR phosphorylation itself has also been shown to promote autophagy initiation and LC3 accumulation in autophagosomal membranes during *Toxoplasma gondii* infection (151). PKR-mediated autophagy induction is repressed by STAT3 through direct protein-protein interactions between STAT3 and PKR (152). Indeed, viral Tat-mediated activation of STAT3 during HIV infection inhibits autophagy in bystander monocytes (153). Notably, several inducers of autophagy, such as palmitate and rapamycin, can overcome STAT3 block of autophagy by disrupting the STAT3-PKR interaction, thus freeing PKR to phosphorylate eIF2α and initiate autophagy (152). Based on these data, it is hypothesized that (i) NTZ promotes autophagy in human monocytes and AM via PKR-dependent activation, and that (ii) NTZ-induced autophagy inhibits MTb/HIV co-infection in the MDM/AM+lymphocyte culture system. It is also investigated whether NTZ inhibition of MTb/HIV co-infection partially depends on NTZ's ability to overcome STAT3 inhibition of PKR and associated autophagy repression.

To test the hypothesis that NTZ activates autophagy in a PKR-dependent manner, the effect of NTZ treatment on autophagy activation in PKR-deficient THP-1 cells (see FIG. 17) is first analyzed. Control and PKR shRNA THP-1 cells are treated with NTZ (0, 2, 4 or 8 μM) and, after 4, 8, or 24 hours, SDS-PAGE/western blotting are performed to quantify ratios to LC3B-I and LC3B-II (Abcam) since induction of autophagy results in conversion of cytosolic LC3B-I to membrane-bound LC3B-II, and these LC3B versions can be resolved by gel electrophoresis (154). Upon confirmation of a role for PKR in NTZ-induced autophagy in THP-1 cells, the importance of this pathway is next validated in MDM and AM, which is mock-treated or treated with the PKR inhibitor C16, and exposed to NTZ (0, 2, 4 or 8 μM). LC3BI/LC3B-II ratios are analyzed by blotting.

The importance of autophagy in NTZ inhibition of MTb/HIV co-infection is next ascertained in primary cells. Reconstituted MDM/AM+lymphocyte cultures are infected with $HIV_{BAL}$ZsGreen1 followed by mCherry-MTb infection. Two days post-MTb infection, cells are mock-treated or treated with MHY1485 (155)(Sigma), an inhibitor of activation of mTOR driven autophagy for 30 min, and then treated with NTZ (0, 2, 4 or 8 μM). HIV and MTb replication are measured by FACS (HIV and MTb), p24 assay (HIV), and CFU assay (MTb) at 2, 4, and 5 days post-NTZ treatment. Suppression of autophagy in this system by MHY1485 are verified by LC3B-I/LC3B-II blotting after co-treatment of the MDM or AM with the MHY1485 inhibitor combined with the autophagy inducer rapamycin, or co-treatment with MHY1485 and NTZ. These experiments can indicate how much of NTZ's inhibitory effect is due to autophagy versus other mechanisms.

Several inducers of autophagy, including rapamycin and palmitate, overcome constitutive autophagy inhibition by disrupting the STAT3 interaction with PKR. However, this outcome can be reversed by overexpression of STAT3 (152). Two approaches are used to test the hypothesis that NTZ activates autophagy by overcoming the STAT3 block of PKR. First, MDM and AM are treated with NTZ (0, 2, 4 or 8 μM) or rapamycin (1 μM) for 8 or 16 hours. Next, total protein is immunoprecipitated with antibody to STAT3 (Cell Signaling Technology) and Protein G beads (NEB). Immunoprecipitates are eluted and resolved by SDS-PAGE and blotted. PKR pulled down by the STAT3 antibody are detected with an anti-PKR antibody (Abcam) and normalized to the total STAT3 levels also precipitated. Second, MDM and AM are transduced with STAT3 overexpression or control E2-Crimson lentiviruses, returned to culture with autologous lymphocytes, and co-infected with $HIV_{BAL}$ZsGreen1 and mCherry-MTb. After 2 days, cultures are treated with NTZ (0, 2, 4 or 8 μM) or rapamycin (1 μM) and, at 2, 4, and 5 days post-NTZ treatment, cells are analyzed by FACS to ascertain $HIV_{BAL}$ZsGreen1 and mCherry-MTb replication in E2-Crimson+ AM.

PKR knock-down in THP-1 cells and chemical inhibition of PKR in MDM and AM is expected to block NTZ induction of autophagy, indicating that PKR activation by NTZ is an important mechanism of NTZ-induced autophagy. NTZ inhibition of MTb/HIV co-infection of MDM and AM/lymphocyte cultures is expected to be partially inhibited by pre-treatment of cells with the inhibitor of mTOR driven autophagy, MHY1485. These experiments may directly implicate autophagy induction in NTZ's anti-MTb/HIV effect. Finally, NTZ is expected to disrupt STAT3-PKR interaction in a dose-dependent manner, and that STAT3 overexpression in MDM and AM during MTb/HIV co-infection will reverse NTZ-mediated inhibition of both pathogens. Intriguingly, STAT3 activation has been linked to reduced host control of MTb in human cells ex vivo (156, 157). Thus, through elucidation of the impact of NTZ on STAT3-mediated inhibition of autophagy, NTZ is expected to overcome a negative host regulator of TB/HIV immunity, as well as augment the effects of positive inhibitors of co-infection such as IFITM3 and SAMHD1.

NTZ induces stress granule formation in A549 cells.

Figure 18A:
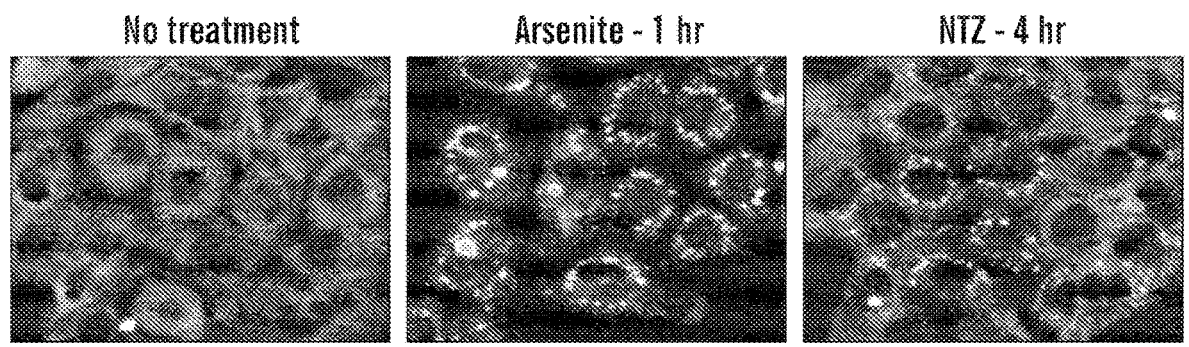

NTZ induces PKR autophosphorylation and PKR-mediated eIF2α phosphorylation (158, 159) indicates that a mechanism underlying NTZ's effect can also include induction of formation of cytoplasmic stress granules. Stress granules form in response to stress conditions, including pathogen infection and other environmental stressors; they are repositories for translationally stalled mRNA-ribonucleoprotein complexes that can rapidly initiate completed translation once the stress is relieved (160). PKR is one factor that has been directly implicated in the stress granule pathway, and evidence suggests that stress granules nucleated by the cytoplasmic factors G3BP1, G3BP2, and Caprin-1, form a platform for PKR activation (161, 162). In turn, active PKR phosphorylation of eIF2α enhances global protein synthesis downregulation and the assembly and maintenance of stress granules (163-171). As shown in FIG. 18A, when A549 alveolar epithelial cells were treated with 40 μM NTZ, the formation of stress granules was detected. Treatment with sodium arsenite, a classical activator of stress granules, was used as positive control.

Figure 18B:
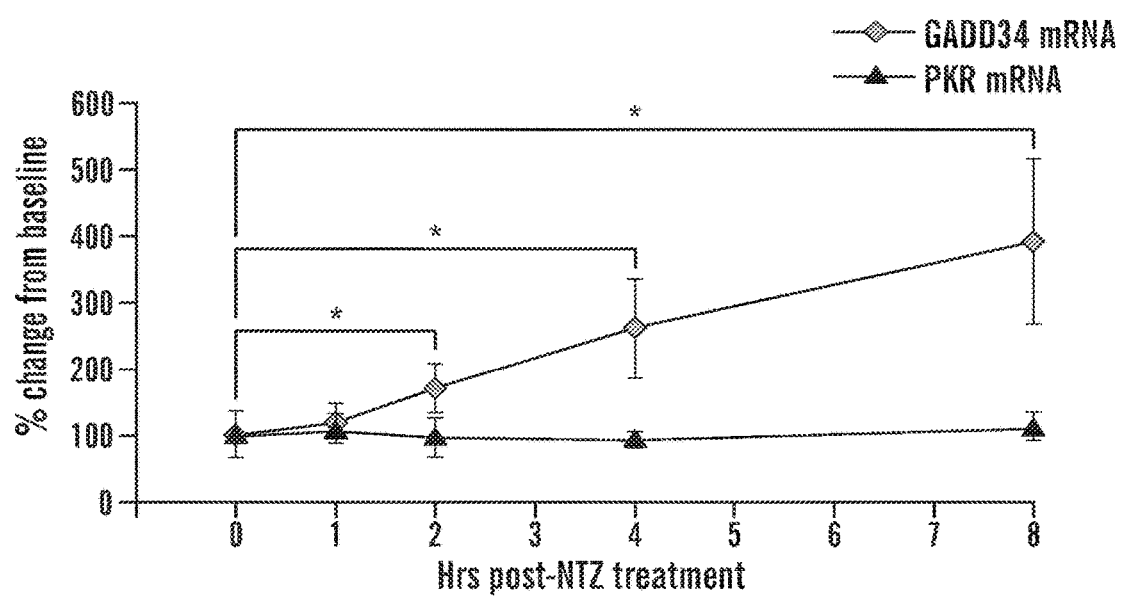
Figure 18C:
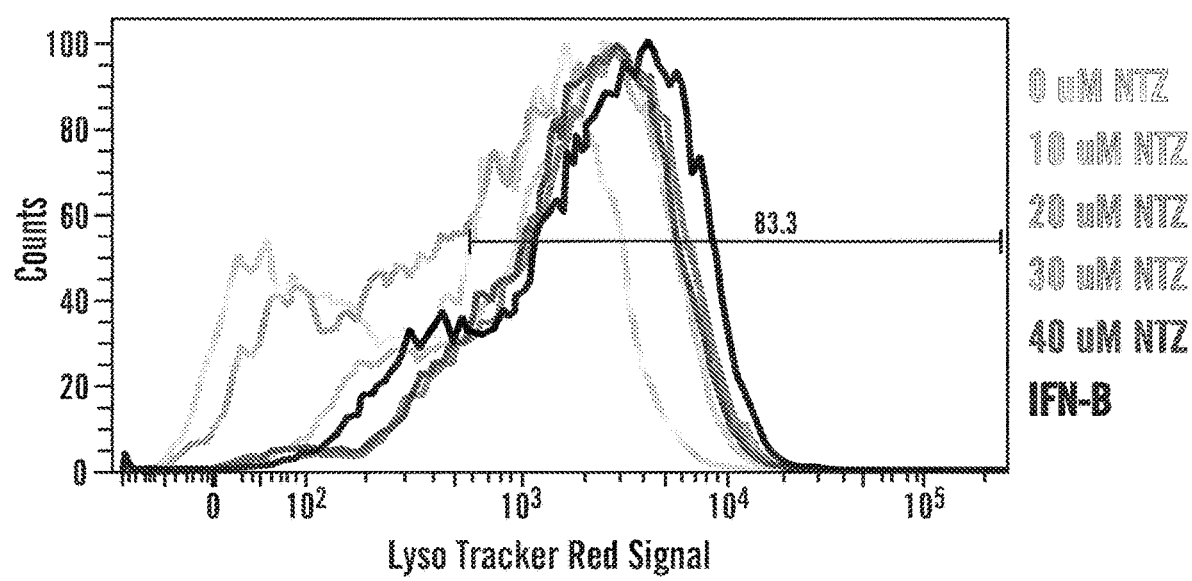

Of the genes that remain capable of being activated during eIF2α-induced translational shutdown, the phosphatase GADD34 is of major importance. GADD34 transcriptional activation is regulated by ATF4, which is directly activated by phosphorylated eIF2α (172). GADD34 is a phosphatase that functions in an auto-regulatory loop by dephosphorylating eIF2α, leading to the resumption of translation and ATF4/GADD34 downregulation unless the stressor persists (172-175). As shown in FIG. 18B, it was found that treatment of A549 cells with NTZ at the physiological concentration of 40 μM leads to significant induction of GADD34 mRNA expression. Moreover, NTZ treatment of THP-1 monocytic cells leads to increased intracellular acidity (FIG. 18C), further demonstrating this drug's effects on cytoplasmic compartments.

NTZ does not promote general inflammation.

To ensure that NTZ does not promote general inflammation that could be expected to be detrimental during treatment of viral infections, as well as conditions such as TB/HIV co-infection, the effect of NTZ on the reactivation of a latent HIV-1 subtype genome in two THP-1 monocytic clones in which this genome (which encodes the reporter ZsGreen1 as a readout of LTR activation) is silently integrated at different genomic sites was examines. As shown in FIG. 2, NTZ actually reduces LTR reactivation by both direct MTb infection (FIG. 19A) and in response to the potent TLR2 agonist Pam3Cys (FIG. 19B), indicating that NTZ does not exacerbate signaling in myeloid cells that leads to LTR activation, and, in fact, may actually dampen responses to these pattern recognition signals.

REFERENCES FOR EXAMPLE 3

1. Goldfeld A E, Delgado J C, Thim S, Bozon M V, Uglialoro A M, Turbay D, Cohen C, Yunis E J. Association of an HLA-D Q allele with clinical tuberculosis. Journal of the American Medical Association. 1998; 279:226-8.
2. Delgado J C, Baena A, Thim S, Goldfeld A E. Ethnic-specific genetic associations with pulmonary tuberculosis. J Infect Dis. 2002; 186(10):1463-8.
3. Delgado J C, Tsai E Y, Thim S, Baena A, Boussiotis V A, Reynes J M, Sath S, Grosjean P, Yunis E J, Goldfeld A E. Antigen-specific and persistent tuberculin anergy in a cohort of pulmonary tuberculosis patients from rural Cambodia. Proc Natl Acad Sci USA. 2002; 99(11):7576-81.
4. Delgado J C, Quinones-Berrocal J, Thim S, Miranda L F, Goldfeld A E. Diagnostic and clinical implications of response to tuberculin in two ethnically distinct populations from Peru and Cambodia. Int J Tuberc Lung Dis. 2004; 8(8):982-7.
5. Delgado J C, Baena A, Thim S, Goldfeld A E. Aspartic acid homozygosity at codon 57 of HLA-D Q beta is associated with susceptibility to pulmonary tuberculosis in Cambodia. J Immunol. 2006; 176(2):1090-7.
6. Flores-Villanueva P O, Yunis E J, Delgado J C, Vittinghoff E, Buchbinder S, Leung J Y, Uglialoro A M, Clavijo O P, Rosenberg E S, Kalams S A, Braun J D, Boswell S L, Walker B D, Goldfeld A E. Control of HIV-1 viremia and protection from AIDS are associated with HLA-Bw4 homozygosity. Proc Natl Acad Sci USA. 2001; 98(9):5140-5.
7. Delgado J C, Leung J Y, Baena A, Clavijo O P, Vittinghoff E, Buchbinder S, Wolinsky S,
Addo M, Walker B D, Yunis E J, Goldfeld A E. The −1030/-862-linked TNF promoter single-nucleotide polymorphisms are associated with the inability to control HIV-1 viremia. Immunogenetics. 2003; 55(7):497-501.
8. Goldfeld A E, Ranjbar S, Tsitsikov E N. Tuberculosis/human immunodeficiency virus coinfection and the host immune response. In: Kaufman S H E, Britton W J, editors. Handbook of Tuberculosis: Immunology and Cell Biology. Weinheim: Wiley-VCH; 2008. p. 432 pp.
9. Goldfeld A, Ellner J J. Pathogenesis and management of HIV/TB co-infection in Asia. Tuberculosis (Edinb). 2007; 87 Suppl 1:S26-30.
10. Harries A D, Lawn S D, Getahun H, Zachariah R, Havlir D V. HIV and tuberculosis—science and implementation to turn the tide and reduce deaths. J Int AIDS Soc. 2012; 15(2):17396.
11. Akolo C, Adetifa I, Shepperd S, Volmink J. Treatment of latent tuberculosis infection in HIV infected persons. The Cochrane database of systematic reviews. 2010(1): CD000171.
12. Houben R M, Sumner T, Grant A D, White R G. Ability of preventive therapy to cure latent *Mycobacterium tuberculosis* infection in HIV-infected individuals in high-burden settings. Proc Natl Acad Sci USA. 2014; 111(14): 5325-30.
13. Churchyard G J, Fielding K L, Lewis J J, Coetzee L, Corbett E L, Godfrey-Faussett P, Hayes R J, Chaisson R E, Grant A D, Thibela T B S T. A trial of mass isoniazid preventive therapy for tuberculosis control. N Engl J Med. 2014; 370(4):301-10.
14. Gray J M, Cohn D L. Tuberculosis and HIV coinfection. Semin Respir Crit Care Med. 2013; 34(1):32-43. Epub 2013/03/06. doi: 10.1055/s-0032-1333469. PubMed PMID: 23460004.
15. Jia R, Pan Q, Ding S, Rong L, Liu S L, Geng Y, Qiao W, Liang C. The N-terminal region of IFITM3 modulates its antiviral activity by regulating IFITM3 cellular localization. J Virol. 2012; 86(24):13697-707.
16. Chutiwitoonchai N, Hiyoshi M, Hiyoshi-Yoshidomi Y, Hashimoto M, Tokunaga K, Suzu S. Characteristics of IFITM, the newly identified IFN-inducible anti-HIV-1 family proteins. Microbes Infect. 2013; 15(4):280-90.
17. Lu J, Pan Q, Rong L, He W, Liu S L, Liang C. The IFITM proteins inhibit HIV-1 infection. J Virol. 2011; 85(5):2126-37.
18. de Carvalho L P, Lin G, Jiang X, Nathan C. Nitazoxanide kills replicating and nonreplicating *Mycobacterium tuberculosis* and evades resistance. Journal of medicinal chemistry. 2009; 52(19):5789-92.
19. Shigyo K, Ocheretina O, Merveille Y M, Johnson W D, Pape J W, Nathan C F, Fitzgerald D W. Efficacy of nitazoxanide against clinical isolates of *Mycobacterium tuberculosis*. Antimicrob Agents Chemother. 2013; 57(6): 2834-7.
20. Haffizulla J, Hartman A, Hoppers M, Resnick H, Samudrala S, Ginocchio C, Bardin M, Rossignol J F, Group USNICS. Effect of nitazoxanide in adults and adolescents with acute uncomplicated influenza: a double-blind, randomised, placebo-controlled, phase 2b/3 trial. Lancet Infect Dis. 2014; 14(7):609-18.
21. Rossignol J F, Kabil S M, El-Gohary Y, Elfert A, Keeffe E B. Clinical trial: randomized, double-blind, placebo-controlled study of nitazoxanide monotherapy for the treatment of patients with chronic hepatitis C genotype 4. Alimentary pharmacology & therapeutics. 2008; 28(5): 574-80.
22. Rossignol J F, Elfert A, El-Gohary Y, Keeffe E B. Improved virologic response in chronic hepatitis C genotype 4 treated with nitazoxanide, peginterferon, and ribavirin. Gastroenterology. 2009; 136(3):856-62.
23. Rossignol J F, Hidalgo H, Feregrino M, Higuera F, Gomez W H, Romero J L, Padierna J, Geyne A, Ayers M S. A double-'blind' placebo-controlled study of nitazoxanide in the treatment of cryptosporidial diarrhoea in AIDS patients in Mexico. Transactions of the Royal Society of Tropical Medicine and Hygiene. 1998; 92(6): 663-6.
24. Pawlowski A, Jansson M, Skold M, Rottenberg M E, Kallenius G. Tuberculosis and HIV co-infection. PLoS Pathog. 2012; 8(2):e1002464.
25. Shen R, Richter H E, Smith P D. Early HIV-1 target cells in human vaginal and ectocervical mucosa. Am J Reprod Immunol. 2011; 65(3):261-7.
26. Shen R, Richter H E, Clements R H, Novak L, Huff K, Bimczok D, Sankaran-Walters S, Dandekar S, Clapham P R, Smythies L E, Smith P D. Macrophages in vaginal but not intestinal mucosa are monocyte-like and permissive to human immunodeficiency virus type 1 infection. J Virol. 2009; 83(7):3258-67.
27. Guirado E, Schlesinger L S, Kaplan G. Macrophages in tuberculosis: friend or foe. Semin Immunopathol. 2013; 35(5):563-83. Epub 2013/07/19.
28. Ehlers S. Lazy, dynamic or minimally recrudescent? On the elusive nature and location of the *mycobacterium* responsible for latent tuberculosis. Infection. 2009; 37(2):87-95.
29. Coleman C M, Wu L. HIV interactions with monocytes and dendritic cells: viral latency and reservoirs. Retrovirology. 2009; 6:51.
30. Redel L, Le Douce V, Cherrier T, Marban C, Janossy A, Aunis D, Van Lint C, Rohr O, Schwartz C. HIV-1 regulation of latency in the monocyte-macrophage lineage and in CD4+ T lymphocytes. J Leukoc Biol. 2010; 87(4):575-88.
31. Cobos-Jimenez V, Booiman T, Hamann J, Kootstra N A. Macrophages and HIV-1. Curr Opin HIV AIDS. 2011; 6(5):385-90.
32. Costiniuk C T, Jenabian M A. The lungs as anatomical reservoirs of HIV infection. Rev Med Virol. 2013.
33. Honda Y, Rogers L, Nakata K, Zhao B Y, Pine R, Nakai Y, Kurosu K, Rom W N, Weiden M. Type I interferon induces inhibitory 16-kD CCAAT/enhancer binding protein (C/EBP)beta, repressing the HIV-1 long terminal repeat in macrophages: pulmonary tuberculosis alters C/EBP expression, enhancing HIV-1 replication. J Exp Med. 1998; 188(7):1255-65.
34. Orenstein J M, Fox C, Wahl S M. Macrophages as a source of HIV during opportunistic infections. Science. 1997; 276(5320):1857-61.
35. Nakata K, Rom W N, Honda Y, Condos R, Kanegasaki S, Cao Y, Weiden M. *Mycobacterium tuberculosis* enhances human immunodeficiency virus-1 replication in the lung. Am J Respir Crit Care Med. 1997; 155(3):996-1003.
36. Weiden M, Tanaka N, Qiao Y, Zhao B Y, Honda Y, Nakata K, Canova A, Levy D E, Rom W N, Pine R. Differentiation of monocytes to macrophages switches the *Mycobacterium tuberculosis* effect on HIV-1 replication from stimulation to inhibition: modulation of interferon response and CCAAT/enhancer binding protein beta expression. J Immunol. 2000; 165(4):2028-39.
37. Hoshino Y, Nakata K, Hoshino S, Honda Y, Tse D B, Shioda T, Rom W N, Weiden M. Maximal HIV-1 replication in alveolar macrophages during tuberculosis requires both lymphocyte contact and cytokines. J Exp Med. 2002; 195(4):495-505.
38. Ranjbar S, Ly N, Thim S, Reynes J M, Goldfeld A E. *Mycobacterium tuberculosis* recall antigens suppress HIV-1 replication in anergic donor cells via CD8+ T cell expansion and increased IL-10 levels. J Immunol. 2004; 172(3):1953-9.
39. Boussiotis V A, Tsai E Y, Yunis E J, Thim S, Delgado J C, Dascher C C, Berezovskaya A, Rousset D, Reynes J M, Goldfeld A E. IL-10-producing T cells suppress immune responses in anergic tuberculosis patients. J Clin Invest. 2000; 105(9):1317-25.
40. Siegrist F, Ebeling M, Certa U. The small interferon-induced transmembrane genes and proteins. J Interferon Cytokine Res. 2011; 31(1):183-97.
41. Moffatt P, Gaumond M H, Salois P, Sellin K, Bessette M C, Godin E, de Oliveira P T, Atkins G J, Nanci A, Thomas G. Bril: a novel bone-specific modulator of mineralization. J Bone Miner Res. 2008; 23(9):1497-508.
42. Reid L E, Brasnett A H, Gilbert C S, Porter A C, Gewert D R, Stark G R, Kerr I M. A single DNA response element can confer inducibility by both alpha- and gamma-interferons. Proc Natl Acad Sci USA. 1989; 86(3):840-4.
43. Lewin A R, Reid L E, McMahon M, Stark G R, Kerr I M. Molecular analysis of a human interferon-inducible gene family. Eur J Biochem. 1991; 199(2):417-23.
44. McKendry R, John J, Flavell D, Muller M, Kerr I M, Stark G R. High-frequency mutagenesis of human cells and characterization of a mutant unresponsive to both alpha and gamma interferons. Proc Natl Acad Sci USA. 1991; 88(24):11455-9.
45. Friedman R L, Manly S P, McMahon M, Kerr I M, Stark G R. Transcriptional and posttranscriptional regulation of interferon-induced gene expression in human cells. Cell. 1984; 38(3):745-55.
46. Kelly J M, Gilbert C S, Stark G R, Kerr I M. Differential regulation of interferon-induced mRNAs and c-myc mRNA by alpha- and gamma-interferons. Eur J Biochem. 1985; 153(2):367-71.
47. Brass A L, Huang I C, Benita Y, John S P, Krishnan M N, Feeley E M, Ryan B J, Weyer J L, van der Weyden L, Fikrig E, Adams D J, Xavier R J, Farzan M, Elledge S J. The IFITM proteins mediate cellular resistance to influenza A H1N1 virus, West Nile virus, and dengue virus. Cell. 2009; 139(7):1243-54.
48. Bailey C C, Huang I C, Kam C, Farzan M. Ifitm3 limits the severity of acute influenza in mice. PLoS Pathog. 2012; 8(9):e1002909.
49. Everitt A R, Clare S, Pertel T, John S P, Wash R S, Smith S E, Chin C R, Feeley E M, Sims J S, Adams D J, Wise H M, Kane L, Goulding D, Digard P, Anttila V, Baillie J K, Walsh T S, Hume D A, Palotie A, Xue Y, Colonna V, Tyler-Smith C, Dunning J, Gordon S B, Smyth R L, Openshaw P J, Dougan G, Brass A L, Kellam P. IFITM3 restricts the morbidity and mortality associated with influenza. Nature. 2012; 484(7395):519-23.
50. Le Blanc I, Luyet P P, Pons V, Ferguson C, Emans N, Petiot A, Mayran N, Demaurex N, Faure J, Sadoul R, Parton R G, Gruenberg J. Endosome-to-cytosol transport of viral nucleocapsids. Nat Cell Biol. 2005; 7(7):653-64.
51. Zaitseva E, Yang S T, Melikov K, Pourmal S, Chernomordik L V. Dengue virus ensures its fusion in late endosomes using compartment-specific lipids. PLoS Pathog. 2010; 6(10):e1001131.
52. van der Schaar H M, Rust M J, Chen C, van der Ende-Metselaar H, Wilschut J, Zhuang X, Smit J M. Dissecting the cell entry pathway of dengue virus by single-particle tracking in living cells. PLoS Pathog. 2008; 4(12):e1000244.
53. Thompson B S, Moesker B, Smit J M, Wilschut J, Diamond M S, Fremont D H. A therapeutic antibody against west nile virus neutralizes infection by blocking fusion within endosomes. PLoS Pathog. 2009; 5(5):e1000453.
54. Yoshimura A, Ohnishi S. Uncoating of influenza virus in endosomes. J Virol. 1984; 51(2):497-504.
55. Sieczkarski S B, Whittaker G R. Differential requirements of Rab5 and Rab7 for endocytosis of influenza and other enveloped viruses. Traffic. 2003; 4(5):333-43.
56. Feeley E M, Sims J S, John S P, Chin C R, Pertel T, Chen L M, Gaiha G D, Ryan B J, Donis R O, Elledge S J, Brass A L. IFITM3 inhibits influenza A virus infection by preventing cytosolic entry. PLoS Pathog. 2011; 7(10):e1002337.
57. Rojek J M, Kunz S. Cell entry by human pathogenic arenaviruses. Cell Microbiol. 2008; 10(4):828-35.

58. Rojek J M, Sanchez A B, Nguyen N T, de la Torre J C, Kunz S. Different mechanisms of cell entry by human-pathogenic Old World and New World arenaviruses. J Virol. 2008; 82(15):7677-87.
59. Amini-Bavil-Olyaee S, Choi Y J, Lee J H, Shi M, Huang I C, Farzan M, Jung J U. The antiviral effector IFITM3 disrupts intracellular cholesterol homeostasis to block viral entry. Cell Host Microbe. 2013; 13(4):452-64.
60. Perry R J, Ridgway N D. Oxysterol-binding protein and vesicle-associated membrane protein-associated protein are required for sterol-dependent activation of the ceramide transport protein. Mol Biol Cell. 2006; 17(6):2604-16.
61. Goto A, Liu X, Robinson C A, Ridgway N D. Multisite phosphorylation of oxysterol-binding protein regulates sterol binding and activation of sphingomyelin synthesis. Mol Biol Cell. 2012; 23(18):3624-35.
62. Peretti D, Dahan N, Shimoni E, Hirschberg K, Lev S. Coordinated lipid transfer between the endoplasmic reticulum and the Golgi complex requires the VAP proteins and is essential for Golgi-mediated transport. Mol Biol Cell. 2008; 19(9):3871-84.
63. Shen C, Wu X R, Jiao W W, Sun L, Feng W X, Xiao J, Miao Q, Liu F, Yin Q Q, Zhang C G, Guo Y J, Shen A D. A Functional Promoter Polymorphism of IFITM3 Is Associated with Susceptibility to Pediatric Tuberculosis in Han Chinese Population. PLoS One. 2013; 8(7): e67816.
64. Everitt A R, Clare S, McDonald J U, Kane L, Harcourt K, Ahras M, Lall A, Hale C, Rodgers A, Young D B, Haque A, Billker O, Tregoning J S, Dougan G, Kellam P. Defining the range of pathogens susceptible to ifitm3 restriction using a knockout mouse model. PLoS One. 2013; 8(11):e80723.
65. Seok J, et al., Genomic responses in mouse models poorly mimic human inflammatory diseases. Proc Natl Acad Sci USA. 2013; 110(9):3507-12.
66. Wee Y S, Roundy K M, Weis J J, Weis J H. Interferon-inducible transmembrane proteins of the innate immune response act as membrane organizers by influencing clathrin and v-ATPase localization and function. Innate immunity. 2012; 18(6):834-45.
67. Wong D, Bach H, Sun J, Hmama Z, Av-Gay Y. *Mycobacterium tuberculosis* protein tyrosine phosphatase (PtpA) excludes host vacuolar-H+-ATPase to inhibit phagosome acidification. Proc Natl Acad Sci USA. 2011; 108(48):19371-6.
68. Gengenbacher M, Kaufmann S H. *Mycobacterium tuberculosis*: success through dormancy. FEMS microbiology reviews. 2012; 36(3):514-32.
69. Sille F C, Martin C, Jayaraman P, Rothchild A, Fortune S, Besra G S, Behar S M, Boes M. Requirement for invariant chain in macrophages for *Mycobacterium tuberculosis* replication and CD1d antigen presentation. Infect Immun. 2011; 79(8):3053-63.
70. Bosque A, Planelles V. Induction of HIV-1 latency and reactivation in primary memory CD4+ T cells. Blood. 2009; 113(1):58-65.
71. Esensten J H, Tsytsykova A V, Lopez-Rodriguez C, Ligeiro F A, Rao A, Goldfeld A E. NFAT5 binds to the TNF promoter distinctly from NFATp, c, 3 and 4, and activates TNF transcription during hypertonic stress alone. Nucleic Acids Res. 2005; 33(12):3845-54.
72. Hemelaar J. The origin and diversity of the HIV-1 pandemic. Trends Mol Med. 2012; 18(3):182-92.
73. Anandaiah A, Sinha S, Bole M, Sharma S K, Kumar N, Luthra K, Li X, Zhou X, Nelson B, Han X, Tachado S D, Patel N R, Koziel H. Vitamin D rescues impaired *Mycobacterium tuberculosis*-mediated tumor necrosis factor release in macrophages of HIV-seropositive individuals through an enhanced Toll-like receptor signaling pathway in vitro. Infect Immun. 2013; 81(1):2-10.
74. Koziel H, Eichbaum Q, Kruskal B A, Pinkston P, Rogers R A, Armstrong M Y, Richards F F, Rose R M, Ezekowitz R A. Reduced binding and phagocytosis of *Pneumocystis carinii* by alveolar macrophages from persons infected with HIV-1 correlates with mannose receptor downregulation. J Clin Invest. 1998; 102(7):1332-44.
75. Han X, Li X, Yue S C, Anandaiah A, Hashem F, Reinach P S, Koziel H, Tachado S D. Epigenetic regulation of tumor necrosis factor a (TNFa) release in human macrophages by HIV-1 single-stranded RNA (ssRNA) is dependent on TLR8 signaling. J Biol Chem. 2012; 287(17): 13778-86.
76. Ranjbar S, Boshoff H I, Mulder A, Siddiqi N, Rubin E J, Goldfeld A E. HIV-1 replication is differentially regulated by distinct clinical strains of *Mycobacterium tuberculosis*. PLoS One. 2009; 4(7):e6116.
77. Ranjbar S, Jasenosky L D, Chow N, Goldfeld A E. Regulation of *Mycobacterium tuberculosis*-Dependent HIV-1 Transcription Reveals a New Role for NFAT5 in the Toll-Like Receptor Pathway. PLoS Pathog. 2012; 8(4):e1002620.
78. Falvo J V, Ranjbar S, Jasenosky L D, Goldfeld A E. Arc of a Vicious Circle: Pathways Activated by *Mycobacterium tuberculosis* That Target the HIV-1 Long Terminal Repeat. Am J Respir Cell Mol Biol. 2011; 45(6):1116-24.
79. Toshchakov V, Jones B W, Perera P Y, Thomas K, Cody M J, Zhang S, Williams B R, Major J, Hamilton T A, Fenton M J, Vogel S N. TLR4, but not TLR2, mediates IFN-beta-induced STAT1alpha/beta-dependent gene expression in macrophages. Nat Immunol. 2002; 3(4): 392-8.
80. Shi S, Blumenthal A, Hickey C M, Gandotra S, Levy D, Ehrt S. Expression of many immunologically important genes in *Mycobacterium tuberculosis*-infected macrophages is independent of both TLR2 and TLR4 but dependent on IFN-alphabeta receptor and STAT1. J Immunol. 2005; 175(5):3318-28.
81. Yao L, Dong H, Zhu H, Nelson D, Liu C, Lambiase L, Li X. Identification of the IFITM3 gene as an inhibitor of hepatitis C viral translation in a stable STAT1 cell line. J Viral Hepat. 2011; 18(10):e523-9.
82. Berry M P, Graham C M, McNab F W, Xu Z, Bloch S A, Oni T, Wilkinson K A, Banchereau R, Skinner J, Wilkinson R J, Quinn C, Blankenship D, Dhawan R, Cush J J, Mejias A, Ramilo O, Kon O M, Pascual V, Banchereau J, Chaussabel D, O'Garra A. An interferon-inducible neutrophil-driven blood transcriptional signature in human tuberculosis. Nature. 2010; 466(7309):973-7.
83. Mayer-Barber K D, Andrade B B, Oland S D, Amaral E P, Barber D L, Gonzales J, Derrick S C, Shi R, Kumar N P, Wei W, Yuan X, Zhang G, Cai Y, Babu S, Catalfamo M, Salazar A M, Via L E, Barry C E, 3rd, Sher A. Host-directed therapy of tuberculosis based on interleukin-1 and type I interferon crosstalk. Nature. 2014; 511(7507): 99-103.
84. Novikov A, Cardone M, Thompson R, Shenderov K, Kirschman K D, Mayer-Barber K D, Myers T G, Rabin R L, Trinchieri G, Sher A, Feng C G. *Mycobacterium tuberculosis* triggers host type I IFN signaling to regulate IL-1beta production in human macrophages. J Immunol. 2011; 187(5):2540-7.

85. Dorhoi A, Yeremeev V, Nouailles G, Weiner J, 3rd, Jorg S, Heinemann E, Oberbeck-Muller D, Knaul J K, Vogelzang A, Reece S T, Hahnke K, Mollenkopf H J, Brinkmann V, Kaufmann S H. Type I IFN signaling triggers immunopathology in tuberculosis-susceptible mice by modulating lung phagocyte dynamics. Eur J Immunol. 2014.

86. Teles R M, Graeber T G, Krutzik S R, Montoya D, Schenk M, Lee D J, Komisopoulou E, Kelly-Scumpia K, Chun R, Iyer S S, Sarno E N, Rea T H, Hewison M, Adams J S, Popper S J, Relman D A, Stenger S, Bloom B R, Cheng G, Modlin R L. Type I interferon suppresses type I I interferon-triggered human anti-mycobacterial responses. Science. 2013; 339(6126):1448-53.

87. de Paus R A, van Wengen A, Schmidt I, Visser M, Verdegaal E M, van Dissel J T, van de Vosse E. Inhibition of the type I immune responses of human monocytes by IFN-alpha and IFN-beta. Cytokine. 2013; 61(2):645-55.

88. Piehler A P, Grimholt R M, Ovstebo R, Berg J P. Gene expression results in lipopolysaccharide-stimulated monocytes depend significantly on the choice of reference genes. BMC Immunol. 2010; 11:21. Epub 2010/05/06.

89. Manca C, Tsenova L, Bergtold A, Freeman S, Tovey M, Musser J M, Barry C E, 3rd, Freedman V H, Kaplan G. Virulence of a *Mycobacterium tuberculosis* clinical isolate in mice is determined by failure to induce Thl type immunity and is associated with induction of IFN-alpha/beta. Proc Natl Acad Sci USA. 2001; 98(10):5752-7.

90. Manca C, Tsenova L, Freeman S, Barczak A K, Tovey M, Murray P J, Barry C, Kaplan G. Hypervirulent *M. tuberculosis* W/Beijing strains upregulate type I IFNs and increase expression of negative regulators of the Jak-Stat pathway. J Interferon Cytokine Res. 2005; 25(11):694-701.

91. Falvo J V, Ranjbar S, Jasenosky L D, Goldfeld A E. Arc of a vicious circle: pathways activated by *Mycobacterium tuberculosis* that target the HIV-1 LTR. Am J Respir Cell Mol Biol. 2011.

92. Weidner J M, Jiang D, Pan X B, Chang J, Block T M, Guo J T. Interferon-induced cell membrane proteins, IFITM3 and tetherin, inhibit vesicular stomatitis virus infection via distinct mechanisms. J Virol. 2010; 84(24): 12646-57.

93. Huang I C, Bailey C C, Weyer J L, Radoshitzky S R, Becker M M, Chiang J J, Brass A L, Ahmed A A, Chi X, Dong L, Longobardi L E, Boltz D, Kuhn J H, Elledge S J, Bavari S, Denison M R, Choe H, Farzan M. Distinct patterns of IFITM-mediated restriction of filoviruses, SARS coronavirus, and influenza A virus. PLoS Pathog. 2011; 7(1):e1001258.

94. Fratti R A, Chua J, Vergne I, Deretic V. *Mycobacterium tuberculosis* glycosylated phosphatidylinositol causes phagosome maturation arrest. Proc Natl Acad Sci USA. 2003; 100(9):5437-42.

95. Kang P B, Azad A K, Torrelles J B, Kaufman T M, Beharka A, Tibesar E, DesJardin L E, Schlesinger L S. The human macrophage mannose receptor directs *Mycobacterium tuberculosis* lipoarabinomannan-mediated phagosome biogenesis. J Exp Med. 2005; 202(7):987-99.

96. Sonnino S, Prinetti A. Membrane domains and the "lipid raft" concept. Curr Med Chem. 2013; 20(1):4-21.

97. Hmama Z, Sendide K, Talal A, Garcia R, Dobos K, Reiner N E. Quantitative analysis of phagolysosome fusion in intact cells: inhibition by mycobacterial lipoarabinomannan and rescue by an 1alpha,25-dihydroxyvitamin D3-phosphoinositide 3-kinase pathway. J Cell Sci. 2004; 117(Pt 10):2131-40.

98. Welin A, Winberg M E, Abdalla H, Sarndahl E, Rasmusson B, Stendahl O, Lerm M. Incorporation of *Mycobacterium tuberculosis* lipoarabinomannan into macrophage membrane rafts is a prerequisite for the phagosomal maturation block. Infect Immun. 2008; 76(7):2882-7.

99. Fine-Coulson K, Reaves B J, Karls R K, Quinn F D. The role of lipid raft aggregation in the infection of type II pneumocytes by *Mycobacterium tuberculosis*. PLoS One. 2012; 7(9):e45028.

100. Danelishvili L, McGarvey J, Li Y J, Bermudez L E. *Mycobacterium tuberculosis* infection causes different levels of apoptosis and necrosis in human macrophages and alveolar epithelial cells. Cell Microbiol. 2003; 5(9): 649-60.

101. Bermudez L E, Goodman J. *Mycobacterium tuberculosis* invades and replicates within type II alveolar cells. Infect Immun. 1996; 64(4):1400-6.

102. Chua P K, McCown M F, Rajyaguru S, Kular S, Varma R, Symons J, Chiu S S, Cammack N, Naj era I. Modulation of alpha interferon anti-hepatitis C virus activity by ISG15. J Gen Virol. 2009; 90(Pt 12):2929-39.

103. Ashiru O T, Pillay M, Sturm A W. Adhesion to and invasion of pulmonary epithelial cells by the F15/LAM4/KZN and Beijing strains of *Mycobacterium tuberculosis*. J Med Microbiol. 2010; 59(Pt 5):528-33.

104. Guo X G, Ji T X, Xia Y, Ma Y Y. Autophagy protects type II alveolar epithelial cells from *Mycobacterium tuberculosis* infection. Biochem Biophys Res Commun. 2013; 432(2):308-13.

105. Fairn G D, Grinstein S. How nascent phagosomes mature to become phagolysosomes. Trends Immunol. 2012; 33(8):397-405.

106. Eskelinen E L, Tanaka Y, Saftig P. At the acidic edge: emerging functions for lysosomal membrane proteins. Trends Cell Biol. 2003; 13(3):137-45.

107. Pols M S, Klumperman J. Trafficking and function of the tetraspanin CD63. Exp Cell Res. 2009; 315(9):1584-92.

108. Macdonald J L, Pike L J. A simplified method for the preparation of detergent-free lipid rafts. J Lipid Res. 2005; 46(5):1061-7.

109. Keren I, Minami S, Rubin E, Lewis K. Characterization and transcriptome analysis of *Mycobacterium tuberculosis* persisters. mBio. 2011; 2(3):e00100-11.

110. Hussar D A. New drugs of 2003. J Am Pharm Assoc (2003). 2004; 44(2):168-206; quiz 7-10.

111. Doumbo O, Rossignol J F, Pichard E, Traore H A, Dembele T M, Diakite M, Traore F, Diallo D A. Nitazoxanide in the treatment of cryptosporidial diarrhea and other intestinal parasitic infections associated with acquired immunodeficiency syndrome in tropical Africa. Am J Trop Med Hyg. 1997; 56(6):637-9.

112. Via L E, Lin P L, Ray S M, Carrillo J, Allen S S, Eum S Y, Taylor K, Klein E, Manjunatha U, Gonzales J, Lee E G, Park S K, Raleigh J A, Cho S N, McMurray D N, Flynn J L, Barry C E, 3rd. Tuberculous granulomas are hypoxic in guinea pigs, rabbits, and nonhuman primates. Infect Immun. 2008; 76(6):2333-40.

113. Parekh M J, Schluger N W. Treatment of latent tuberculosis infection. Ther Adv Respir Dis. 2013; 7(6):351-6.

114. de Carvalho L P, Lin G, Jiang X, Nathan C. Nitazoxanide kills replicating and nonreplicating *Mycobacterium tuberculosis* and evades resistance. Journal of medicinal chemistry. 2009; 52(19):5789-92.

115. Lam K K Y, Zheng X, Forestieri R, Balgi A D, Nodwell M, Vollett S, Anderson H J, Andersen R J, Av-Gay Y, Roberge M. Nitazoxanide stimulates autophagy and inhibits mTORC1 signaling and intracellular proliferation of *Mycobacterium tuberculosis*. PLoS Pathog. 2012; 8(5): e1002691.

116. Elazar M, Liu M, McKenna S A, Liu P, Gehrig E A, Puglisi J D, Rossignol J F, Glenn J S. The anti-hepatitis C agent nitazoxanide induces phosphorylation of eukaryotic initiation factor 2alpha via protein kinase activated by double-stranded RNA activation. Gastroenterology. 2009; 137(5):1827-35.

117. Pindel A, Sadler A. The role of protein kinase R in the interferon response. Journal of interferon & cytokine research: the official journal of the International Society for Interferon and Cytokine Research. 2011; 31(1):59-70.

118. Kang R, Tang D. PKR-dependent inflammatory signals. Sci Signal. 2012; 5(247):pe47.

119. Munir M, Berg M. The multiple faces of proteinkinase R in antiviral defense. Virulence. 2013; 4(1):85-9.

120. Talloczy Z, Jiang W, Virgin H Wt, Leib D A, Scheuner D, Kaufman R J, Eskelinen E L, Levine B. Regulation of starvation- and virus-induced autophagy by the eIF2α kinase signaling pathway. Proc Natl Acad Sci USA. 2002; 99(1):190-5.

121. Goldstone D C, Ennis-Adeniran V, Hedden J J, Groom H C, Rice G I, Christodoulou E, Walker P A, Kelly G, Haire L F, Yap M W, de Carvalho L P, Stoye J P, Crow Y J, Taylor I A, Webb M. HIV-1 restriction factor SAMHD1 is a deoxynucleoside triphosphate triphosphohydrolase. Nature. 2011; 480(7377):379-82.

122. Laguette N, Sobhian B, Casartelli N, Ringeard M, Chable-Bessia C, Segeral E, Yatim A, Emiliani S, Schwartz O, Benkirane M. SAMHD1 is the dendritic- and myeloid-cell-specific HIV-1 restriction factor counteracted by Vpx. Nature. 2011; 474(7353):654-7.

123. Hrecka K, Hao C, Gierszewska M, Swanson S K, Kesik-Brodacka M, Srivastava S, Florens L, Washburn M P, Skowronski J. Vpx relieves inhibition of HIV-1 infection of macrophages mediated by the SAMHD1 protein. Nature. 2011; 474(7353):658-61.

124. St Gelais C, de Silva S, Amie S M, Coleman C M, Hoy H, Hollenbaugh J A, Kim B, Wu L. SAMHD1 restricts HIV-1 infection in dendritic cells (DCs) by dNTP depletion, but its expression in DCs and primary CD4+T-lymphocytes cannot be upregulated by interferons. Retrovirology. 2012; 9:105.

125. Lahouassa H, Daddacha W, Hofmann H, Ayinde D, Logue E C, Dragin L, Bloch N, Maudet C, Bertrand M, Gramberg T, Pancino G, Priet S, Canard B, Laguette N, Benkirane M, Transy C, Landau N R, Kim B, Margottin-Goguet F. SAMHD1 restricts the replication of human immunodeficiency virus type 1 by depleting the intracellular pool of deoxynucleoside triphosphates. Nat Immunol. 2012; 13(3):223-8.

126. Baldauf H M, Pan X, Erikson E, Schmidt S, Daddacha W, Burggraf M, Schenkova K, Ambiel I, Wabnitz G, Gramberg T, Panitz S, Flory E, Landau N R, Sertel S, Rutsch F, Lasitschka F, Kim B, Konig R, Fackler O T, Keppler O T. SAMHD1 restricts HIV-1 infection in resting CD4(+) T cells. Nat Med. 2012; 18(11):1682-7.

127. Kim B, Nguyen L A, Daddacha W, Hollenbaugh J A. Tight interplay among SAMHD1 protein level, cellular dNTP levels, and HIV-1 proviral DNA synthesis kinetics in human primary monocyte-derived macrophages. J Biol Chem. 2012; 287(26):21570-4.

128. Descours B, Cribier A, Chable-Bessia C, Ayinde D, Rice G, Crow Y, Yatim A, Schwartz O, Laguette N, Benkirane M. SAIVIHD 1 restricts HIV-1 reverse transcription in quiescent CD4(+) T-cells. Retrovirology. 2012; 9:87.

129. Cribier A, Descours B, Valadao A L, Laguette N, Benkirane M. Phosphorylation of SAIV1HD1 by cyclin A2/CDK1 regulates its restriction activity toward HIV-1. Cell Rep. 2013; 3(4):1036-43.

130. White T E, Brandariz-Nunez A, Valle-Casuso J C, Arnie S, Nguyen L A, Kim B, Tuzova M, Diaz-Griffero F. The retroviral restriction ability of SAIV1HD1, but not its deoxynucleotide triphosphohydrolase activity, is regulated by phosphorylation. Cell Host Microbe. 2013; 13(4):441-51.

131. Tan X, Hu L, Luquette L J, 3rd, Gao G, Liu Y, Qu H, Xi R, Lu Z J, Park P J, Elledge S J. Systematic identification of synergistic drug pairs targeting HIV. Nature Biotechnol. 2012; 30(11):1125-30.

132. Sadler A J, Latchoumanin O, Hawkes D, Mak J, Williams B R. An antiviral response directed by PKR phosphorylation of the RNA helicase A. PLoS Pathog. 2009; 5(2):e1000311.

133. Fujii R, Okamoto M, Aratani S, Oishi T, Ohshima T, Taira K, Baba M, Fukamizu A, Nakajima T. A Role of RNA Helicase A in cis-Acting Transactivation Response Element-mediated Transcriptional Regulation of Human Immunodeficiency Virus Type 1. J Biol Chem. 2001; 276(8):5445-51.

134. Xing L, Niu M, Kleiman L. In vitro and in vivo analysis of the interaction between RNA helicase A and HIV-1 RNA. J Virol. 2012; 86(24):13272-80.

135. Kumar A, Haque J, Lacoste J, Hiscott J, Williams B R. Double-stranded RNA-dependent protein kinase activates transcription factor N F-kappa B by phosphorylating I kappa B. Proc Natl Acad Sci USA. 1994; 91(14):6288-92.

136. Elazar M, Liu M, McKenna S A, Liu P, Gehrig E A, Puglisi J D, Rossignol J-F, Glenn J S. The anti-hepatitis C agent nitazoxanide induces phosphorylation of eukaryotic initiation factor 2a via protein kinase activated by double-stranded RNA activation. Gastroenterology. 2009; 137(5): 1827-35.

137. Isken O, Grassmann C W, Sarisky R T, Kann M, Zhang S, Grosse F, Kao P N, Behrens S E. Members of the NF90/NFAR protein group are involved in the life cycle of a positive-strand RNA virus. EMBO J. 2003; 22(21): 5655-65.

138. Isken O, Baroth M, Grassmann C W, Weinlich S, Ostareck D H, Ostareck-Lederer A, Behrens S E. Nuclear factors are involved in hepatitis C virus RNA replication. RNA. 2007; 13(10):1675-92.

139. Bolinger C, Yilmaz A, Hartman T R, Kovacic M B, Fernandez S, Ye J, Forget M, Green P L, Boris-Lawrie K. RNA helicase A interacts with divergent lymphotropic retroviruses and promotes translation of human T-cell leukemia virus type 1. Nucleic Acids Res. 2007; 35(8): 2629-42.

140. Lawrence P, Rieder E. Identification of RNA helicase A as a new host factor in the replication cycle of foot-and-mouth disease virus. J Virol. 2009; 83(21):11356-66.

141. Tsytsykova A V, Raj sbaum R, Falvo J V, Ligeiro F, Neely S R, Goldfeld A E. Activation-dependent intrachromosomal interactions formed by the TNF gene promoter and two distal enhancers. Proc Natl Acad Sci USA. 2007; 104(43):16850-5.

142. Biglione S, Tsytsykova A V, Goldfeld A E. Monocyte-specific accessibility of a matrix attachment region in the tumor necrosis factor locus. J Biol Chem. 2011; 286(51): 44126-33.

143. Rohde K, Yates R M, Purdy G E, Russell D G. *Mycobacterium tuberculosis* and the environment within the phagosome. Immunol Rev. 2007; 219:37-54.
144. Bradfute S B, Castillo E F, Arko-Mensah J, Chauhan S, Jiang S, Mandell M, Deretic V. Autophagy as an immune effector against tuberculosis. Curr Opin Microbiol. 2013; 16(3):355-65.
145. Campbell G R, Spector S A. Vitamin D inhibits human immunodeficiency virus type 1 and *Mycobacterium tuberculosis* infection in macrophages through the induction of autophagy. PLoS Pathog. 2012; 8(5):e1002689.
146. Campbell G R, Spector S A. Hormonally active vitamin D3 (1alpha,25-dihydroxycholecalciferol) triggers autophagy in human macrophages that inhibits HIV-1 infection. J Biol Chem. 2011; 286(21):18890-902.
147. Espert L, Varbanov M, Robert-Hebmann V, Sagnier S, Robbins I, Sanchez F, Lafont V, Biard-Piechaczyk M. Differential role of autophagy in CD4 T cells and macrophages during X4 and R5 HIV-1 infection. PLoS One. 2009; 4(6):e5787.
148. Kyei G B, Dinkins C, Davis A S, Roberts E, Singh S B, Dong C, Wu L, Kominami E, Ueno T, Yamamoto A, Federico M, Panganiban A, Vergne I, Deretic V. Autophagy pathway intersects with HIV-1 biosynthesis and regulates viral yields in macrophages. J Cell Biol. 2009; 186(2):255-68.
149. Nakatogawa H, Ichimura Y, Ohsumi Y. Atg8, a ubiquitin-like protein required for autophagosome formation, mediates membrane tethering and hemifusion. Cell. 2007; 130(1):165-78.
150. Talloczy Z, Virgin H Wt, Levine B. PKR-dependent autophagic degradation of herpes simplex virus type 1. Autophagy. 2006; 2(1):24-9.
151. Ogolla P S, Portillo J A, White C L, Patel K, Lamb B, Sen G C, Subauste C S. The Protein Kinase Double-Stranded RNA-Dependent (PKR) Enhances Protection against Disease Cause by a Non-Viral Pathogen. PLoS Pathog. 2013; 9(8):e1003557.
152. Shen S, Niso-Santano M, Adjemian S, Takehara T, Malik S A, Minoux H, Souquere S, Marino G, Lachkar S, Senovilla L, Galluzzi L, Kepp O, Pierron G, Maiuri M C, Hikita H, Kroemer R, Kroemer G. Cytoplasmic STAT3 represses autophagy by inhibiting PKR activity. Mol Cell. 2012; 48(5):667-80.
153. Van Grol J, Subauste C, Andrade R M, Fujinaga K, Nelson J, Subauste C S. HIV-1 inhibits autophagy in bystander macrophage/monocytic cells through Src-Akt and STAT3. PLoS One. 2010; 5(7):e11733.
154. Kabeya Y, Mizushima N, Ueno T, Yamamoto A, Kirisako T, Noda T, Kominami E, Ohsumi Y, Yoshimori T. LC3, a mammalian homologue of yeast Apg8p, is localized in autophagosome membranes after processing. EMBO J. 2000; 19(21):5720-8.
155. Choi Y J, Park Y J, Park J Y, Jeong H O, Kim D H, Ha Y M, Kim J M, Song Y M, Heo H S, Yu B P, Chun P, Moon H R, Chung H Y. Inhibitory effect of mTOR activator MHY1485 on autophagy: suppression of lysosomal fusion. PLoS One. 2012; 7(8):e43418.
156. O'Leary S, O'Sullivan M P, Keane J. IL-10 blocks phagosome maturation in *Mycobacterium tuberculosis*-infected human macrophages. Am J Respir Cell Mol Biol. 2011; 45(1):172-80.
157. Carow B, Reuschl A K, Gavier-Widen D, Jenkins B J, Ernst M, Yoshimura A, Chambers B J, Rottenberg M E. Critical and independent role for SOCS3 in either myeloid or T cells in resistance to *Mycobacterium tuberculosis*. PLoS Pathog. 2013; 9(7):e1003442.
158. Ashiru O, Howe J D, Butters T D. Nitazoxanide, an antiviral thiazolide, depletes ATP-sensitive intracellular Ca(2+) stores. Virology. 2014; 462-463:135-48. doi: 10.1016/j.virol.2014.05.015. PubMed PMID: 24971706.
159. Elazar M, Liu M, McKenna S A, Liu P, Gehrig E A, Puglisi J D, Rossignol J F, Glenn J S. The anti-hepatitis C agent nitazoxanide induces phosphorylation of eukaryotic initiation factor 2alpha via protein kinase activated by double-stranded RNA activation. Gastroenterology. 2009; 137(5):1827-35. doi: 10.1053/j.gastro.2009.07.056. PubMed PMID: 19664635.
160. Onomoto K, Yoneyama M, Fung G, Kato H, Fujita T. Antiviral innate immunity and stress granule responses. Trends Immunol. 2014; 35(9):420-8. doi: 10.1016/j.it.2014.07.006. PubMed PMID: 25153707.
161. Reineke L C, Kedersha N, Langereis M A, van Kuppeveld F J, Lloyd R E. Stress granules regulate double-stranded RNA-dependent protein kinase activation through a complex containing G3BP1 and Caprin1. MBio. 2015; 6(2):e02486. doi: 10.1128/mBio.02486-14. PubMed PMID: 25784705; PubMed Central PMCID: PMC4453520.
162. Reineke L C, Lloyd R E. The stress granule protein G3BP1 recruits protein kinase R to promote multiple innate immune antiviral responses. J Virol. 2015; 89(5): 2575-89. doi: 10.1128/JVI.02791-14. PubMed PMID: 25520508; PubMed Central PMCID: PMC4325707.
163. Okonski K M, Samuel C E. Stress granule formation induced by measles virus is protein kinase PKR dependent and impaired by RNA adenosine deaminase ADAR1. J Virol. 2013; 87(2):756-66. doi: 10.1128/JVI.02270-12. PubMed PMID: 23115276; PubMed Central PMCID: PMC3554044.
164. Yoo J S, Takahasi K, Ng C S, Ouda R, Onomoto K, Yoneyama M, Lai J C, Lattmann S, Nagamine Y, Matsui T, Iwabuchi K, Kato H, Fujita T. DHX36 enhances RIG-I signaling by facilitating PKR-mediated antiviral stress granule formation. PLoS pathogens. 2014; 10(3): e1004012. doi: 10.1371/journal.ppat.1004012. PubMed PMID: 24651521; PubMed Central PMCID: PMC3961341.
165. Zhang P, Li Y, Xia J, He J, Pu J, Xie J, Wu S, Feng L, Huang X, Zhang P. IPS-1 plays an essential role in dsRNA-induced stress granule formation by interacting with PKR and promoting its activation. J Cell Sci. 2014; 127(Pt 11):2471-82. doi: 10.1242/jcs.139626. PubMed PMID: 24659800.
166. Onomoto K, Jogi M, Yoo J S, Narita R, Morimoto S, Takemura A, Sambhara S, Kawaguchi A, Osari S, Nagata K, Matsumiya T, Namiki H, Yoneyama M, Fujita T. Critical role of an antiviral stress granule containing RIG-I and PKR in viral detection and innate immunity. PLoS one. 2012; 7(8):e43031. doi: 10.1371/journal.pone.0043031. PubMed PMID: 22912779; PubMed Central PMCID: PMC3418241.
167. Khaperskyy D A, Hatchette T F, McCormick C. Influenza A virus inhibits cytoplasmic stress granule formation. FASEB J. 2012; 26(4):1629-39. doi: 10.10964: J. 0.11-196915. PubMed PMID: 22202676.
168. Courtney S C, Scherbik S V, Stockman B M, Brinton M A. West nile virus infections suppress early viral RNA synthesis and avoid inducing the cell stress granule response. J Virol. 2012; 86(7):3647-57. doi: 10.1128/JVI.06549-11. PubMed PMID: 22258263; PubMed Central PMCID: PMC3302502.
169. Lindquist M E, Mainou B A, Dermody T S, Crowe J E, Jr. Activation of protein kinase R is required for induction 169. (continued) of stress granules by respiratory syncytial virus but dispensable for viral replication. Virology. 2011; 413(1):103-10. doi: 10.1016/j.virol.2011.02.009. PubMed PMID: 21377708; PubMed Central PMCID: PMC3072468.
170. Simpson-Holley M, Kedersha N, Dower K, Rubins K H, Anderson P, Hensley L E, Connor J H. Formation of antiviral cytoplasmic granules during orthopoxvirus infection. J Virol. 2011; 85(4):1581-93. doi: 10.1128/JVI.02247-10. PubMed PMID: 21147913; PubMed Central PMCID: PMC3028896.
171. Qin Q, Hastings C, Miller C L. Mammalian orthoreovirus particles induce and are recruited into stress granules at early times postinfection. J Virol. 2009; 83(21): 11090-101. doi: 10.1128/JVI.01239-09. PubMed PMID: 19710141; PubMed Central PMCID: PMC2772771.
172. Ma Y, Hendershot L M. Delineation of a negative feedback regulatory loop that controls protein translation during endoplasmic reticulum stress. The Journal of biological chemistry. 2003; 278(37):34864-73. doi: 10.1074/jbc.M301107200. PubMed PMID: 12840028.
173. Novoa I, Zeng H, Harding H P, Ron D. Feedback inhibition of the unfolded protein response by GADD34-mediated dephosphorylation of eIF2alpha. J Cell Biol. 2001; 153(5):1011-22. PubMed PMID: 11381086; PubMed Central PMCID: PMC2174339.
174. Ruggieri A, Dazert E, Metz P, Hofmann S, Bergeest J P, Mazur J, Bankhead P, Hiet M S, Kallis S, Alvisi G, Samuel C E, Lohmann V, Kaderali L, Rohr K, Frese M, Stoecklin G, Bartenschlager R. Dynamic oscillation of translation and stress granule formation mark the cellular response to virus infection. Cell host & microbe. 2012; 12(1):71-85. doi: 10.1016/j.chom.2012.05.013. PubMed PMID: 22817989; PubMed Central PMCID: PMC3873964.
175. Rojas M, Vasconcelos G, Dever T E. An eIF2alpha-binding motif in protein phosphatase 1 subunit GADD34 and its viral orthologs is required to promote dephosphorylation of eIF2alpha. Proceedings of the National Academy of Sciences of the United States of America. 2015; 112(27):E3466-75. doi: 10.1073/pnas.1501557112. PubMed PMID: 26100893; PubMed Central PMCID: PMC4500263.

What is claimed is:

1. A method of increasing an anti-viral response in a cell, the method consisting essentially of contacting the cell with nitazoxanide, wherein the anti-viral response is an anti-viral stress response.

2. The method of claim 1, wherein the anti-viral response comprises an increase in the expression level of a protein in a cell selected from the group consisting of an interferon-induced transmembrane (IFITM) protein, protein kinase R (PKR), retinoic acid-inducible gene 1 (RIG-I), and growth arrest and DNA damage-inducible protein (GADD34).

3. The method of claim 2, wherein the IFITM protein is selected from the group consisting of IFITM1, IFITM2, IFITM3, and IFITM5.

4. The method of claim 1, wherein the anti-viral response is an increase of phosphorylation of eIF2α.

5. The method of claim 1, wherein the contacting is in vitro.

6. The method of claim 1, wherein the contacting is in vivo.

7. The method of claim 6, wherein the in vivo contacting is done in a mammal.

8. The method of claim 7, wherein the mammal is a human.

9. The method of claim 1, wherein the nitazoxanide is the sole anti-viral therapeutic.

10. A method of measuring an anti-viral response in a patient who has been administered nitazoxanide as a first anti-viral therapeutic, the method comprising measuring an expression level of interferon-induced transmembrane (IFITM) protein, protein kinase R (PKR), retinoic acid-inducible gene 1 (RIG-I), and growth arrest or DNA damage-inducible protein (GADD34).

11. The method of claim 10, further comprising administering nitazoxanide and/or a second anti-viral therapeutic.

12. A method of measuring an anti-viral response following administration of nitazoxanide, the method comprising a. measuring a first expression level of interferon-induced transmembrane (IFITM) protein, protein kinase R (PKR), retinoic acid-inducible gene 1 (RIG-I), and growth arrest or DNA damage-inducible protein (GADD34) in a subject;

b. administering nitazoxanide to the subject;

c. measuring a second expression level of interferon-induced transmembrane (IFITM) protein, protein kinase R (PKR), retinoic acid-inducible gene 1 (RIG-I), and growth arrest or DNA damage-inducible protein (GADD34) in a subject.

13. A method of increasing an anti-viral response in a cell, the method consisting essentially of contacting the cell with nitazoxanide, wherein the anti-viral response comprises formation of stress granules and/or increase in cellular acidity.

14. A method of increasing an anti-viral stress response in a cell, the method consisting essentially of contacting a cell with nitazoxanide in vivo, thereby increasing an anti-viral stress response in the cell.

* * * * *

SEQUENCE LISTING

<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atgtcgtctg gtccctgttc                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gggatgacga tgagcagaat                                                  20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gctgaggaag atgctggttc                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
tccatatcct gtccctggag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggagacttg cctggtgaaa                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6 cagggtggt tattgcatct                                               20

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaatgggagg cttgaatact gcct                                         24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tagcaaagat gttctggagc atctc                                        25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcttctcgaa ccccgagtga                                              20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cctctgatgg caccacca                                                18
```

```
<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agaagaaggg gcccaaagt                                                  19

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaagatcacc cggcctacat                                                 20

<210> SEQ ID NO 13
<211> LENGTH: 227
<212> TYPE: DNA
<213> ORGANISM: Unknown
<220> FEATURE:
<223> OTHER INFORMATION: Description of Unknown:
      TNF promoter sequence

<400> SEQUENCE: 13
gcgatggaga agaaaccgag acagaaggtg cagggcccac taccgcttcc tccagatgag      60
ctcatgggtt tctccaccaa ggaagttttc cgctggttga atgattcttt ccccgccctc     120
ctctcgcccc agggacatat aaaggcagtt gttggcacac ccagccagca gacgctccct     180
cagcaaggac agcagaggac cagctaagag ggagagaagc aactaca                   227
```